US007288540B2

(12) United States Patent
Apodaca et al.

(10) Patent No.: US 7,288,540 B2
(45) Date of Patent: Oct. 30, 2007

(54) PHENYLALKYNES

(75) Inventors: Richard Apodaca, San Diego, CA (US); Xiaohu Deng, San Diego, CA (US); Jill A. Jablonowski, San Diego, CA (US); Neelakandha Mani, San Diego, CA (US); Chennagiri R. Pandit, San Diego, CA (US); Wei Xiao, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 11/490,394

(22) Filed: Jul. 20, 2006

(65) Prior Publication Data

US 2006/0258859 A1    Nov. 16, 2006

Related U.S. Application Data

(60) Division of application No. 10/464,582, filed on Jun. 17, 2003, now abandoned, which is a continuation-in-part of application No. 10/307,870, filed on Dec. 2, 2002, now Pat. No. 6,884,803.

(60) Provisional application No. 60/339,523, filed on Dec. 10, 2001.

(51) Int. Cl.
*C07D 413/06* (2006.01)
*A61K 31/5377* (2006.01)

(52) U.S. Cl. ............... 514/235.5; 544/129; 544/141; 544/162; 514/237.8

(58) Field of Classification Search ............... 544/129, 544/141, 162; 514/235.5, 237.8
See application file for complete search history.

(56) References Cited

U.S. PATENT DOCUMENTS

| | | |
|---|---|---|
| 5,217,986 A | 6/1993 | Pomponi et al. |
| 5,352,707 A | 10/1994 | Pompni et al. |
| 5,869,479 A | 2/1999 | Kreutner et al. |

FOREIGN PATENT DOCUMENTS

| | | |
|---|---|---|
| EP | 0978512 A1 | 2/2000 |
| WO | WO99/42458 | 8/1999 |
| WO | WO99/59969 | 11/1999 |
| WO | WO99/599699 A1 | 11/1999 |
| WO | WO 01/66534 A2 | 9/2001 |
| WO | WO 02/05501 A2 | 7/2002 |
| WO | WO 02/055501 A2 | 7/2002 |
| WO | WO 02/076925 A2 | 10/2002 |
| WO | WO 03/050099 A1 | 6/2003 |

OTHER PUBLICATIONS

Leurs et al. {Therapeutic potential of histamine H3 receptor agonists and antagonists: TiPS-May 1998 (vol. 19), 177-183}.*

Albengres, E. et al. Systemic Antifungal Agents. Drug Safety (Feb. 1998) 18(2):83-97.
Ali, S.M. et al. Design, Synthesis, and Structure-Activity Relationships of Acetylene-Based Histamine H3 Receptor Antagonists. J. Med. Chem. (1999) 42(5):903-909.
Arrang, J.-M. et al. Auto-inhibition of Brain Histamine Release Mediated by a Novel Class (H3) of Histamine Receptor. Nature (Apr. 1983) 302:832-837.
Ash, A.S.F.; Schild, H.O. Receptors Mediating Some Actions of Histamine. Br. J. Pharmac. Chemother. (1966) 27:427-439.
Back, D.J.; Tjia, J.F. Inhibition of Tolbutamide Metabolism by Substituted Imidazole Drugs In Vivo: Evidence for a Structure-Activity Relationship. Br. J. Pharmacol. (1985) 85:121-126.
Barnes, J.C. et al. The Selective Histamine H3 Receptor Antagonist Thioperamide Improves Cognition and Enhances Hippocampal Acetylcholine Release In Vivo. Soc. Neurosci. Abstr. (1993) 19:1813.
Bioworld Today, Mar. 2, 1999, p. 3.
Black, J.W. et al. Definition and Antagonism of Histamine H2-Receptors. Nature (Apr. 1972) 236:385-390.
Della, E. W. et al.: "Synthesis of Bridgehead Nitrogen Hetrocycles via Cyclization of alpha-Ammonio 5-Hexenyl Radicals" Journal of Organic Chemistry, vol. 64, No. 6, 1999, pp. 1798-1806, XP002255631 Scheme 3, preparation of compound 13 (R=H) p. 1803, right-hand column, paragraph 8.
Ding, Y.-S. et al. Synthesis of High Specific Activity (+)- and (−)-6-[18F]Fluoronorepinephrine via the Nucleophilic Aromatic Substitution Reaction. J. Med. Chem. (1991) 34(2):767-771.
Ganellin, C.R. et al. Synthesis of Potent Non-Imidazole Histamine H3-Receptor Antagonists. Arch. Pharm. Pharm. Med. Chem. (Weinheim, Ger.) (1998) 331:395-404.
Garbag, M. et al. S-[2-(4-Imidazolyl)ethyl]isothiourea, a Highly Specific and Potent Histamine H3 Receptor Agonist. J. Pharmacol. Exp. Ther. (1992) 263(1):304-310.
Glase et al.: "Aryl 1-But-3-ynyl-4-phenyl-1,2,3,6-tetratrydropy ridines as Potential Antipsychotic Agents: Synthesis and Structure-Activity Relatiioinships" Journal of Medicinal Chemistry, American Chemical Society. Washington, US, vol. 39, No. 16, (Jul. 1, 1996), pp. 3179-3187, XP002092426 ISSN: 0022-2623 Scheme 1a.
Gliatech Inc. Press Release Nov. 5, 1998.

(Continued)

*Primary Examiner*—Kahsay Habte
(74) *Attorney, Agent, or Firm*—John W. Harbour

(57) ABSTRACT

Substituted phenylalkynes of formula (I)

compositions containing them and their methods of use to treat histamine related disorders are described, wherein $R^1$, $R^2$, $R^3$, $R^4$, $R^5$ and n are as defined.

21 Claims, No Drawings

OTHER PUBLICATIONS

Ichinose, M.; Barnes, P.J. Histamine H3-Receptors Modulate Nonadrenergic Noncholinergic Neural Bronchonconstriction in Guinea-Pig In Vivo. Eur. J. Pharmacol. (1989) 174(1):49-55.

Imamura, M. et al. Unmasking of Activated Histamine H3-Receptors in Myocardial Ischemia: Their Role as Regulators of Exocytotic Norepinephrine Release. J. Pharmacol. Exp. Ther. (1994) 271(3):1259-1266.

Kapetanovic, I.M.; Kupferberg, H.J. Nafimidone, an Imidazole Anticonvulsant, and Its Metabolite as Potent Inhibitors of Microsomal Metabolism of Phenytoin and Carbamazepine. Drug Metab. Dispos. (1984) 12(5):560-564.

Korte, A. et al. Characterization and Tissue Distribution of H3 Histamine Receptors in Guinea Pigs by N alpha-Methylhistamine. Biochem. Biophys. Res. Commun. (May 1990) 168(3):979-986.

Krause, M. et al. Medicinal Chemistry of Histamine H3 Receptor Agonists; In The Histamine H3 Receptor—A Target for New Drugs Leurs, R.; Timmerman, H. (Eds.) Elsevier (1998) 175-196.

Lavrijsen, K. et al. Induction Potential of Antifungals Containing an Imidazole or Triazole Moiety. Biochem. Pharmacol. (1986) 35(11):1867-1878.

Leurs, R. et al. The Medicinal Chemistry and Therapeutic Potentials of Ligands of the Histamine H3 Receptor. Prog. Drug Res. (1995) 45:107-165.

Lin, J.-S. et al. Involvement of Histaminergic Neurons in Arousal Mechanisms Demonstrated with H3-Receptor Ligands in the Cat. Brain Res. (1990) 523:325-330.

Linney, I.D. et al. Design, Synthesis, and Structure-Activity Relationships of Novel Non-Imidazole Histamine H3 Receptor Antagonists. J. Med. Chem. (2000) 43(12):2362-2370.

Lovenberg, T.W. et al. Cloning and Functional Expression of the Human Histamine H3 Receptor. Mol. Pharmacol. (1999) 55:1101-1107.

Lovenberg, T.W. et al. Cloning of Rat Histamine H3 Receptor Reveals Distinct Species Pharmacological Profiles. J. Pharmacol. Exp. Ther. (2000) 293(3):771-778.

Machidori, H. et al. Zucker Obese Rats: Defect in Brain Histamine Control of Feeding. Brain Res. (1992) 590:180-186.

McLeod, R.L. et al. Antimigraine and Sedative Activity of SCH 50971: A Novel Orally-Active Histamine H3 Receptor Agonist. Soc. Neurosci. Abstr. (1996) 22:2010.

Meier, G. et al. Piperidino-Hydrocarbon Compounds as Novel Non-Imidazole Histamine H3-Receptor Antagonists. Bioorg. Med. Chem. (2002) 10:2535-2542.

Monti, J.M. et al. Effects of Selective Activation or Blockade of the Histamine H3 Receptor on Sleep and Wakefulness. Eur. J. Pharmacol. (1991) 205(3):283-287.

Morisset, S. et al. High Constitutive Activity of Native H3 Receptors Regulates Histamine Neurons in Brain. Nature (Dec. 2000) 408:860-864.

Oda, T. et al. Molecular Cloning and Characterization of a Novel Type of Histamine Receptor Preferentially Expressed in Leukocytes. J. Biol. Chem. (2000) 275(47):36781-36786.

Panula, P. et al. Significant Changes in the Human Brain Histaminergic System in Alzheimer's Disease. Soc. Neurosci. Abstr. (1995) 21:1977.

Phelps, M.E. Positron Emission Tomography Provides Molecular Imaging of Biological Processes. Proc. Natl. Acad. Sci. (2000) 97(16):9226-9233.

Phillips, J.G.; Ali, S.M. Medicinal Chemistry of Histamine H3 Receptor Antagonists; In The Histamine H3 Receptor—A Target for New Drugs Leurs, R.; Timmerman, H. (Eds.) Elsevier (1998) 197-222.

Rouleau, A. et al. Bioavailability, Antinociceptive and Antiinflammatory Properties of BP 2-94, a Histamine H3 Receptor Agonist Prodrug. J. Pharmacol. Exp. Ther. (1997) 281(3):1085-1094.

Schlicker, E.; Marr, I. The Moderate Affinity of Clozapine at H3 Receptors Is Not Shared by Its Two Major Metabolites and by Structurally Related and Unrelated Atypical Neuroleptics. Naunyn-Schmiedeberg's Arch. Pharmacol. (1996) 353:290-294.

Sheets, J.J.; Mason, J.I. Ketoconazole: a Potent Inhibitor of Cytochrome P-450-Dependent Drug Metabolism in Rat Liver. Drug Metab. Dispos. (1984) 12(5):603-606.

Stark, H. et al. Developments of Histamine H3-Receptor Antagonists. Drugs Future (1996) 21(5):507-520.

Tozer, M.J.; Kalindjian, S.B. Histamine H3 Receptor Antagonists. Exp. Opin. Ther. Patents (2000) 10(7):1045-1055.

Walczynski, K. et al. Non-Imidazole Histamine H3 Ligands, Part 2: New 2-Substituted Benzothiazoles as Histamine H3 Antagonists. Arch. Pharm. Pharm. Med. Chem. (Weinheim, Ger.) (1999) 332:389-398.

Walczynski, K. et al. Non-Imidazole Histamine H3 Ligands. Part I. Synthesis of 2-(1-Piperazinyl)- and 2-(Hexahydro-1H-1,4-diazepin-1-yl)benzothiazole Derivatives as H3-Antagonists with H1 Blocking Activities. Farmaco (1999) 54:684-694.

West, R.E. et al. Identification of Two H3-Histamine Receptor Subtypes. Mol. Pharmacol. (1990) 38(5):610-613.

West, R.E., Jr. et al. The Profiles of Human and Primate [3H]N alpha-methylhistamine Binding Differ from That of Rodents. Eur. J. Pharmacol. (1999) 377:233-239.

Wright, J. L. et al.: "Subtype-Selectice N-Methyl-D-Aspartate Receptor Antagonists: Synthesis and Biological Evaluation of 1-(Arylalkynl)-4-Benzylpiperidines" Journal of Medicinal Chemistry, vol. 42, No. 13, 1999, pp. 2469-2477, XP002255630 Scheme 1; Table 1 compound 33.

Yokoyama, H. et al. Effect of Thioperamide, a Histamine H3 Receptor Antagonist, on Electrically Induced Convulsions in Mice. Eur. J. Pharmacol. (1993) 234:129-133.

* cited by examiner

PHENYLALKYNES

This application is a divisional application of U.S. Ser. No. 10/464,582, filed on Jun. 17, 2003 (now abandoned) which is a continuation-in-part of U.S. Ser. No. 10/307,870, filed on Dec. 2, 2002 (now U.S. Pat. No. 6,884,803), which claims priority to provisional application 60/339,523, filed on Dec. 10, 2001, all of which are incorporated herein by reference in their entirety.

FIELD OF THE INVENTION

The present invention relates to phenylalkynes, their synthesis and their use, for example, for the treatment of disorders and conditions mediated by the histamine receptor.

BACKGROUND OF THE INVENTION

Histamine[2-(imidazol-4-yl)ethylamine] is a transmitter substance. Histamine exerts a physiological effect via multiple distinct G-protein coupled receptors. It plays a role in immediate hypersensitivity reactions and is released from mast cells following antigen IgE antibody interaction. The actions of released histamine on the vasculature and smooth muscle system account for the symptoms of the allergic response. These actions occur at the $H_1$ receptor (Ash, A. S. F. and Schild, H. O., *Br. J. Pharmac. Chemother.* 1966, 27:427-439) and are blocked by the classical antihistamines (e.g. diphenhydramine). Histamine is also an important regulator of gastric acid secretion through its action on parietal cells. These effects of histamine are mediated via the $H_2$ receptor (Black, J. W. et al., *Nature* 1972, 236:385-390) and are blocked by $H_2$ receptor antagonists (e.g. cimetidine). The third histamine receptor —$H_3$— was first described as a presynaptic autoreceptor in the central nervous system (CNS) (Arrang, J.-M. et al., *Nature* 1983, 302:832-837) controlling the synthesis and release of histamine. Recent evidence has emerged showing that the $H_3$ receptors are also located presynaptically as heteroreceptors on serotonergic, noradrenergic, dopaminergic, cholinergic, and GABAergic (gamma-aminobutyric acid containing) neurons. These $H_3$ receptors have also recently been identified in peripheral tissues such as vascular smooth muscle. Consequently there are many potential therapeutic applications for histamine $H_3$ agonists, antagonists, and inverse agonists. (See: "*The Histamine $H_3$ Receptor—A Target for New Drugs*", Leurs, R., and Timmerman, H., (Eds.), Elsevier, 1998; Morisset, S. et al., *Nature* 2000, 408:860-864.) A fourth histamine receptor —$H_4$— was recently described by Oda, T. et al. (*J. Biol. Chem.* 2000, 275(47):36781-36786).

The potential use of histamine $H_3$ agonists in sleep/wake and arousal/vigilance disorders is suggested based on animal studies (Lin, J.-S. et al., *Brain Res.* 1990, 523:325-330; Monti, J. M. et al., *Eur. J. Pharmacol.* 1991, 205:283-287). Their use in the treatment of migraine has also been suggested (McLeod, R. L. et al., *Soc. Neurosci. Abstr.* 1996, 22:2010) based on their ability to inhibit neurogenic inflammation. Other applications could be a protective role in myocardial ischemia and hypertension where blockade of norepinephrine release is beneficial (Imamura, M. et al., *J. Pharmacol. Exp. Ther.* 1994, 271(3):1259-1266). It has been suggested that histamine $H_3$ agonists may be beneficial in asthma due to their ability to reduce non-adrenergic noncholinergic (NANC) neurotransmission in airways and to reduce microvascular leakage (Ichinose, M. and Barnes, P. J., *Eur. J. Pharmacol.* 1989, 174:49-55).

Several indications for histamine $H_3$ antagonists and inverse agonists have similarly been proposed based on animal pharmacology experiments with known histamine $H_3$ antagonists (e.g. thioperamide). These include dementia, Alzheimer's disease (Panula, P. et al., *Soc. Neurosci. Abstr.* 1995, 21:1977), epilepsy (Yokoyama, H. et al., *Eur. J. Pharmacol.* 1993, 234:129-133), narcolepsy, eating disorders (Machidori, H. et al., *Brain Res.* 1992, 590:180-186), motion sickness, vertigo, attention deficit hyperactivity disorders (ADHD), learning and memory (Barnes, J. C. et al., *Soc. Neurosci. Abstr.* 1993, 19:1813), and schizophrenia (Schlicker, E. and Marr, I., *Naunyn-Schmiedeberg's Arch. Pharmacol.* 1996, 353:290-294). (Also see: Stark, H. et al., *Drugs Future* 1996, 21(5):507-520; and Leurs, R. et al., *Prog. Drug Res.* 1995, 45:107-165 and references cited therein.) Histamine $H_3$ antagonists, alone or in combination with a histamine $H_1$ antagonist, are reported to be useful for the treatment of upper airway allergic response (U.S. Pat. Nos. 5,217,986; 5,352,707 and 5,869,479). Recently, a histamine $H_3$ antagonist (GT-2331) was identified and is being developed by Gliatech Inc. (Gliatech Inc. Press Release Nov. 5, 1998; *Bioworld Today*, Mar. 2, 1999) for the treatment of CNS disorders.

As noted, the prior art related to histamine $H_3$ ligands has been comprehensively reviewed ("*The Histamine $H_3$ Receptor—A Target for New Drugs*", Leurs, R., and Timmerman, H., (Eds.), Elsevier, 1998). Within this reference the medicinal chemistry of histamine $H_3$ agonists and antagonists was reviewed (see: Krause, M. et al., and Phillips, J. G. and Ali, S. M., respectively). The importance of an imidazole moiety containing only a single substitution in the 4 position was noted together with the deleterious effects of additional substitution on activity. Particularly, methylation of the imidazole ring at any of the remaining unsubstituted positions was reported to strongly decrease activity. Additional publications support the hypothesis that an imidazole function is essential for high affinity histamine $H_3$ receptor ligands (see: Ali, S. M. et al., *J. Med. Chem.* 1999, 42:903-909, and Stark, H. et al., and references cited therein). However many imidazole-containing compounds are substrates for histamine methyl transferase, the major histamine metabolizing enzyme in humans, which leads to shortened half-lives and lower bioavailability (see: Rouleau, A. et al., *J. Pharmacol. Exp. Ther.* 1997, 281(3):1085-1094). In addition, imidazole-containing drugs, via their interaction with the cytochrome P450 monooxygenase system, can result in unfavorable biotransformations due to enzyme induction or enzyme inhibition (see: Kapetanovic, I. M. and Kupferberg, H. J., *Drug Metab. Dispos.* 1984, 12(5):560-564; Sheets, J. J. and Mason, J. I., *Drug Metab. Dispos.* 1984, 12(5):603-606; Back, D. J. and Tjia, J. F., *Br. J. Pharmacol.* 1985, 85:121-126; Lavrijsen, K. et al., *Biochem. Pharmacol.* 1986, 35(11):1867-1878; Albengres, E. et al., *Drug Safety* 1998, 18(2):83-97). The poor blood-brain barrier penetration of earlier histamine $H_3$ receptor ligands may also be associated with the imidazole fragment (Ganellin, C. R. et al., *Arch. Pharm. Pharm. Med. Chem.* (Weinheim, Ger.) 1998, 331: 395-404).

More recently, several publications have described histamine $H_3$ ligands that do not contain an imidazole moiety, for example: Ganellin, C. R. et al.; Walczynski, K. et al., *Arch. Pharm. Pharm. Med. Chem.* (Weinheim, Ger.) 1999, 332: 389-398; Walczynski, K. et al., *Farmaco* 1999, 54:684-694; Linney, I. D. et al., *J. Med. Chem.* 2000, 43:2362-2370; Tozer, M. J. and Kalindjian, S. B., *Exp. Opin. Ther. Patents* 2000,10:1045-1055; U.S. Pat. No. 5,352,707; PCT Application WO 99/42458; PCT Application WO 02/076925; and EP Application 0978512, Feb. 9, 2000.

The compounds of the present invention do not contain the imidazole moiety, and its inherent liabilities, and yet maintain potency at the human $H_3$ receptor as determined by receptor binding to the human histamine $H_3$ receptor (see: Lovenberg, T. W. et al., *Mol. Pharmacol.* 1999, 55:1101-1107). Screening using the human receptor is particularly important for the identification of new therapies for the treatment of human disease. Conventional binding assays, for example, are determined using rat synaptosomes (Garbarg, M. et al., *J. Pharmacol. Exp. Ther.* 1992, 263(1):304-310), rat cortical membranes (West, R. E. et al., *Mol. Pharmacol.* 1990, 38:610-613), and guinea pig brain (Korte, A. et al., *Biochem. Biophys. Res. Commun.* 1990, 168(3): 979-986). Only limited studies have been performed previously using human tissue but these allude to significant differences in the pharmacology of rodent and primate receptors (West, R. E. et al., *Eur. J. Pharmacol.* 1999, 377:233-239).

We now describe a series of phenylalkynes with the ability to modulate the activity of the histamine receptor, specifically the $H_3$ receptor, without the inherent problems associated with the presence of an imidazolyl moiety.

SUMMARY OF THE INVENTION

The present invention is directed to pharmaceutically active phenylalkynes, methods of making them, and methods of using them. The invention features a compound of formula (I)

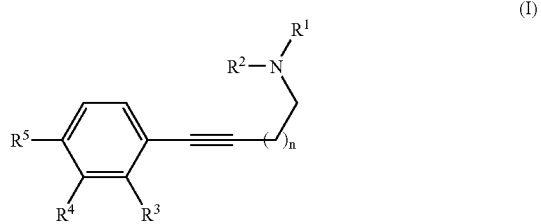

wherein n is an integer from 0 to 1;

$R^1$ and $R^2$ are independently selected from $C_{1-3}$ alkyl, allyl, and $C_{3-8}$ cycloalkyl, or taken together with the nitrogen to which they are attached, they form a non-aromatic 4-7 membered heterocyclyl optionally including up to two additional heteroatoms independently selected from O, S, and N;

one of $R^3$, $R^4$, and $R^5$ is G, one of the remaining two is hydrogen, and the other is selected from hydrogen, fluoro, and chloro;

G is $L^2Q$;

$L^2$ is methylene;

Q is $NR^8R^9$ wherein $R^8$ is independently selected from hydrogen, $C_{1-6}$ alkyl, $C_{3-6}$ alkenyl, 6-9 membered carbocyclyl, 3-12 membered heterocyclyl (preferably 5-9 or 5-8-membered heterocyclyl), phenyl, (5-9-membered heterocyclyl)$C_{1-6}$ alkylene, and (phenyl)$C_{1-6}$ alkylene; and $R^9$ is independently selected from $C_{1-6}$ alkyl, $C_{3-6}$ alkenyl, 6-9 membered carbocyclyl, 3-12 membered heterocyclyl (preferably 5-9 or 5-8-membered heterocyclyl), phenyl, (5-9-membered heterocyclyl)$C_{1-6}$ alkylene, and (phenyl) $C_{1-6}$ alkylene;

or

Q is a saturated 3-13 membered N-linked heterocyclyl, wherein, in addition to the N-linking nitrogen, the 3-13 membered heterocyclyl may optionally contain between 1 and 3 additional heteroatoms independently selected from O, S, and N;

wherein each of the above alkyl, alkylene, alkenyl, heterocyclyl, cycloalkyl, carbocyclyl, and aryl groups of Formula (I) may each be independently and optionally substituted with between 1 and 3 substituents independently selected from methoxy, halo, amino, nitro, hydroxyl, and $C_{1-3}$ alkyl;

and wherein 1-3 substituents of Q can be further independently selected (in addition to the preceding paragraph) from tert-butyloxycarbonyl, carboxamide, $C_{1-6}$ alkyl, 5-9-membered heterocyclyl, N($C_{1-6}$ alkyl)(5-9 membered heterocyclyl), NH(5-9 membered heterocyclyl), O(5-9 membered heterocyclyl), (5-9 membered heterocyclyl)$C_{1-3}$ alkylene, phenyl, $C_{1-2}$-hydroxyalkylene, $C_{2-6}$ alkoxy, ($C_{3-6}$ cycloalkyl)-O—, phenyl, (phenyl)$C_{1-3}$ alkylene, and (phenyl)$C_{1-3}$ alkylene-O— and where said substituent groups of Q may optionally have between 1 and 3 substituents independently selected from trifluoromethyl, halo, nitro, cyano, and hydroxy;

or a pharmaceutically acceptable salt, ester, or amide thereof.

The present invention also features methods of making a compound of formula (I), a pharmaceutically acceptable salt, ester, or amide thereof, comprising at least one of the following steps: Reacting a compound of formula (VI) with a compound of formula (V),

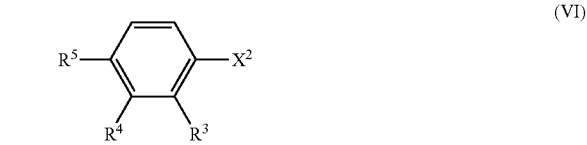

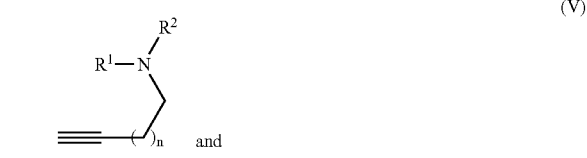

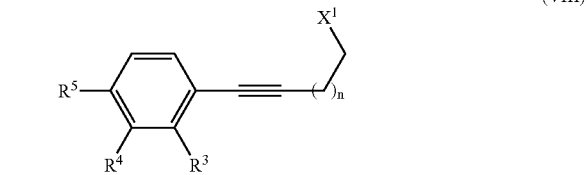

performing a nucleophilic substitution of $X_1$ in compound of formula (VIII) with an organic base $R^1R^2NH$, wherein x is a suitable leaving group in a coupling reaction with an alkyne, and $X^1$ is a suitable leaving group in a nucleophilic substitution with an amine.

The present invention also features methods of making a compound of formula (I), a pharmaceutically acceptable salt, ester, or amide thereof, wherein more specifically one of $R^3$ and $R^5$ is G, one of the remaining and $R^4$ is H, and the other is selected from hydrogen, fluoro, and chloro, comprising: reacting at least one of the compounds of formulae (XXIIIw) and (XXIIIow) with a compound of formula (V);

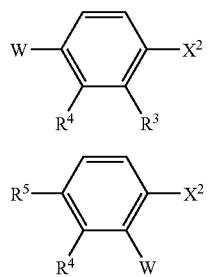

wherein W is C(O)H (denoting

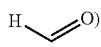

or G, and $X^2$ is a suitable leaving group in a coupling reaction with an alkyne.

The present invention also features methods of making a compound of formula (I), a pharmaceutically acceptable salt, ester, or amide thereof, wherein more specifically $R^4$ is G, one of the remaining $R^3$ and $R^5$ is hydrogen, and the other is selected from hydrogen, fluoro, and chloro G is a m-substituent with respect to the alkyne chain substituent, comprising: reacting a compound of formula (XXIIImw) with a compound of formula (V).

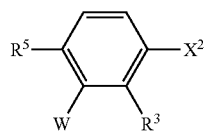

wherein W is C(O)H or G, and $X^2$ is a suitable leaving group in a coupling reaction with an alkyne.

The present invention also features methods of making a compound of formula (I), a pharmaceutically acceptable salt, ester, or amide thereof, comprising reacting a compound of formula (VII) with an organic base $R^1R^2NH$ in the presence of a trialkylphosphonium halide and a base.

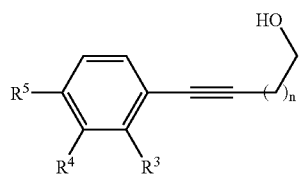

The invention also features a pharmaceutical composition comprising a compound of the invention and a pharmaceutically acceptable carrier; and methods of preparing or formulating such compositions. A composition of the invention may further include more than one compound of the invention, or a combination therapy (combination formulation or combination of differently formulated active agents).

The invention also provides methods of treating certain conditions and diseases, each of which methods includes administering a therapeutically effective (or jointly effective) amount of a compound or composition of the invention to a subject in need of such treatment. The disclosed compounds are useful in methods for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof. For example, the invention features methods for preventing, inhibiting the progression of, or treating upper airway allergic response, asthma, itch, nasal congestion and allergic rhinitis.

In yet another embodiment, the disclosed compounds may be used in a combination therapy method including administering a jointly effective dose of an $H_3$ antagonist and administering a jointly effective dose of a histamine $H_1$ antagonist, such as loratidine (CLARITIN™), desloratidine (CLARINEX™), fexofenadine (ALLEGRA™) and cetirizine (ZYRTEC™), for the treatment of allergic rhinitis, nasal congestion, and allergic congestion.

In yet another embodiment, the disclosed compounds may be used in a combination therapy method, including administering a jointly effective dose of an $H_3$ antagonist and administering a jointly effective dose of a neurotransmitter re-uptake blocker, such as a selective serotonin re-uptake inhibitor (SSRI) or a non-selective serotonin, dopamine or norepinephrine re-uptake inhibitor, including fluoxetine (PROZAC™), sertraline (ZOLOFT™), paroxetine (PAXIL™) and amitryptyline, for the treatment of depression, mood disorders or schizophrenia.

Additional features and advantages of the invention will become apparent from the detailed description and examples below, and the appended claims.

DETAILED DESCRIPTION OF THE INVENTION

The present invention provides phenylalkyne compounds useful for the treatment of disorders and conditions modulated by a histamine receptor.

A. Terms

Certain terms are defined below and by their usage throughout this disclosure.

As used herein, "halo" or "halogen" shall mean monovalent radicals of chlorine, bromine, fluorine and iodine.

As used herein, the term "alkyl", whether used alone or as part of a substituent group, shall include straight and branched carbon chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms. "Alkylene" refers to a bivalent hydrocarbyl group, such as methylene ($CH_2$), ethylene (—$CH_2$—$CH_2$—) or propylene (—$CH_2CH_2CH_2$—), and so on.

As used herein, unless otherwise noted, "alkenyl" shall mean a straight or branched hydrocarbon group with at least two hydrogen atoms replaced with a pi bond to form a carbon-carbon double bond, such as propenyl, butenyl, pentenyl, and so on. Where the alkenyl group is $R^8$ or $R^9$, the open radical (point of attachment to the rest of the molecule) is on $sp^3$ carbon, as illustrated by allyl, and the double bond or bonds is therefore at least alpha (if not beta, gamma, etc.) to the open radical.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "cycloalkyl" shall denote a three- to eight-membered, saturated monocyclic carbocyclic ring structure. Suitable examples include cyclopropyl, cyclobutyl, cyclopentyl, cyclohexyl, cycloheptyl and cyclooctyl.

As used herein, unless otherwise noted, "cycloalkenyl" shall denote a three- to eight-membered, partially unsaturated, monocyclic, carbocyclic ring structure, wherein the ring structure contains at least one double bond. Suitable examples include cyclohexenyl, cyclopentenyl, cycloheptenyl, cyclooctenyl, cyclohexa-1,3-dienyl and the like.

As used herein, unless otherwise noted, "aryl" shall refer to carbocyclic aromatic groups such as phenyl, naphthyl, and the like. Divalent radicals include phenylene (—$C_6H_4$—) which is preferably phen-1,4-diyl, but may also be phen-1,3-diyl.

As used herein, unless otherwise noted, "aralkyl" shall mean any alkyl group substituted with an aryl group such as phenyl, naphthyl and the like. Examples of aralkyls include benzyl, phenethyl, and phenylpropyl.

As used herein, unless otherwise noted, "carbocyclyl" shall mean any cyclic group consisting of 3-13 carbon atoms, and preferably 6-9 carbon atoms, in the skeleton ring or rings, if the carbocycle is a fused or spiro bicyclic or tricyclic group. A carbocycle may be saturated, unsaturated, partially unsaturated, or aromatic. Examples include cycloalkyl, cycloalkenyl, cycloalkynyl; specific examples include phenyl, benzyl, indanyl, and biphenyl. A carbocycle may have substituents that are not carbon or hydrogen, such as hydroxy, halo, halomethyl, and so on as provided elsewhere herein.

As used herein, unless otherwise noted, the terms "heterocycle", "heterocyclyl" and "heterocycle" shall denote any three-, four-, five-, six-, seven-, or eight-membered monocyclic, eight or nine or ten or eleven membered bicyclic or twelve or thirteen or fourteen membered tricyclic ring structure containing at least one heteroatom moiety selected from the group consisting of N, O, SO, $SO_2$, (C=O), and S, and preferably N, O, or S, optionally containing one to four additional heteroatoms in each ring. In some embodiments, the heterocyclyl contains between 1 and 3 or between 1 and 2 additional heteroatoms. Unless otherwise specified, a heterocyclyl may be saturated, partially unsaturated, aromatic or partially aromatic. The heterocyclyl group may be attached at any heteroatom or carbon atom, which results in the creation of a stable structure.

Exemplary monocyclic heterocyclic groups can include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, hexahydroazepinyl, 4-piperidinyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, thietanyl, thiiranyl, triazinyl, triazolyl, tetrazolyl, azetidinyl and the like.

For example, where Q is a saturated 3-13 membered N-linked heterocyclyl, Q necessarily contains at least one nitrogen, and the carbon atoms are $sp^3$ hybridized.

In general, exemplary bicyclic heterocyclyls include benzthiazolyl, benzoxazolyl, benzoxazinyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopridyl, furopyridinyl (such as furo[2,3-c]pyridinyl, furo[3,1-b]pyridinyl), or furo[2,3-b]pyridinyl), dihydroisoindolyl, dihydroquinazolinyl (such as 3,4-dihydro-4-oxo-quinazolinyl), tetrahydroquinolinyl (such as 1,2,3,4-tetrahydroquinolinyl), tetrahydroisoquinolinyl(such as 1,2,3,4-tetrahydroisoquiunolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isoindolyl, tetrahydroindoazolyl (such as 4,5,6,7-tetrahydroindazolyl), isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl,

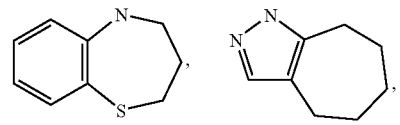

and the like.

Exemplary tricyclic heterocyclic groups include acridinyl, phenoxazinyl, phenazinyl, phenothiazinyl, carbozolyl, perminidinyl, phenanthrolinyl, carbolinyl, naphthothienyl, thianthrenyl, and the like.

Preferred heterocyclyl groups include morpholinyl, piperidinyl, piperazinyl, pyrrolidinyl, pyrimidinyl, pyridyl, pyrrolyl, imidazolyl, oxazolyl, isoxazolyl, acridinyl, azepinyl, hexahydroazepinyl, azetidinyl, indolyl, isoindolyl, thiazolyl, thiadiazolyl, quinolinyl, isoquinolinyl, 1,2,3,4-tetrahydroquinolinyl, 1,3,4-trihydroisoquinolinyl, 4,5,6,7-tetrahydroindadolyl, benzoxazinyl, benzoxazolyl, benzthiazolyl, benzimidazolyl, tetrazolyl, oxadiazolyl,

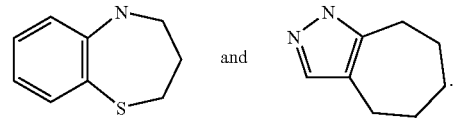

As used herein, unless otherwise noted, the term "heterocyclyl-alkyl" or "heterocyclyl-alkylene" shall denote any alkyl group substituted with a heterocyclyl group, wherein the heterocycly-alkyl group is bound through the alkyl portion to the central part of the molecule. Suitable examples of heterocyclyl-alkyl groups include, but are not limited to piperidinylmethyl, pyrrolidinylmethyl, piperidinylethyl, piperazinylmethyl, pyrrolylbutyl, piperidinylisobutyl, pyridylmethyl, pyrimidylethyl, and the like.

When a particular group is "substituted" (e.g., alkyl, alkylene, cycloalkyl, aryl, heterocyclyl, heteroaryl), that group may have one or more substituents, preferably from one to five substituents, more preferably from one to three substituents, most preferably from one to two substituents, independently selected from the list of substituents.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature used throughout this disclosure, the terminal portion of the designated side chain is described first, followed by the adjacent functionality toward the point of attachment. Thus, for example, a "phenyl (alkyl)amido(alkyl)" substituent refers to a group of the formula

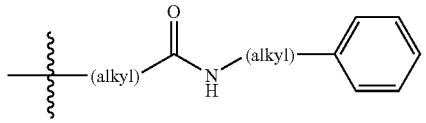

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes prevention, inhibition of onset, or alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Abbreviations used in the specification, particularly in the Schemes and Examples, are as follows:

| DBAD | = | Di-tert-butyl azodicarboxylate |
|---|---|---|
| DCE | = | 1,2-dichloroethane |
| DCM | = | Dichloromethane |
| DEAD | = | Diethyl azodicarboxylate |
| DIPEA | = | Disopropylethylamine |
| DMAC (or DMA) | = | N,N-dimethylacetamide |
| DMAP | = | 4-N,N-dimethylamino-pyridine |
| DME | = | 1,2-dimethoxyethane |
| DMF | = | Dimethylformamide |
| DMSO | = | Dimethylsulfoxide |
| TEA | = | Triethylamine |
| TFA | = | Trifluoroacetic acid |
| THF | = | Tetrahydrofuran |

The next section describes the compounds provided by the invention in more detail.

B. Compounds

The invention features compounds of formula (I) as described, for example, in the above summary section and in the claims. Preferred compounds include those wherein:

(a) $NR^1R^2$ taken together form piperidinyl, methylpiperidinyl, dimethylamino, pyrrolidinyl, diethylamino, methylethylamino, ethylpropylamino, or dipropylamino;

(b) $NR^1R^2$ taken together form piperidinyl, pyrrolidinyl, or diethylamino;

(c) $NR^1R^2$ taken together form piperidinyl or pyrrolidinyl;

(d) one of $R^4$ and $R^5$ is G;

(e) $R^4$ is G;

(f) $R^5$ is G;

(g) n is 1;

(h) Q is a saturated N-linked nitrogen-containing heterocyclyl;

(i) Q is selected from substituted or unsubstituted piperidinyl, substituted or unsubstituted piperazinyl, pyrrolinyl, pyrrolidinyl, thiomorpholinyl, and morpholinyl;

(j) substituted Q is selected from N—($C_{1-6}$ alkyl)piperazinyl, N-phenyl-piperazinyl, 1,3,8-triaza-spiro[4.5]decyl, and 1,4-dioxa-8-aza-spiro[4.5]decyl;

(k) Q is a monovalent radical of an amine selected from aziridine, 1,4,7-trioxa-10-aza-cyclododecane, thiazolidine, 1-phenyl-1,3,8-triaza-spiro[4.5]decan-4-one, piperidine-3-carboxylic acid diethylamide, 1,2,3,4,5,6-hexahydro-[2,3'] bipyridinyl, 4-(3-trifluoromethyl-phenyl)-piperazine, 2-piperazin-1-yl-pyrimidine, piperidine-4-carboxylic acid amide, methyl-(2-pyridin-2-yl-ethyl)-amine, [2-(3,4-dimethoxy-phenyl)-ethyl]-methyl-amine, thiomorpholinyl, allyl-cyclopentyl-amine, [2-(1H-indol-3-yl)-ethyl]-methyl-amine, 1-piperidin-4-yl-1,3-dihydro-benzoimidazol-2-one, 2-(piperidin-4-yloxy)-pyrimidine, piperidin-4-yl-pyridin-2-yl-amine, phenylamine, and pyridin-2-yl-amine;

(l) Q is selected from N-morpholinyl and N-piperidinyl, optionally substituted with between 1 and 3 substituents independently selected from hydroxyl, carboxamide, $C_{1-6}$ alkyl, 5-9 membered or 6-9 membered heterocyclyl, N($C_{1-6}$ alkyl)(5-9 membered or 6-9 membered heterocyclyl), NH(5-9 membered or 6-9 membered heterocyclyl), (5-9 membered or 6-9 membered heterocyclyl)$C_{1-3}$ alkylene, 5-9 membered or 6-9 membered heterocyclyl-O—, $C_{1-6}$ alkoxy, ($C_{3-6}$ cycloalkyl)-O—, phenyl, (phenyl)$C_{1-3}$ alkylene, and (phenyl)$C_{1-3}$ alkylene-O— where each of above heterocyclyl, phenyl, and alkyl groups may be optionally substituted with from 1 to 3 substituents independently selected from halogen, nitro, cyano, and $C_{1-3}$ alkyl;

(m) Q is substituted with a substituent comprising a 5-9 membered or 6-9 membered heterocyclyl group selected from: pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, and pyrrolyl;

(n) Q is a substituted or unsubstituted N-morpholinyl;

(o) $R^8$ is hydrogen;

(p) $R^9$ is selected from phenyl or 5-9 membered aromatic heterocyclyl, wherein said phenyl or aromatic heterocyclyl is optionally substituted with 1-3 substituents selected from halo, nitro, cyano, and $C_{1-3}$ alkyl;

(q) $R^9$ is selected from substituted or unsubstituted phenyl, pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl) $C_{1-6}$ alkylene, and pyrrolyl;

(r) R⁹ is substituted or unsubstituted phenyl;

(s) R⁹ is substituted or unsubstituted pyridyl;

(t) wherein n is 1; $R^1$ and $R^2$ are independently selected from $C_2$ alkyl, or taken together with the nitrogen to which they are attached, they form a non-aromatic 5-6 membered heterocyclyl optionally including an additional heteroatom independently selected from O, S, and N; one of $R^3$, $R^4$, and $R^5$ is G and the two remaining are H; G is $L^2Q$; $L^2$ is methylene; Q is $NR^8R^9$ wherein $R^8$ is independently selected from hydrogen, $C_{1-2}$ alkyl, $C_3$ alkenyl, 6-9 membered carbocycle, 3-12 membered heterocyclyl (preferably 5-9 or 6-9), phenyl, (5-9-membered heterocyclyl)$C_{1-6}$ alkylene, and (phenyl) $C_{1-6}$ alkylene; and $R^9$ is independently selected from $C_{1-2}$ alkyl, $C_3$ alkenyl, 5-9 membered carbocyclyl, 3-12 membered heterocyclyl (for example, 5-9 membered or 6-9 membered heterocyclyl, and in some cases preferably 6-membered), phenyl, (5-9-membered heterocyclyl)$C_{1-6}$ alkylene, and (phenyl) $C_{1-6}$ alkylene; or Q is a saturated 3-13 membered N-linked heterocyclyl (preferably 5-9 or 6-9), wherein, in addition to the N-linking nitrogen, the 3-13 membered heterocyclyl may optionally contain between 1 and 3 additional heteroatoms independently selected from O, S, and N; wherein each of the above alkyl, alkylene, alkenyl, alkenylene, heterocyclyl, cycloalkyl, and aryl groups may each be independently and optionally substituted with between 1 and 3 substituents independently selected from methoxy, halo, amino, nitro, hydroxyl, and $C_{1-3}$ alkyl; and wherein substituents of Q can be further independently selected from tert-butyloxycarbonyl, carboxamide, 6-9-membered heterocyclyl, NH(6-membered heterocyclyl), O(6-membered heterocyclyl), phenyl, $C_2$-hydroxyalkylene, hydroxy, and benzyl, and, where each of above heterocyclyl, phenyl, and alkyl substituent groups of Q may be optionally substituted with trifluoromethyl; or a pharmaceutically acceptable salt, ester, or amide thereof;

(u) (1) $NR^1R^2$ taken together form piperidinyl, pyrrolidinyl, or diethylamino, and (2) Q is selected from substituted or unsubstituted piperidinyl, piperazinyl, pyrrolinyl, pyrrolidinyl, thiomorpholinyl, and morpholinyl;

(v) (1) $NR^1R^2$ taken together form piperidinyl or pyrrolidinyl, (2) n is 1, and (3) Q is selected from morpholinyl and piperidinyl;

(w) Q is morpholinyl or substituted morpholinyl;

(x) $NR^1R^2$ taken together form piperidinyl, pyrrolidinyl, or diethylamino,
n is 1, and
wherein Q is $NR^8R^9$ and $R^8$ is H and $R^9$ is selected from phenyl or aromatic 5-9 membered heterocyclyl, wherein said phenyl or heterocyclyl is optionally substituted with 1-3 substituents selected from halo, nitro, cyano, and $C_{1-3}$ alkyl; or (y) or combinations of the above.

Examples of compounds of the invention include: 1-[4-(4-piperidin-1-ylmethyl-phenyl)-but-3-ynyl]-piperidine; 1-[3-(4-piperidin-1-yl-but-1-ynyl)-benzyl]-piperidine; 4-[3-(4-piperidin-1-yl-but-1-ynyl)-benzyl]-morpholine; 4-[3-(4-piperidin-1-yl-but-1-ynyl)-benzyl]-morpholine dihydrochloride; 1-[4-(4-pyrrolidin-1-yl-but-1-ynyl)-benzyl]-piperidine; diethyl-[4-(4-piperidin-1-ylmethyl-phenyl)-but-3-ynyl]-amine; 4-[4-(4-piperidin-1-ylmethyl-phenyl)-but-3-ynyl]-thiomorpholine; 4-[4-(4-piperidin-1-ylmethyl-phenyl)-but-3-ynyl]-morpholine; 1-methyl-4-[4-(4-piperidin-1-ylmethyl-phenyl)-but-3-ynyl]-piperazine; 1-[4-(4-pyrrolidin-1-ylmethyl-phenyl)-but-3-ynyl]-piperidine; 4-[4-(4-piperidin-1-yl-but-1-ynyl)-benzyl]-morpholine; diethyl-[4-(4-piperidin-1-yl-but-1-ynyl)-benzyl]-amine; 1-{4-[4-(4-benzyl-piperidin-1-ylmethyl)-phenyl]-but-3-ynyl}-piperidine; 1-[4-(4-piperidin-1-yl-but-1-ynyl)-benzyl]-piperidin-4-ol; 2-{1-[4-(4-piperidin-1-yl-but-1-ynyl)-benzyl]-piperidin-2-yl}-ethanol; 1-[4-(4-piperidin-1-yl-but-1-ynyl)-benzyl]-decahydro-quinoline; 1-[4-(4-piperidin-1-yl-but-1-ynyl)-benzyl]-piperidine-4-carboxylic acid amide; 8-[4-(4-piperidin-1-yl-but-1-ynyl)-benzyl]-1,4-dioxa-8-aza-spiro[4.5]decane; 1-methyl-4-[4-(4-piperidin-1-yl-but-1-ynyl)-benzyl]-piperazine; cyclohexyl-[4-(4-piperidin-1-yl-but-1-ynyl)-benzyl]-amine; indan-1-yl-[4-(4-piperidin-1-yl-but-1-ynyl)-benzyl]-amine; 1-phenyl-4-[4-(4-piperidin-1-yl-but-1-ynyl)-benzyl]-piperazine; 1-benzyl-4-[4-(4-piperidin-1-yl-but-1-ynyl)-benzyl]-piperazine; 4-[4-(4-piperidin-1-yl-but-1-ynyl)-benzyl]-piperazine-1-carboxylic acid tert-butyl ester; 1-[4-(4-piperidin-1-yl-but-1-ynyl)-benzyl]-piperazine; 1-isopropyl-4-[4-(4-piperidin-1-yl-but-1-ynyl)-benzyl]-piperazine; 1-phenyl-8-[3-(4-piperidin-1-yl-but-1-ynyl)-benzyl]-1,3,8-triaza-spiro[4.5]decan-4-one; 1-[3-(4-piperidin-1-yl-but-1-ynyl)-benzyl]-piperidine-3-carboxylic acid diethylamide; 1-[3-(4-piperidin-1-yl-but-1-ynyl)-benzyl]-1,2,3,4,5,6-hexahydro-[2,3']bipyridinyl; 1-[3-(4-piperidin-1-yl-but-1-ynyl)-benzyl]-4-(3-trifluoromethyl-phenyl)-piperazine; 2-{4-[3-(4-piperidin-1-yl-but-1-ynyl)-benzyl]-piperazin-1-yl}-pyrimidine; 1-[3-(4-piperidin-1-yl-but-1-ynyl)-benzyl]-piperidine-4-carboxylic acid amide; methyl-[3-(4-piperidin-1-yl-but-1-ynyl)-benzyl]-(2-pyridin-2-yl-ethyl)-amine; [2-(3,4-dimethoxy-phenyl)-ethyl]-methyl-[3-(4-piperidin-1-yl-but-1-ynyl)-benzyl]-amine; 4-[3-(4-piperidin-1-yl-but-1-ynyl)-benzyl]-thiomorpholine; allyl-cyclopentyl-[3-(4-piperidin-1-yl-but-1-ynyl)-benzyl]-amine; 10-[3-(4-piperidin-1-yl-but-1-ynyl)-benzyl]-1,4,7-trioxa-10-aza-cyclododecane; 1-[4-(3-thiazolidin-3-ylmethyl-phenyl)-but-3-ynyl]-piperidine; [2-(1H-indol-3-yl)-ethyl]-methyl-[3-(4-piperidin-1-yl-but-1-ynyl)-benzyl]-amine; 1-{1-[3-(4-piperidin-1-yl-but-1-ynyl)-benzyl]-piperidin-4-yl}-1,3-dihydro-benzoimidazol-2-one; phenyl-[3-(4-piperidin-1-yl-but-1-ynyl)-benzyl]-amine; 1-[4-(3-pyrrolidin-1-ylmethyl-phenyl)-but-3-ynyl]-piperidine; 1-[3-(4-piperidin-1-yl-but-1-ynyl)-benzyl]-azacyclotridecane; dimethyl-[4-(4-piperidin-1-ylmethyl-phenyl)-but-3-ynyl]-amine; dimethyl-[4-(4-piperidin-1-yl-but-1-ynyl)-benzyl]-amine; phenyl-[4-(4-piperidin-1-yl-but-1-ynyl)-benzyl]-amine; 1-[4-(3-aziridin-1-ylmethyl-phenyl)-but-3-ynyl]-piperidine; 2-{1-[3-(4-piperidin-1-yl-but-1-ynyl)-benzyl]-piperidin-4-yloxy}-pyrimidine; {1-[3-(4-piperidin-1-yl-but-1-ynyl)-piperidin-4-yl}-pyridin-2-yl-amine; 4-[4-(3-morpholin-4-ylmethyl-phenyl)-but-3-ynyl]-morpholine; 4-[3-(4-thiomorpholin-4-yl-but-1-ynyl)-benzyl]-morpholine; 4-[3-(4-piperidin-1-yl-but-1-ynyl)-benzyl]-thiomorpholine; 4-[4-(3-thiomorpholin-4-ylmethyl-phenyl)-but-3-ynyl]-morpholine; 4-[3-(4-thiomorpholin-4-yl-but-1-ynyl)-benzyl]-thiomorpholine; 4-{4-[3-(4-methyl-piperazin-1-ylmethyl)-phenyl]-but-3-ynyl}-morpholine; 4-{4-[3-(4-methyl-piperazin-1-ylmethyl)-phenyl]-but-3-ynyl}-thiomorpholine; 1-methyl-4-[3-(4-piperidin-1-yl-but-1-ynyl)-benzyl]-piperazine; 1-[3-(4-piperidin-1-yl-but-1-ynyl)-benzyl]-piperidin-4-ol; 1-[3-(4-morpholin-4-yl-but-1-ynyl)-benzyl]-piperidin-4-ol; 1-[3-(4-thiomorpholin-4-yl-but-1-ynyl)-benzyl]-piperidin-4-ol; 1-{4-[3-(4-methoxy-piperidin-1-ylmethyl)-phenyl]-but-3-ynyl}-piperidine; 4-{4-[3-(4-methoxy-piperidin-1-ylmethyl)-phenyl]-but-3-ynyl}-morpholine; and 4-{4-[3-(4-methoxy-piperidin-1-ylmethyl)-phenyl]-but-3-ynyl}-thiomorpholine.

Additional compounds include: 1-[4-(4-piperidin-1-ylmethyl-phenyl)-but-3-ynyl]-piperidine; 1-[3-(4-piperidin-1-yl-but-1-ynyl)-benzyl]-piperidine; 4-[3-(4-piperidin-1-yl-but-1-ynyl)-benzyl]-morpholine; 4-[3-(4-piperidin-1-yl-but-1-ynyl)-benzyl]-morpholine dihydrochloride; 1-[4-(4- pyrrolidin-1-yl-but-1-ynyl)-benzyl]-piperidine; 1-[4-(4-pyrrolidin-1-ylmethyl-phenyl)-but-3-ynyl]-piperidine; diethyl-[4-(4-piperidin-1-yl-but-1-ynyl)-benzyl]-amine; 1-[4-(4-piperidin-1-yl-but-1-ynyl)-benzyl]-piperidine-4-ol; 2-{1-[4-(4-piperidin-1-yl-but-1-ynyl)-benzyl]-piperidin-2-yl}-ethanol; 1-[4-(4-piperidin-1-yl-but-1-ynyl)-benzyl]-decahydro-quinoline; 1-[4-(4-piperidin-1-yl-but-1-ynyl)-benzyl]-piperidine-4-carboxylic acid amide; 8-[4-(4-piperidin-1-yl-but-1-ynyl)-benzyl]-1,4-dioxa-8-aza-spiro[4.5]decane; 1-methyl-4-[4-(4-piperidin-1-yl-but-1-ynyl)-benzyl]-piperazine; cyclohexyl-[4-(4-piperidin-1-yl-but-1-ynyl)-benzyl]-amine; indan-1-yl-[4-(4-piperidin-1-yl-but-1-ynyl)-benzyl]-amine; 1-[4-(4-piperidin-1-yl-but-1-ynyl)-benzyl]-piperazine; 1-isopropyl-4-[4-(4-piperidin-1-yl-but-1-ynyl)-benzyl]-piperazine; 1-phenyl-8-[3-(4-piperidin-1-yl-but-1-ynyl)-benzyl]-1,3,8-triaza-spiro[4.5]decan-4-one; 1-[3-(4-piperidin-1-yl-but-1-ynyl)-benzyl]-piperidine-4-carboxylic acid amide; 4-[3-(4-piperidin-1-yl-but-1-ynyl)-benzyl]-thiomorpholine; allyl-cyclopentyl-[3-(4-piperidin-1-yl-but-1-ynyl)-benzyl]-amine; 10-[3-(4-piperidin-1-yl-but-1-ynyl)-benzyl]-1,4,7-trioxa-10-aza-cyclododecane; 1-[4-(3-thiazolidin-3-ylmethyl-phenyl)-but-3-ynyl]-piperidine; [2-(1H-indol-3-yl)-ethyl]-methyl-[3-(4-piperidin-1-yl-but-1-ynyl)-benzyl]-amine; 1-{1-[3-(4-piperidin-1-yl-but-1-ynyl)-benzyl]-piperidin-4-yl}-1,3-dihydro-benzoimidazol-2-one; and 1-[4-(3-pyrrolidin-1-ylmethyl-phenyl)-but-3-ynyl]-piperidine.

More preferred compounds include: 4-[3-(4-piperidin-1-yl-but-1-ynyl)-benzyl]-morpholine and 4-[4-(4-piperidin-1-yl-but-1-ynyl)-benzyl]-morpholine; and particularly the former.

Additional examples of compounds include: 1-[3-(4-piperidin-1-yl-but-1-ynyl)-benzyl]-piperidine; 4-[3-(4-piperidin-1-yl-but-1-ynyl)-benzyl]-morpholine; 4-[3-(4-piperidin-1-yl-but-1-ynyl)-benzyl]-morpholine dihydrochloride; 1-phenyl-8-[3-(4-piperidin-1-yl-but-1-ynyl)-benzyl]-1,3,8-triaza-spiro[4.5]decan-4-one; 1-[3-(4-piperidin-1-yl-but-1-ynyl)-benzyl]-piperidine-3-carboxylic acid diethylamide; 1-[3-(4-piperidin-1-yl-but-1-ynyl)-benzyl]-1,2,3,4,5,6-hexahydro-[2,3']bipyridinyl; 1-[3-(4-piperidin-1-yl-but-1-ynyl)-benzyl]-4-(3-trifluoromethyl-phenyl)-piperazine; 2-{4-[3-(4-piperidin-1-yl-but-1-ynyl)-benzyl]-piperazin-1-yl}-pyrimidine; 1-[3-(4-piperidin-1-yl-but-1-ynyl)-benzyl]-piperidine-4-carboxylic acid amide; methyl-[3-(4-piperidin-1-yl-but-1-ynyl)-benzyl]-(2-pyridin-2-yl-ethyl)-amine; [2-(3,4-dimethoxy-phenyl)-ethyl]-methyl-[3-(4-piperidin-1-yl-but-1-ynyl)-benzyl]-amine; 4-[3-(4-piperidin-1-yl-but-1-ynyl)-benzyl]-thiomorpholine; allyl-cyclopentyl-[3-(4-piperidin-1-yl-but-1-ynyl)-benzyl]-amine; 10-[3-(4-piperidin-1-yl-but-1-ynyl)-benzyl]-1,4,7-trioxa-10-aza-cyclododecane; 1-[4-(3-thiazolidin-3-ylmethyl-phenyl)-but-3-ynyl]-piperidine; [2-(1H-indol-3-yl)-ethyl]-methyl-[3-(4-piperidin-1-yl-but-1-ynyl)-benzyl]-amine; 1-{1-[3-(4-piperidin-1-yl-but-1-ynyl)-benzyl]-piperidin-4-yl}-1,3-dihydro-benzoimidazol-2-one; phenyl-[3-(4-piperidin-1-yl-but-1-ynyl)-benzyl]-amine; 1-[4-(3-pyrrolidin-1-ylmethyl-phenyl)-but-3-ynyl]-piperidine; and 1-[3-(4-piperidin-1-yl-but-1-ynyl)-benzyl]-azacyclotridecane.

Further examples include: dimethyl-[4-(4-piperidin-1-yl-methyl-phenyl)-but-3-ynyl]-amine; dimethyl-[4-(4-piperidin-1-yl-but-1-ynyl)-benzyl]-amine; phenyl-[4-(4-piperidin-1-yl-but-1-ynyl)-benzyl]-amine; 1-[4-(3-aziridin-1-ylmethyl-phenyl)-but-3-ynyl]-piperidine; 2-{1-[3-(4-piperidin-1-yl-but-1-ynyl)-benzyl]-piperidin-4-yloxy}-pyrimidine; {1-[3-(4-piperidin-1-yl-but-1-ynyl)-benzyl]-piperidin-4-yl}-pyridin-2-yl-amine; 4-[4-(3-morpholin-4-ylmethyl-phenyl)-but-3-ynyl]-morpholine; 4-[3-(4-thiomorpholin-4-yl-but-1-ynyl)-benzyl]-morpholine; 4-[3-(4-piperidin-1-yl-but-1-ynyl)-benzyl]-thiomorpholine; 4-[4-(3-thiomorpholin-4-ylmethyl-phenyl)-but-3-ynyl]-morpholine; 4-[3-(4-thiomorpholin-4-yl-but-1-ynyl)-benzyl]-thiomorpholine; 4-{4-[3-(4-methyl-piperazin-1-ylmethyl)-phenyl]-but-3-ynyl}-morpholine; 4-{4-[3-(4-methyl-piperazin-1-ylmethyl)-phenyl]-but-3-ynyl}-thiomorpholine; 1-methyl-4-[3-(4-piperidin-1-yl-but-1-ynyl)-benzyl]-piperazine; 1-[3-(4-piperidin-1-yl-but-1-ynyl)-benzyl]-piperidin-4-ol; 1-[3-(4-morpholin-4-yl-but-1-ynyl)-benzyl]-piperidin-4-ol; 1-[3-(4-thiomorpholin-4-yl-but-1-ynyl)-benzyl]-piperidin-4-ol; 1-{4-[3-(4-methoxy-piperidin-1-ylmethyl)-phenyl]-but-3-ynyl}-piperidine; 4-{4-[3-(4-methoxy-piperidin-1-ylmethyl)-phenyl]-but-3-ynyl}-morpholine; and 4-{4-[3-(4-methoxy-piperidin-1-ylmethyl)-phenyl]-but-3-ynyl}-thiomorpholine.

The invention also provides compounds that are useful as synthetic intermediates of the compounds of the invention. Such compounds, which themselves may or may not have pharmaceutical activity, include those provided in the schemes and synthetic examples.

The invention also contemplates compounds isotopically-labelled to be detectable by positron emission tomography (PET) or single-photon emission computed tomography (SPECT) useful for studying $H_3$-mediated disorders.

During any of the processes for preparation of the compounds of the present invention, it may be necessary and/or desirable to protect sensitive or reactive groups on any of the molecules concerned. In addition, compounds of the invention may be modified by using protecting groups; such compounds, precursors, or prodrugs are also within the scope of the invention. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", $3^{rd}$ ed., John Wiley & Sons, 1999. The protecting groups may be removed at a convenient subsequent stage using methods known from the art.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl) ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3, 3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(Imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyidiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate (levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate(tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

Protection for 1,2- and 1,3-Diols

Cyclic Acetals and Ketals

Examples of cyclic acetals and ketals include methylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Silyl Derivatives

Examples of silyl derivatives include di-t-butylsilylene group, and 1,3-(1,1,3,3-tetraisopropyldisiloxanylidene) derivative.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of Amides Include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Examples of special NH protective groups include:

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-4-methoxybenzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl)mesityl]methylene, and N-(N',N'-dimethylaminomethylene).

Protection for the Carbonyl Group

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of cyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or —S-phenyl and O-methyl-S-2-(methylthio)ethyl.

Cyclic Monothio Acetals and Ketals

Examples of cyclic monothio acetals and ketals include 1,3-oxathiolanes.

Miscellaneous Derivatives

O-Substituted Cyanohydrins

Examples of O-substituted cyanohydrins include O-acetyl, O-trimethylsilyl, O-1-ethoxyethyl and O-tetrahydropyranyl.

Substituted Hydrazones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl)imidazoles, N,N'-dimethylimidazolidines, 2,3-dihydro-1,3-benzothiazoles, diethylamine adducts, and methylaluminum bis (2,6-di-t-butyl-4-methylphenoxide)(MAD)complex.

Monoprotection of Dicarbonyl Compounds

Selective Protection of α- and β-Diketones

Examples of selective protection of α- and β-diketones include enamines, enol acetates, enol ethers, methyl, ethyl, i-butyl, piperidinyl, morpholinyl, 4-methyl-1,3-dioxolanyl, pyrrolidinyl, benzyl, S-butyl, and trimethylsilyl.

Cyclic Ketals, Monothio and Dithio Ketals

Examples of cyclic ketals, monothio and dithio ketals include bismethylenedioxy derivatives and tetramethylbismethylenedioxy derivatives.

Protection for the Carboxyl Group

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6- dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

Amides and Hydrazides

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl.

The compounds of the invention can be prepared according to the methods described in the next section.

C. Synthesis

The compounds of the invention can be prepared according to traditional synthetic organic methods and matrix or combinatorial chemistry methods, as shown in Schemes 1-5 below and in Examples 1-76. A person of ordinary skill will be aware of variations and adaptations of the schemes and examples provided to achieve the compounds of the invention.

One skilled in the art will recognize that synthesis of the compounds of the present invention may be effected by purchasing intermediate or protected intermediate compounds described in any of the Schemes disclosed herein. Throughout the schemes when the reacting functionality is located at $R^3$, one skilled in the art will recognize that the choice of $R^3$ is illustrative only and that the reacting functionality could also be located at $R^4$ and $R^5$ also.

One skilled in the art will further recognize that during any of the processes for preparation of the compounds of the present invention, it may be necessary and/or desirable to protect sensitive or reactive groups on any of the molecules concerned. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", John Wiley & Sons, 1991. The protecting groups may be removed at a convenient subsequent stage using methods known from the art.

Throughout the schemes when the reacting functionality is located at $R^5$, one skilled in the art will recognize that the choice of $R^5$ is illustrative only and that the reacting functionality could also be located at $R^3$ and/or $R^4$.

Compounds of formula (V) may be prepared according to the processes outlined in Scheme 1.

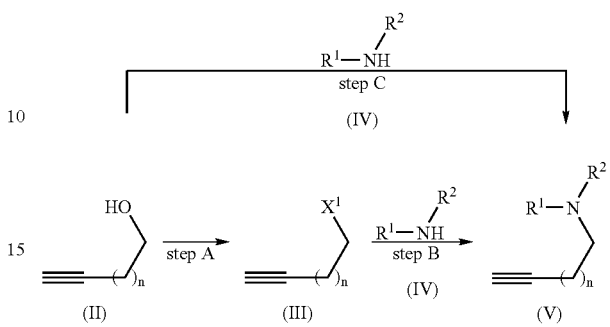

A compound of formula (V) is prepared as outlined in Scheme 1 from a compound of formula (II). A compound of formula (II) is reacted with a reagent capable of converting a hydroxyl function into a leaving group $X^1$ under hydroxyl activation conditions.

Leaving group $X^1$ is a suitable leaving group in a nucleophilic substitution reaction with an amine, such as amine $R^1R^2NH$. In a preferred embodiment, leaving group $X^1$ is a sulfonate ester, obtained by reacting a compound of formula (III) with an alkyl or arylsulfonyl chloride in a non-acoholic solvent in the presence of an organic or inorganic base at temperature from −78° C. to 50° C. Examples of such solvent are benzene, DCM, DCE, THF, DMF, acetonitrile, hexamethylphosphoramide (HMPA), hexane, pentane, and mixtures thereof. Examples of organic bases are pyridine, TEA, and mixtures thereof. Examples of inorganic bases are, KOH, NaOH, $Na_2CO_3$, $K_2CO_3$ or mixtures thereof.

In a particularly preferred embodiment, a compound of formula (II) is reacted with p-toluenesulfonyl chloride or methanesulfonyl chloride in DCM in the presence of TEA at a temperature between 0° C. and room temperature.

A compound of formula (V) is obtained from a compound of formula (III) by reacting a compound of formula (IV) with a compound of formula (III) under nucleophilic displacement conditions, either neat or in a solvent in the presence or absence of a base at a temperature from 0° C. to 100° C. Examples of such solvent are methanol, ethanol, propanol, n-butanol, DMF, DMSO, DME, and compatible mixtures thereof. Examples of such base, when present, are sodium carbonate, potassium carbonate, cesium carbonate, triethylamine, tetramethylguanidine, and compatible mixtures thereof.

The use of a high polarity solvent may increase the rate and reduce by-product formation in these reactions. Such high polarity solvent is provided in some embodiments as a mixture of a first solvent with a cosolvent that increases the dielectric constant of the mixture with respect to the dielectric constant of such first solvent. For example, one of ordinary skill in the art will recognize in light of this disclosure that the use of water as such cosolvent may increase the rate and reduce by-product formation in these reactions. In a preferred embodiment the solvent is water, ethanol, or a mixture of water and ethanol and/or propanol, the base is sodium or potassium carbonate or absent, and the temperature is room temperature to 80° C.

In a particularly preferred embodiment, the solvent is ethanol, no exogenous base is used, and the temperature is 0° C. to room temperature.

A compound of formula (V) may also be obtained from a compound of formula (II) by reaction of a compound of formula (IV) in the presence of a trialkylphosphonium halide, such as (cyanomethyl)trimethylphosphonium iodide and a base such as DIPEA in a solvent such as propionitrile at 90° C.

Compounds of formula (I) may be prepared according to the processes outlined in Scheme 2.

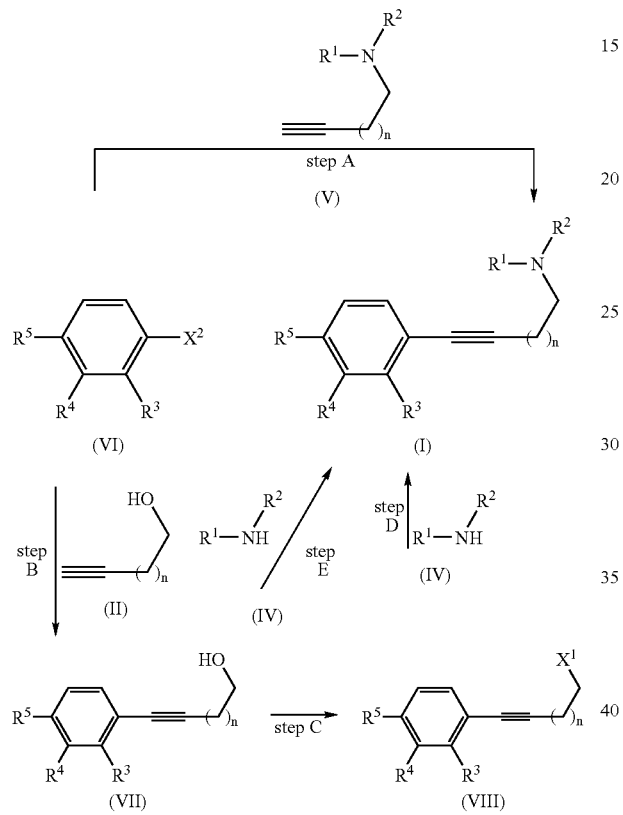

A compound of formula (I) is prepared from a compound of formula (VI) as shown in Scheme 2.

Group $X^2$, such as group $X^2$ in compound (VI), denotes a suitable leaving group for a coupling reaction with an alkyne, wherein "alkyne" in this definition refers to a chain, whether substituted or unsubstituted, that has a triple carbon-carbon bond. Examples of such leaving group include halo, such as iodo, bromo, and chloro, and sulfonate, such as trifluoromethanesulfonate. A compound of formula (VI) is reacted with a compound of formula (II) under Sonogashira conditions in the presence of a palladium-containing catalyst, such as palladium on carbon, $Pd(PPh_3)_2Cl_2$, $Pd_2(dba)_3$, $Pd_2(dba)_3 \cdot CHCl_3$, $Pd(P^tBu_3)_2$, $Pd_2(dba)_3 \cdot CHCl_3/Pd(P^tBu_3)_2$, $Pd(OAc)_2$, $Pd(PhCN)_2Cl_2$, and $PdCl_2$, and a base, such as triethylamine, DIEA, di-iso-propylamine, sodium carbonate, potassium carbonate, cesium carbonate, and mixtures thereof in a solvent such as THF, DME, dioxane, DCE, DCM, toluene, acetonitrile, and mixtures thereof at a temperature from 0° C. to 100° C.

A copper compound is used as a catalyst in this reaction, such as Cu(I) compound. Such Cu(I) catalyst is preferably incorporated in the reaction medium as substoichiometric quantities of a copper salt, such as CuI or $CuBrMe_2S$. The use of phosphine ligands, such as $PPh_3$ or $P(^tBu)_3$, is part fo the methodology of some embodiments of the present invention.

As in other process steps in the context of embodiments of this invention, the use of a high polarity solvent may increase the rate and reduce by-product formation in these reactions. Such high polarity solvent is provided in some embodiments as a mixture of a first solvent with a cosolvent that increases the dielectric constant of the mixture with respect to the dielectric constant of such first solvent. For example, one of ordinary skill in the art will recognize in light of this disclosure that the use of water as such cosolvent may increase the rate and reduce by-product formation in these reactions.

In a preferred embodiment, the palladium source is $Pd_2(dba)_3 \cdot CHCl_3/Pd(P^tBu_3)_2$, $Pd(PPh_3)_2Cl_2$, or palladium on carbon, the base is triethylamine or potassium carbonate, the solvent is THF, or a mixture of DME and water, and the temperature is between room temperature and 80° C. In a particularly preferred embodiment, the palladium source is $Pd(PPh_3)_2Cl_2$, the base is triethylamine, the solvent is THF, a catalytic quantity of CuI or $CuBrMe_2S$ is used, and the reaction temperature is room temperature to reflux temperature.

A compound of formula (I) is obtained from a compound of formula (VII) in analogy with Scheme 1, steps A and B, or by analogy with Scheme 1 step C. A compound of formula (I) may also be obtained directly from a compound of formula (VI) by reaction with a compound of formula (V) under Sonogashira conditions.

Compounds of formula (XII) may be prepared according to the processes outlined in Scheme 3.

Scheme 3

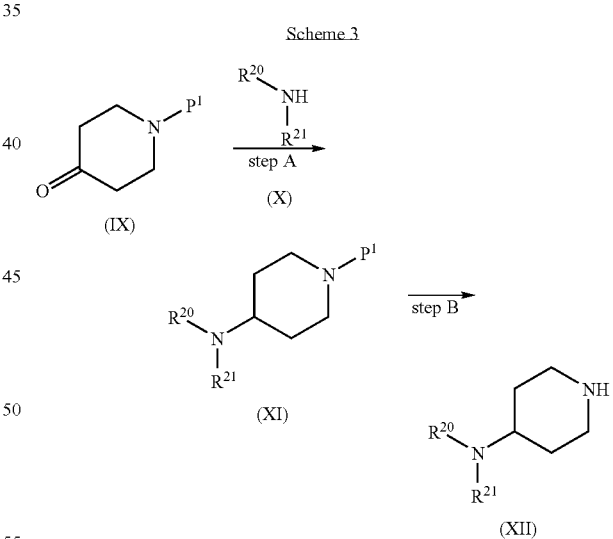

A compound of formula (XII) is prepared as outlined in Scheme 3 from a compound of formula (IX). One skilled in the art will be capable of selecting a suitable protecting group $P^1$ for the compound of formula (IX). A compound of formula (IX) is reacted with a compound of formula (X) under reductive amination conditions in the presence of a reducing agent such as $NaBH(OAc)_3$ in a solvent such as DCE, THF, and mixtures thereof at a temperature from 0° C. to 80° C. Amine (X) reacts in this reductive amination with aldehyde (IX) to form an iminium ion. According to this disclosure, one skilled in the art will recognize that the addition of an acid, such as acetic acid, may accelerate this reaction and decrease byproduct formation. The iminium ion thus formed is subsequently reduced by NaBH(OAc)$_3$ to the desired product. In a particularly preferred embodiment, a compound of formula (IX) is reacted with a compound of formula (X) in the presence of NaBH(OAc)$_3$ and acetic acid in DCE at room temperature.

A compound of formula (XII) is obtained from a compound of formula (XI) by removal of the protecting P$^1$ under conditions familiar to one skilled in the art. Selection and removal of protecting group P$^1$ is within the ordinary skill in the art in light of, for example, reference material cited herein (for example, works by Greene, et al., and McOmie), and description of protecing groups provided herein.

Compounds of formula (XVI) may be prepared according to the processes outlined in Scheme 4.

Scheme 4

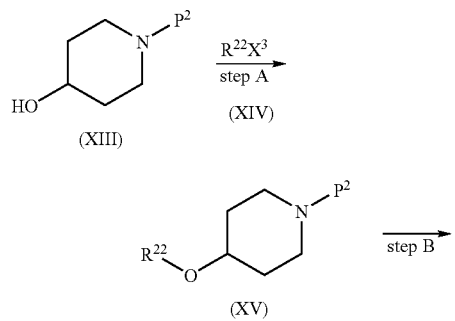

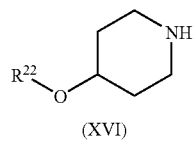
(XVI)

A compound of formula (XVI) is prepared as outlined in Scheme 4 from a compound of formula (XIII). As noted above, one skilled in the art will be capable of selecting a suitable protecting group P$^2$ for the compound of formula (XIII).

A compound of formula (XIII) is reacted with a compound of formula (XIV), where X$^3$ is a leaving group such a halogen or an activated ester, in the presence of a base, such as sodium hydride, potassium hydride, sodium hydroxide, potassium hydroxide, DBU, triethylamine, and butyllithium in a solvent such as DMF, THF, toluene, DMAC, acetonitrile, and mixtures thereof, at a temperature from room temperature to 140° C.

Alternatively, a compound of formula (XIII) is reacted with a compound of formula (XIV), where X$^3$ is hydroxyl and R$^{22}$ is an aromatic group, under Mitsunobu conditions. A compound of formula (XVI) is obtained from a compound of formula (XV) by removal of the protecting P$^2$ under conditions familiar to one skilled in the art.

Compounds of formula (XXVI) may be prepared according to the processes outlined in Scheme 5.

Scheme 5

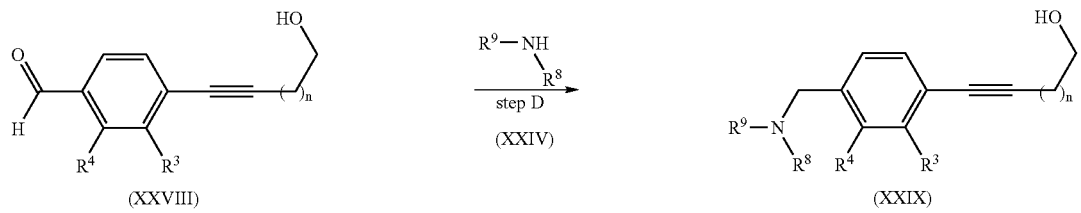

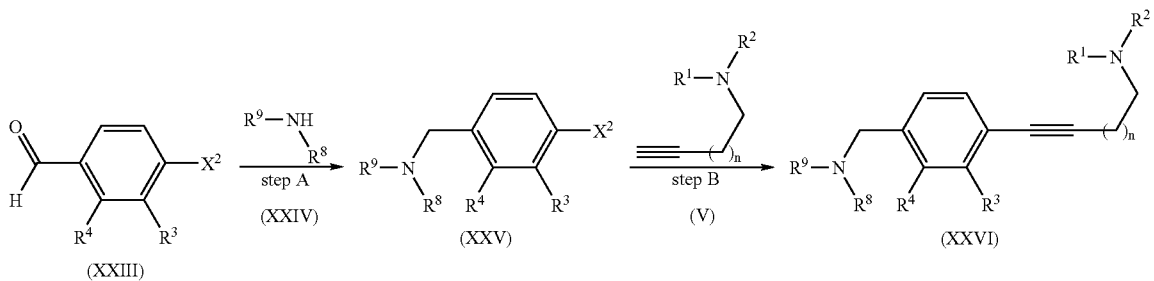

-continued

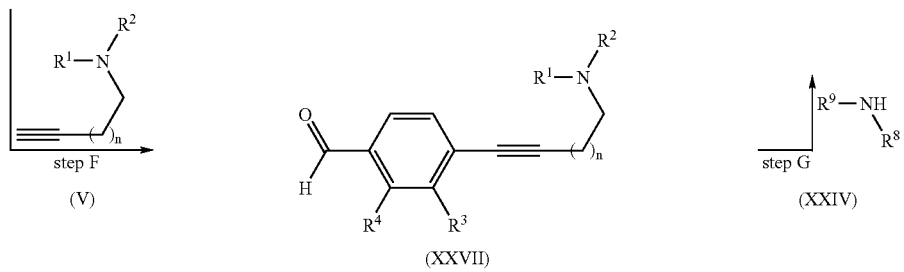

A compound of formula (XXVI) is prepared from a compound of formula (XXIII) as outlined in Scheme 5. The group $X^2$ in the compound of formula (XXIII) denotes a leaving group, as defined in Scheme 2.

A compound of formula (XXVIII) is obtained by reacting a compound of formula (XXIII) with a compound of formula (II) under Sonogashira conditions, as outlined in Scheme 2, step A. A compound of formula (XXIX) is obtained by reacting a compound of formula (XXVIII) with a compound of formula (XXIV) under reductive amination conditions as outlined in Scheme 3, step A. One skilled in the art will recognize that a substituted or unsubstituted nonaromatic heterocycle containing secondary amine functionality, for example piperidine derivatives, such as compounds (XII) and (XVI), may be used in place of the compound of formula (XXIV).

A compound of formula (XXVI) is obtained by reacting a compound of formula (XXIX) under the conditions described in Scheme 1, step C, or Scheme 1, steps A and B. Alternatively, compound of formula (XXVI) is obtained by reacting a compound of formula (XXV) with a compound of formula (V) under Sonogashira conditions, as described in Scheme 2, step A. Compound of formula (XXV) is obtained by reacting a compound of formula (XXIII) under reductive amination conditions, as described in Scheme 3, step A. Alternatively, compound of formula (XXVI) is obtained by reacting a compound of formula (XXVII) with a compound of formula (XXIV) under reductive amination conditions, as described in Scheme 3, step A. Compound of formula (XXVII) is obtained by reacting a compound of formula (XXIII) with a compound of formula (V) under Sonogashira conditions, as described in Scheme 2, step A.

Substituent $X^2$ and the aldehyde group are shown in a p-arrangement with respect to each other in compound (XXIII). Other schemes similar to Scheme 5 with substituent $X^2$ and the aldehyde group in arrangements o- and m- with respect to each other are not shown explicitly in the form of additional schemes. It is understood in light of the description provided herein that embodiments of this invention include schemes in which compound (XXIII) is analogous to that shown in Scheme 5 with substituent $X^2$ and the aldehyde group in o-arrangement with respect to each other. Similarly, it is also understood that embodiments of this invention include schemes in which compound (XXIII) is analogous to that shown in Scheme 5 with substituent $X^2$ and the aldehyde group in m-arrangement with respect to each other. Specific examples with such m-arrangement are provided herein because of the different reactivity under m-substitution conditions as compared with those under o- and p-substitution conditions.

Examples of additional embodiments of compound (XXIII) with various types of subsitutional arrangements are illustrated by suitably substituted formulae (XXIIIw), (XXIIIow), and (XXIIImw):

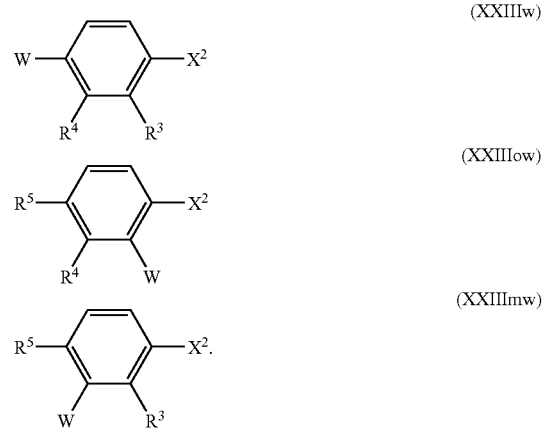

In addition to the methods of making the compounds of this invention that are described herein as implemented in light of the present disclosure and the ordinary skill in the art, embodiments of methods of making compounds according to this invention include the following.

Some embodiments include methods of making compounds of formula (I), a pharmaceutically acceptable salt, ester, or amide thereof, comprising at least one of the steps: reacting a compound of formula (VI) with a compound of formula (V)

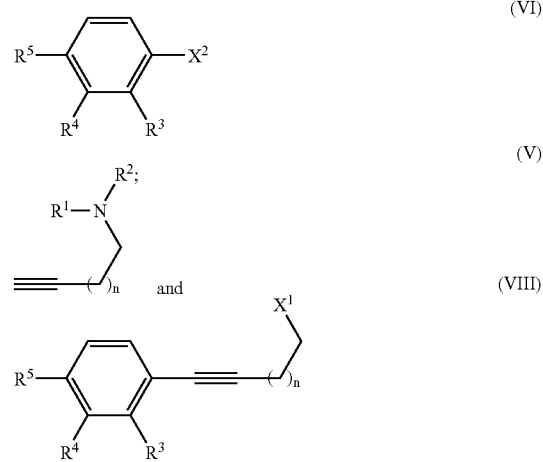

performing a nucleophilic substitution of $X_1$ in compound of formula (VIII) with an organic base $R^1R^2NH$, wherein $X^2$ is a suitable leaving group in a coupling reaction with an alkyne, and $X^1$ is a suitable leaving group in a nucleophilic substitution with an amine. More specifically, additional embodiments include those methods wherein $NR^1R^2$ taken together form piperidinyl, methylpiperidinyl, dimethylamino, pyrrolidinyl, diethylamino, methylethylamino, ethylpropylamino, or dipropylamino, more specifically, wherein $NR^1R^2$ taken together form piperidinyl, pyrrolidinyl, or diethylamino, and still more specifically, wherein $NR^1R^2$ taken together form piperidinyl or pyrrolidinyl. Additional embodiments include methods wherein one of $R^4$ and $R^5$ is G, more specifically, wherein $R^4$ is G, or wherein $R^5$ is G. Additional embodiments include methods wherein n is 1. Additional embodiments include methods wherein Q is a saturated N-linked nitrogen-containing heterocyclyl, more specifically, wherein Q is selected from substituted or unsubstituted piperidinyl, substituted or unsubstituted piperazinyl, pyrrolinyl, pyrrolidinyl, thiomorpholinyl, and morpholinyl; or wherein substituted Q is selected from N—($C_{1-6}$ alkyl) piperazinyl, N-phenyl-piperazinyl, 1,3,8-triaza-spiro[4.5]decyl, and 1,4-dioxa-8-aza-spiro[4.5]decyl; or wherein Q is a monovalent radical of an amine selected from aziridine, 1,4,7-trioxa-10-aza-cyclododecane, thiazolidine, 1-phenyl-1,3,8-triaza-spiro[4.5]decan-4-one, piperidine-3-carboxylic acid diethylamide, 1,2,3,4,5,6-hexahydro-[2,3']bipyridinyl, 4-(3-trifluoromethyl-phenyl)-piperazine, 2-piperazin-1-yl-pyrimidine, piperidine-4-carboxylic acid amide, methyl-(2-pyridin-2-yl-ethyl)-amine, [2-(3,4-dimethoxyphenyl)-ethyl]-methyl-amine, thiomorpholinyl, allyl-cyclopentyl-amine, [2-(1H-indol-3-yl)-ethyl]-methyl-amine, 1-piperidin-4-yl-1,3-dihydro-benzoimidazol-2-one, 2-(piperidin-4-yloxy)-pyrimidine, piperidin-4-yl-pyridin-2-ylamine, phenylamine, pyridin-2-ylamine; or wherein Q is selected from N-morpholinyl and N-piperidinyl, optionally substituted with between 1 and 3 substituents selected from hydroxyl, carboxamide, $C_{1-6}$ alkyl, 5-9 membered heterocyclyl, N($C_{1-6}$ alkyl)(5-9 membered heterocyclyl), NH(5-9 membered heterocyclyl), (5-9 membered heterocyclyl)$C_{1-3}$ alkylene, $C_{1-2}$-hydroxyalkylene, O(5-9 membered heterocyclyl), $C_{1-6}$ alkoxy, ($C_{3-6}$ cycloalkyl)-O—, phenyl, (phenyl)$C_{1-3}$ alkylene, and (phenyl)$C_{1-3}$ alkylene-O— where each of above heterocyclyl, phenyl, and alkyl groups may be optionally substituted with from 1 to 3 substituents independently selected from halo, nitro, cyano, and $C_{1-3}$ alkyl; or wherein Q is substituted with a substituent comprising a $C_{1-6}$ heterocyclyl group selected from: pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, and pyrrolyl, or more specifically wherein Q is a substituted or unsubstituted N-morpholinyl. Further embodiments include methods wherein n is 1;

$R^1$ and $R^2$ are independently selected from $C_2$ alkyl, or taken together with the nitrogen to which they are attached, they form a non-aromatic 5-6 membered heterocyclyl optionally including an additional heteroatom independently selected from O, S, and N;

one of $R^3$, $R^4$, and $R^5$ is G and the two remaining are H;

G is $L^2Q$;

$L^2$ is methylene;

Q is $NR^8R^9$ wherein $R^8$ is independently selected from hydrogen, $C_{1-2}$ alkyl, $C_3$ alkenyl, 6-9 membered carbocyclyl, 3-12 membered heterocyclyl, phenyl, (5-9-membered heterocyclyl)$C_2$ alkylene, and (phenyl) $C_2$ alkylene; and $R^9$ is independently selected from $C_{1-2}$ alkyl, $C_3$ alkenyl, 6-9 membered carbocyclyl, 3-12 membered heterocyclyl, phenyl, (5-9-membered heterocyclyl)$C_2$ alkylene, and (phenyl) $C_2$ alkylene;

or

Q is a saturated 3-13 membered N-linked heterocyclyl, wherein, in addition to the N-linking nitrogen, the 3-13 membered heterocyclyl may optionally contain between 1 and 3 additional heteroatoms selected from O, S, and N;

wherein each of the above alkyl, alkylene, alkenyl, alkenylene, heterocyclyl, and carbocyclyl groups may each be independently and optionally substituted with between 1 and 3 substituents selected from methoxy, halo, amino, nitro, hydroxyl, and $C_{1-3}$ alkyl;

and wherein substituents of Q can be further selected from tert-butyloxycarbonyl, carboxamide, 5-9-membered heterocyclyl, NH(6-membered heterocyclyl), O(6-membered heterocyclyl), phenyl, $C_2$-hydroxyalkylene, hydroxy, benzyl and, where each of above heterocyclyl, phenyl, and alkyl substituent groups of Q may be optionally substituted with trifluoromethyl.

Still other embodiments include methods wherein $NR^1R^2$ taken together form piperidinyl, pyrrolidinyl, or diethylamino, and Q is selected from substituted or unsubstituted piperidinyl, piperazinyl, pyrrolinyl, pyrrolidinyl, thiomorpholinyl, and morpholinyl; or wherein said organic base $R^1R^2NH$ is piperidine and said nucleophilic substitution is performed at room temperature; or wherein said nucleophilic substitution is performed at room temperature with 10 equivalents of piperidine in the presence of ethanol; or wherein said nucleophilic substitution is performed at room temperature with 10 equivalents of piperidine in the presence of ethanol and $X^1$ is mesylate, to yield a mixture of a substituted base and an elimination product; with or without further comprising exposing said mixture to HCl to yield a saline solution, selectively precipitating and crystallizing form said saline solution a phenylalkyne dihydrochloride salt; and a more particular embodiment being wherein said phenylalkyne dihydrochloride salt is 4-[3-(4-piperidin-1-yl-but-1-ynyl)-benzyl]morpholine dihydrochloride. Further embodiments include methods wherein any one of the following is satisfied:

$NR^1R^2$ taken together form piperidinyl or pyrrolidinyl, n is 1, and Q is selected from morpholinyl and piperidinyl;

$NR^1R^2$ taken together form piperidinyl or pyrrolidinyl, n is 1, and Q is morpholinyl or substituted morpholinyl;

n=1, $R^3$ is H, $R^5$ is H, $R^4$ is $L^2Q$, with Q being morpholinyl, $L^2$ as defined above, and $NR^1R^2$ taken together form piperidinyl;

said organic base $R^1R^2NH$ is piperidine;

said nucleophilic substitution is performed in the presence of ethanol at room temperature;

said nucleophilic substitution is performed in the presence of ethanol at room temperature and said organic base $R^1R^2$ NH is piperidine, including when the amount of said piperidine is 10 equivalents;

n=1, $R^3$ is H, $R^5$ is H, $R^4$ is $L^2Q$, with Q being morpholinyl, $L^2$ as defined above, said organic base $R^1R^2NH$ is piperidine, and said nucleophilic substitution is performed in the presence of ethanol at room temperature; said nucleophilic substitution yields a mixture of a substitution product and an elimination product and is performed in an alcoholic medium at a temperature such that said substitution product is obtained in at least 80%;

said nucleophilic substitution yields a mixture of a substitution product and an elimination product and is performed in the presence of ethanol at room temperature, and said organic base $R^1R^2NH$ is piperidine, further comprising treating said mixture with an acid to obtain a saline solution, and selectively precipitating and crystallizing said saline solution to obtain a salt, including any one of said acid being HCl, and diethyl ether and ethanol being used in said crystallization, in which latter case, a still more specific embodiment is characterized in that n=1, $R^3$ is H, $R^5$ is H, $R^4$ is $L^2Q$, with Q being morpholinyl, $L^2$ as defined above, and $NR^1R^2$ taken together form piperidinyl, said substitution product is 4-[3-(4-piperidin-1-yl-but-1-ynyl)-benzyl]-morpholine and said salt is the dihydrochloride salt of said substitution product. Other embodiments of methods wherein said nucleophilic substitution is performed in the presence of ethanol at room temperature and said organic base is $R^1R^2NH$ is piperidine, further comprise converting an alcohol of formula (VII) to said compound of formula (VIII), which more specifically can further comprise the reductive amination of a compound of formula (VIIa) with an amine $R^8R^9NH$, wherein one of $R^{3'}$, $R^{4'}$, and $R^{5'}$ is C(O)H and the other two are selected from H, chloro and bromo, to give a compound of formula (VII), wherein one of $R^3$, $R^4$, and $R^5$ is $NR^8R^9$ and the other two are selected from H, chloro and bromo,

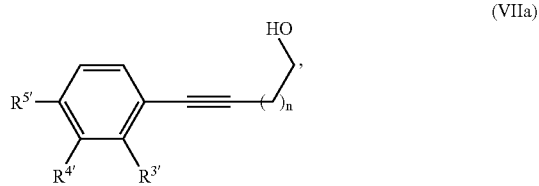

(VIIa)

and even more specifically methods wherein any one of the following is satisfied: said amine is morpholine; and further comprising the coupling in the presence of a palladium-containing catalyst and a copper salt of a compound of formula (II) with a disubstituted benzene, wherein one of said benzene substitutents is C(O)H and the other of said benzene substitutents is selected from chloro and bromo, to yield a compound of formula (VIIa).

Some embodiments include methods of making compounds of formula (I), a pharmaceutically acceptable salt, ester, or amide thereof, wherein more specifically one of $R^3$ and $R^5$ is G, one of the remaining and $R^4$ is H, and the other is selected from hydrogen, fluoro, and chloro, these embodiments comprising reacting at least one of the compounds of formulae (XXIIIw) and (XXIIIow) with a compound of formula (V)

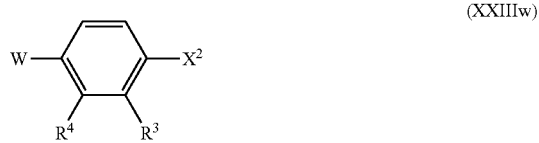

(XXIIIw)

-continued

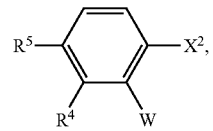

(XXIIIow)

wherein W is C(O)H or G, and $X^2$ is a suitable leaving group in a coupling reaction with an alkyne. More specifically, additional embodiments include methods wherein any one of the following is additionally satisfied:

said W is C(O)H, further comprising performing a reductive amination of said W with an organic base $R^9R^8NH$; $NR^1R^2$ taken together form piperidinyl, methylpiperidinyl, dimethylamino, pyrrolidinyl, diethylamino, methylethylamino, ethylpropylamino, or dipropylamino, including the more specific conditions wherein $NR^1R^2$ taken together form piperidinyl, pyrrolidinyl, or diethylamino, or wherein $NR^1R^2$ taken together form piperidinyl or pyrrolidinyl;

$R^5$ is G;

$R^3$ is G;

n is 1;

Q is a saturated N-linked nitrogen-containing heterocyclyl;

Q is selected from substituted or unsubstituted piperidinyl, substituted or unsubstituted piperazinyl, pyrrolinyl, pyrrolidinyl, thiomorpholinyl, and morpholinyl, including more specific characteristics such as any of wherein substituted Q is selected from N—($C_{1-6}$ alkyl)piperazinyl, N-phenyl-piperazinyl, 1,3,8-triaza-spiro[4.5]decyl, and 1,4-dioxa-8-aza-spiro[4.5]decyl, and wherein Q is a monovalent radical of an amine selected from aziridine, 1,4,7-trioxa-10-aza-cyclododecane, thiazolidine, 1-phenyl-1,3,8-triaza-spiro[4.5]decan-4-one, piperidine-3-carboxylic acid diethylamide, 1,2,3,4,5,6-hexahydro-[2,3']bipyridinyl, 4-(3-trifluoromethyl-phenyl)-piperazine, 2-piperazin-1-yl-pyrimidine, piperidine-4-carboxylic acid amide, methyl-(2-pyridin-2-yl-ethyl)-amine, [2-(3,4-dimethoxy-phenyl)-ethyl]-methyl-amine, thiomorpholinyl, allyl-cyclopentyl-amine, [2-(1H-indol-3-yl)-ethyl]-methyl-amine, 1-piperidin-4-yl-1,3-dihydro-benzoimidazol-2-one, 2-(piperidin-4-yloxy)-pyrimidine, piperidin-4-yl-pyridin-2-yl-amine, phenylamine, pyridin-2-ylamine; Q is selected from N-morpholinyl and N-piperidinyl, optionally substituted with between 1 and 3 substituents selected from hydroxyl, carboxamide, $C_{1-6}$ alkyl, 5-9 membered heterocyclyl, N($C_{1-6}$ alkyl)(5-9 membered heterocyclyl), NH(5-9 membered heterocyclyl), (5-9 membered heterocyclyl)$C_{1-3}$ alkylene, $C_{1-2}$-hydroxyalkylene, O(5-9 membered heterocyclyl), $C_{1-6}$ alkoxy, ($C_{3-6}$ cycloalkyl)-O—, phenyl, (phenyl)$C_{1-3}$ alkylene, and (phenyl)$C_{1-3}$ alkylene-O— where each of above heterocyclyl, phenyl, and alkyl groups may be optionally substituted with from 1 to 3 substituents independently selected from halo, nitro, cyano, and $C_{1-3}$ alkyl;

Q is substituted with a substituent comprising a $C_{1-6}$ heterocyclyl group selected from: pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, and pyrrolyl;

Q is a substituted or unsubstituted N-morpholinyl;

$NR^1R^2$ taken together form piperidinyl, pyrrolidinyl, or diethylamino, and Q is selected from substituted or unsubstituted piperidinyl, piperazinyl, pyrrolinyl, pyrrolidinyl, thiomorpholinyl, and morpholinyl;

$NR^1R^2$ taken together form piperidinyl or pyrrolidinyl, n is 1, and Q is selected from morpholinyl and piperidinyl;

$NR^1R^2$ taken together form piperidinyl or pyrrolidinyl, n is 1, and Q is morpholinyl or substituted morpholinyl;

n is 1, $R^4$ is H, one of $R^3$ and $R^5$ is H, the other one of $R^3$ and R is $L^2Q$, with Q being morpholinyl, and $L^2$ as defined above, and $NR^1R^2$ taken together form piperidinyl;

n is 1, $R^4$ is H, $R^3$ is H, $R^5$ is C(O)H, $NR^1R^2$ taken together form a piperidinyl, wherein said reacting is performed at room temperature;

n is 1, $R^4$ is H, $R^3$ is H, $R^5$ is C(O)H, $NR^1R^2$ taken together form a piperidinyl, wherein said reacting is performed at room temperature in the presence of a plaadadium-containing catalyst and a copper salt, and said reacting yields a phenylalkyne;

n is 1, $R^4$ is H, $R^3$ is H, $R^5$ is C(O)H, $NR^1R^2$ taken together form a piperidinyl, $X^2$ is bromo, wherein said reacting is performed at room temperature in the presence of a palladium-containing catalyst and a copper salt, and said reacting yields a phenylalkyne; and n is 1, $R^4$ is H, $R^3$ is H, $R^5$ is C(O)H, $NR^1R^2$ taken together form a piperidinyl, wherein said reacting is performed at room temperature in the presence of a plaadadium-containing catalyst and a copper salt, and said reacting yields a phenylalkyne, further comprising a reductive amination with $R^8R^9NH$ of said phenylalkyne to yield a base, with still more specific embodiments satisfying at least one of said $R^8R^9NH$ is morpholine and said base is 4-[4-(4-piperidin-1-yl-but-1-ynyl)-benzyl]-morpholine; and further comprising forming a saline solution with HCl, with even more specific embodiments further comprising obtaining a dihydrochloride salt of said base by crystallization, and still more specific embodiments satisfying that said base is 4-[4-(4-piperidin-1-yl-but-1-ynyl)-benzyl]-morpholine.

Still additional embodiments include methods wherein n is 1;

$R^1$ and $R^2$ are independently selected from $C_2$ alkyl, or taken together with the nitrogen to which they are attached, they form a non-aromatic 5-6 membered heterocyclyl optionally including an additional heteroatom independently selected from O, S, and N;

one of $R^3$ and $R^5$ is G, and the remaining and $R^4$ are H;

G is $L^2Q$;

$L^2$ is methylene;

Q is $NR^8R^9$ wherein $R^8$ is independently selected from hydrogen, $C_{1-2}$ alkyl, $C_3$ alkenyl, 6-9 membered carbocyclyl, 3-12 membered heterocyclyl, phenyl, (5-9-membered heterocyclyl)$C_2$ alkylene, and (phenyl) $C_2$ alkylene; and $R^9$ is independently selected from $C_{1-2}$ alkyl, $C_3$ alkenyl, 6-9 membered carbocyclyl, 3-12 membered heterocyclyl, phenyl, (5-9-membered heterocyclyl)$C_2$ alkylene, and (phenyl) $C_2$ alkylene;

or

Q is a saturated 3-13 membered N-linked heterocyclyl, wherein, in addition to the N-linking nitrogen, the 3-13 membered heterocyclyl may optionally contain between 1 and 3 additional heteroatoms selected from O, S, and N;

wherein each of the above alkyl, alkylene, alkenyl, alkenylene, heterocyclyl, and carbocyclyl groups may each be independently and optionally substituted with between 1 and 3 substituents selected from methoxy, halo, amino, nitro, hydroxyl, and $C_{1-3}$ alkyl;

and wherein substituents of Q can be further selected from tert-butyloxycarbonyl, carboxamide, 5-9-membered heterocyclyl, NH(6-membered heterocyclyl), O(6-membered heterocyclyl), phenyl, $C_2$-hydroxyalkylene, hydroxy, benzyl and, where each of above heterocyclyl, phenyl, and alkyl substituent groups of Q may be optionally substituted with trifluoromethyl.

Some embodiments include methods of making compounds of formula (I), a pharmaceutically acceptable salt, ester, or amide thereof, comprising reacting a compound of formula (VII)

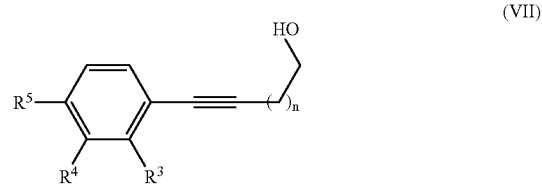

(VII)

with an organic base $R^1R^2NH$ in the presence of a trialkylphosphonium halide and a base. More specifically, additional embodiments include methods wherein any one of the following is satisfied:

said trialkylphosphonium halide is (cyanomethyl)trimethylphosphonium iodide, and said base is DIPEA;

$NR^1R^2$ taken together form piperidinyl, methylpiperidinyl, dimethylamino, pyrrolidinyl, diethylamino, methylethylamino, ethylpropylamino, or dipropylamino;

$NR^1R^2$ taken together form piperidinyl, pyrrolidinyl, or diethylamino;

$NR^1R^2$ taken together form piperidinyl or pyrrolidinyl;

one of $R^4$ and $R^5$ is G;

$R^4$ is G;

$R^5$ is G;

n is 1;

Q is a saturated N-linked nitrogen-containing heterocyclyl;

Q is selected from substituted or unsubstituted piperidinyl, substituted or unsubstituted piperazinyl, pyrrolinyl, pyrrolidinyl, thiomorpholinyl, and morpholinyl;

$NR^1R^2$ taken together form piperidinyl, pyrrolidinyl, or diethylamino, and Q is selected from substituted or unsubstituted piperidinyl, piperazinyl, pyrrolinyl, pyrrolidinyl, thiomorpholinyl, and morpholinyl;

$NR^1R^2$ taken together form piperidinyl or pyrrolidinyl, n is 1, and Q is selected from morpholinyl and piperidinyl;

$NR^1R^2$ taken together form piperidinyl or pyrrolidinyl, n is 1, and Q is morpholinyl or substituted morpholinyl; and n=1, $R^3$ is H, $R^5$ is H, $R^4$ is $L^2Q$, with Q being morpholinyl, $L^2$ as defined above, and $NR^1R^2$ taken together form piperidinyl.

Some embodiments include methods of making compounds of formula (I), a pharmaceutically acceptable salt, ester, or amide thereof, wherein more specifically $R^4$ is G, one of the remaining $R^3$ and $R^5$ is hydrogen, and the other is selected from hydrogen, fluoro, and chloro, these embodiments comprising reacting a compound of formula (XXII-lmw) with a compound of formula (V).

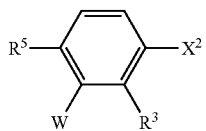

(XXIIImw)

wherein W is C(O)H or G, and $X^2$ is a suitable leaving group in a coupling reaction with an alkyne. More specifically, additional embodiments include methods wherein any one of the following is satisfied:

said W is C(O)H, further comprising performing a reductive amination of said W with an organic base $R^9R^8NH$;

$NR^1R^2$ taken together form piperidinyl, methylpiperidinyl, dimethylamino, pyrrolidinyl, diethylamino, methylethylamino, ethylpropylamino, or dipropylamino;

$NR^1R^2$ taken together form piperidinyl, pyrrolidinyl, or diethylamino;

$NR^1R^2$ taken together form piperidinyl or pyrrolidinyl;

n is 1;

Q is a saturated N-linked nitrogen-containing heterocyclyl;

Q is selected from substituted or unsubstituted piperidinyl, substituted or unsubstituted piperazinyl, pyrrolinyl, pyrrolidinyl, thiomorpholinyl, and morpholinyl;

substituted Q is selected from N—($C_{1-6}$ alkyl)piperazinyl, N-phenyl-piperazinyl, 1,3,8-triaza-spiro[4.5]decyl, and 1,4-dioxa-8-aza-spiro[4.5]decyl;

Q is a monovalent radical of an amine selected from aziridine, 1,4,7-trioxa-10-aza-cyclododecane, thiazolidine, 1-phenyl-1,3,8-triaza-spiro[4.5]decan-4-one, piperidine-3-carboxylic acid diethylamide, 1,2,3,4,5,6-hexahydro-[2,3']bipyridinyl, 4-(3-trifluoromethyl-phenyl)-piperazine, 2-piperazin-1-yl-pyrimidine, piperidine-4-carboxylic acid amide, methyl-(2-pyridin-2-yl-ethyl)-amine, [2-(3,4-dimethoxyphenyl)-ethyl]-methyl-amine, thiomorpholinyl, allyl-cyclopentyl-amine, [2-(1H-indol-3-yl)-ethyl]-methyl-amine, 1-piperidin-4-yl-1,3-dihydro-benzoimidazol-2-one, 2-(piperidin-4-yloxy)-pyrimidine, piperidin-4-yl-pyridin-2-yl-amine, phenylamine, pyridin-2-yl-amine;

Q is selected from N-morpholinyl and N-piperidinyl, optionally substituted with between 1 and 3 substituents selected from hydroxyl, carboxamide, $C_{1-6}$ alkyl, 5-9 membered heterocyclyl, N($C_{1-6}$ alkyl)(5-9 membered heterocyclyl), NH(5-9 membered heterocyclyl), (5-9 membered heterocyclyl)$C_{1-3}$ alkylene, $C_{1-2}$-hydroxyalkylene, O(5-9 membered heterocyclyl), $C_{1-6}$ alkoxy, ($C_{3-6}$ cycloalkyl)-O—, phenyl, (phenyl)$C_{1-3}$ alkylene, and (phenyl)$C_{1-3}$ alkylene-O— where each of above heterocyclyl, phenyl, and alkyl groups may be optionally substituted with from 1 to 3 substituents independently selected from halo, nitro, cyano, and $C_{1-3}$ alkyl;

Q is substituted with a substituent comprising a $C_{1-6}$ heterocyclyl group selected from: pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, and pyrrolyl;

Q is a substituted or unsubstituted N-morpholinyl;

$NR^1R^2$ taken together form piperidinyl, pyrrolidinyl, or diethylamino, and Q is selected from substituted or unsubstituted piperidinyl, piperazinyl, pyrrolinyl, pyrrolidinyl, thiomorpholinyl, and morpholinyl; and n is 1, $R^5$ is H, $R^3$ is H, and $R^4$ is $L^2Q$, with Q being morpholinyl, and $L^2$ as defined above, and $NR^1R$ taken together form piperidinyl.

Further embodiments include methods that satisfy:
n is 1;
$R^1$ and $R^2$ are independently selected from $C_2$ alkyl, or taken together with the nitrogen to which they are attached, they form a non-aromatic 5-6 membered heterocyclyl optionally including an additional heteroatom independently selected from O, S, and N;
$R^3$ and $R^5$ are H;
G is $L^2Q$;
$L^2$ is methylene;
Q is $NR^8R^9$ wherein $R^8$ is independently selected from hydrogen, $C_{1-2}$ alkyl, $C_3$ alkenyl, 6-9 membered carbocyclyl, 3-12 membered heterocyclyl, phenyl, (5-9-membered heterocyclyl)$C_2$ alkylene, and (phenyl) $C_2$ alkylene; and $R^9$ is independently selected from $C_{1-2}$ alkyl, $C_3$ alkenyl, 6-9 membered carbocyclyl, 3-12 membered heterocyclyl, phenyl, (5-9-membered heterocyclyl)$C_2$ alkylene, and (phenyl) $C_2$ alkylene;

or

Q is a saturated 3-13 membered N-linked heterocyclyl, wherein, in addition to the N-linking nitrogen, the 3-13 membered heterocyclyl may optionally contain between 1 and 3 additional heteroatoms selected from O, S, and N;
wherein each of the above alkyl, alkylene, alkenyl, alkenylene, heterocyclyl, and carbocyclyl groups may each be independently and optionally substituted with between 1 and 3 substituents selected from methoxy, halo, amino, nitro, hydroxyl, and $C_{1-3}$ alkyl;
and wherein substituents of Q can be further selected from tert-butyloxycarbonyl, carboxamide, 5-9-membered heterocyclyl, NH(6-membered heterocyclyl), O(6-membered heterocyclyl), phenyl, $C_2$-hydroxyalkylene, hydroxy, benzyl and, where each of above heterocyclyl, phenyl, and alkyl substituent groups of Q may be optionally substituted with trifluoromethyl.

Still additional embodiments satisfy $NR^1R^2$ taken together form piperidinyl or pyrrolidinyl, n is 1, and Q is selected from morpholinyl and piperidinyl, of which some embodiments more specifically satisfy $NR^1R^2$ taken together form piperidinyl or pyrrolidinyl, n is 1, and Q is morpholinyl or substituted morpholinyl. Still additional embodiments satisfy n is 1, $R^3$ is H, $R^5$ is H, W is C(O)H, and $X^2$ is choloro or bromo, and compound of formula (V) is 1-but-3-ynyl-piperidine, to form a phenylalkyne, of which some embodiments more specifically satisfy at least one of:

said reacting is performed in the presence of pyrrolidine and at a temperature of about 50° C. to form a phenylalkayne, with still some embodiments further satisfying wherein said reacting is performed in the presence of a palladium-containing catalyst and a copper salt;

$X^2$ is bromo, and said reacting is performed under conditions such that the yield of said phenylalkyne is at least 80%;

further comprising a reductive amination with $R^8R^9NH$ of said phenylalkyne to yield a base, with some more specific embodiments additionally satisfying at least one of:
wherein said $R^8R^9NH$ is morpholine and said base is 4-[3-(4-piperidin-1-yl-but-1-ynyl)-benzyl]-morpholine, and
further comprising forming a saline solution with HCl, of which embodiments some also further comprise obtaining a dihydrochloride salt of said base by crystallization, and some even more specifically satisfy said base being 4-[3-(4-piperidin-1-yl-but-1-ynyl)-benzyl]-morpholine.

Disclosed herein are linear synthetic paths such as those illustrated by embodiments of steps B, C, and D in Scheme 2, and by embodiments of steps B and E in Scheme 2. Additional illustrations of linear processes are provided by embodiments of steps C, D, and E in Scheme 5, and the combination of steps C and D in Scheme 5 and steps C and D in Scheme 2.

Disclosed herein are convergent synthetic paths such as those illustrated by embodiments of step A in Scheme 2. Additional illustrations of convergent processes are provided by embodiments of steps A and B in Scheme 5, and also by embodiments of steps F and G in Scheme 5.

Embodiments of processes according to this invention are particularly suited for the scale-up synthesis of compounds described herein and compounds related thereto that can be obtained on the basis of the teachings provided herein and the ordinary skill in the art. These related compounds include pharmaceutically acceptable salts, esters, and amides of compounds according to the present invention.

Conventional methodologies for nucleophilic substitutions yield unpractical low yields of the substitution product of interest, with yields of such product of about 50%, the remaining by-product being mainly a corresponding elimination product. An example of a substitution product of interest is the title compound in Example 16. An example of an elimination by-product is the following compound:

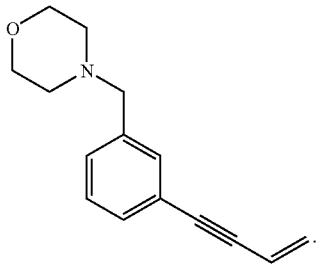

This elimination byproduct can be generated according to conventional methodology with a yield of as much as 50%. The following references provide background material on related conventional methodologies: Abdel-Magid, A. F., et al., *J. Org. Chem.* 1996, 61:3849-3862; Furst, A., *Helvetica Chemica Acta* 1947, 30:1454; and Kawai, S. H., et al., *J. Org. Chem.* 1994, 59:2620-2622. In contrast, methods according to the present invention permit the reduction in the formation of such elimination byproduct, so that its yield does not exceed 20%, and it was in some embodiments as low as 15%.

Relevant conventional methodologies that use palladium-containing catalysts and/or copper salts typically employ palladium-containing catalyst in amounts that range from about 1% to about 5% (both percentages given in terms of molar ratios). The following reference provides background material on related conventional methodologies: Sonogashera, K., et al., *Tetrahedron Letters* 1975, 50:4467-4470. In contrast, methods according to the present invention permit the reduction in the amount of palladium catalyst, so that its effective use was in some embodiments as low as 0.1% (also molar). This reduction in the amount of catalyst leads to a reduction in the production cost, an important consideration in scale-up processes. Furthermore, the less catalyst is used, the less likely it is that catalyst contamination will significantly propagate along the synthetic process. Purification along the process and/or purification of the final product is/are necessary when this contamination is significant.

Relevant conventional methodologies rely on chromatographic purification of the final product. In contrast, the methods according to the present invention, whether implemented in the form of linear or convergent embodiments, permit the purification of the final product by selective precipitation and/or crystallization. These techniques led to the obtention of final products with purity ranging from 95% to 99%, and they are much more suitable for scale-up synthetic processes than chromatographic purification. In light of the ordinary knowledge in crystallography, and in the absence of the disclosure provided herein, the crystallographic behavior of embodiments of compounds of the present invention is deemed unpredictable. As described herein, it has been found in the context of the present invention, that compounds of the present invention can be crystallized and that this technique can be implemented in their synthesis and purification.

Embodiments of convergent processes according to the present invention remove the production of elimination byproduct. High yields of final product were obtained in just a reduced number of synthetic steps. Embodiments of the present invention are illustrated by convergent methods that have at most three linear steps. Such reduction in the number of synthetic steps leads to an increase in efficiency.

Conventional methodologies that rely on Sonogashira coupling reaction procedures involving acetylenic amines generally give modest yields that are about 50%. Acetylenic compound dimerization leads to byproducts that contribute to such low yield in conventional practice. The following references provide background material on related conventional methodologies: Kano, H., et al., *J. Med. Chem.* 1967, 10(3):411-418; Vaillancourt, V. A., et al., WO 0202558 A1; Guzikowski, A. P., et al., *J. Med. Chem.* 2000, 43:984-994; Wright, J. L., et al., *J. Med. Chem.* 2000, 43:3408-3419. In contrast, methods according to the present invention increased such reactions yields to at least 80%, with actual yields ranging from about 86% (m-, or meta, substitution, in contrast with conventional yields of 25%-30% for the same substitution) to about 92% (o-, or orto, and p-, or para, substitution). The use of a strong base, such as pyrrolidine and temperature conditions, such as those described herein, facilitated high yields in the context of the present methods. Preferred temperature conditions include about room temperature (RT) when there is o- or p-substitution, and about 50° C. when there is m-substitution.

D. Formulation, Administration, and Therapy

The disclosed compounds, alone or in combination (with, for example, a histamine $H_1$ receptor antagonist), are useful for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof.

1. Formulation and Administration

The compounds or compositions of the invention may be formulated and administered to a subject by any conventional route of administration, including, but not limited to, intravenous, oral, subcutaneous, intramuscular, intradermal and parenteral administration. The quantity of the compound which is effective for treating each condition may vary, and can be determined by one of ordinary skill in the art.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The present invention also provides pharmaceutical compositions comprising one or more compounds of this invention in association with a pharmaceutically acceptable carrier and optionally additional pharmaceutical agents such as $H_1$ antagonists or SSRIs. Preferably these compositions are in unit dosage forms such as pills, tablets, caplets, capsules (each including immediate release, timed release and sustained release formulations), powders, granules, sterile parenteral solutions or suspensions (including syrups and emulsions), metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. Examples include 5 mg, 7 mg, 10 mg, 15 mg, 20 mg, 35 mg, 50 mg, 75 mg, 100 mg, 120 mg, 150 mg, and so on. The tablets or pills of the disclosed compositions can be coated or otherwise compounded to provide a dosage form affording the advantage of prolonged action. For example, the tablet or pill can comprise an inner dosage and an outer dosage component, the latter being in the form of an envelope over the former. The two components can be septed by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the compounds and compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolyl-ysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of ADHD is required.

The daily dosage of the products may be varied over a wide range from 1 to 1,000 mg per adult human per day. For oral administration, the compositions are preferably provided in the form of tablets containing 1.0, 5.0, 10.0, 15.0, 25.0, 50.0, 100, 250 and 500 milligrams of the active ingredient for the symptomatic adjustment of the dosage to the subject to be treated. An effective amount of the drug is ordinarily supplied at a dosage level of from about 0.01 mg/kg to about 20 mg/kg of body weight per day. Preferably, the range is from about 0.02 mg/kg to about 10 mg/kg of body weight per day, and especially from about 0.05 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

2. Combination Therapy

The disclosed compounds are useful in combination with other therapeutic agents, including $H_1$ receptor antagonists, $H_2$ receptor antagonists, and neurotransmitter modulators such as SSRIs and non-selective serotonin re-uptake inhibitors (NSSRIs).

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician, the delaying of which disorder is mediated, at least in part, by the modulation of one or more histamine receptors. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together. Combinations of three or more drugs are analogously possible. Methods of combination therapy include co-administration of a single formulation containing all active agents; essentially contemporaneous administration of more than one formulation; and administration of two or more active agents separately formulated.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. Whenever a yield is given as a percentage, such yield refers to a mass of the entity for which the yield is given with respect to the mamaximum amount of the same entity that could be obtained under the particular stoichiometric conditions.

E. EXAMPLES

Example 1

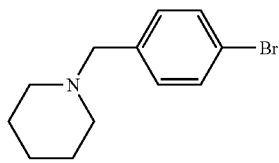

1-(4-Bromo-benzyl)-piperidine

A solution of 4-bromobenzaldehyde (5 g), piperidine (2.9 mL), and acetic acid (1.5 mL) in DCE (65 mL) was treated with sodium triacetoxyborohydride (6.9 g). After 27 h, the resulting mixture was treated with saturated aqueous sodium bicarbonate (50 mL), and extracted with DCM (2×50 mL). The combined organic phases were dried (magnesium sulfate) and evaporated. Kugelrohr distillation of the residue (160° C., 5 mm Hg) gave the title compound as a pale yellow oil (5.9 g).

Example 2

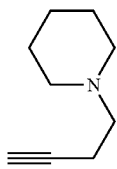

1-But-3-ynyl-piperidine

A solution of toluene-4-sulfonic acid but-3-ynyl ester (45.0 g) and piperidine (40 mL) in ethanol (70 mL) was treated with a solution of potassium carbonate (27.8 g) in water (70 mL). The mixture was heated to 80° C. for 2 h, cooled to RT, and extracted with DCM (3×100 mL). The combined organic phases were dried (magnesium sulfate), and evaporated. Distillation of the residue (110° C., 30 mm Hg) gave the title compound as a colorless oil (17.3 g).

Example 3

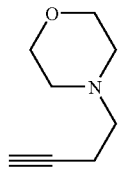

4-But-3-ynyl-morpholine

May be prepared analogously to Example 2 using morpholine.

Example 4

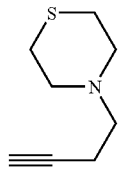

4-But-3-ynyl-thiomorpholine

May be prepared analogously to Example 2 using thiomorpholine.

Example 5

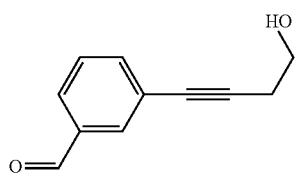

3-(4-Hydroxy-but-1-ynyl)-benzaldehyde

This is an example of a coupling reaction to form compounds such as the title compound by coupling compounds such as bromo benzaldehyde and 3-butyn-1-ol. A 1-L, 3-necked round-bottom flask was equipped with a magnetic stirring bar, a condenser with a nitrogen inlet, and two stoppers. The vessel was charged with 3-bromobenzaldehyde (18.5 g, 0.1 mol), 3-butyn-1-ol (10.5 g, 0.15 mol), triethylamine (100 mL), and THF (100 mL). To this mixture was then added $PdCl_2$ $(PPh_3)_2$ (1.4 g, 2 mmol) and $CuBrMe_2S$ (0.405 g, 4 mmol). In other examples, the title compound was also obtained by using CuI together with a palladium-containing entity. The reaction mixture was heated to reflux using a heating mantle. After 4 h when TLC (thin layer chromatography) showed complete consumption of the bromide, the mixture was allowed to cool to room temperature, transferred to a 1-L round-bottom flask and concentrated under reduced pressure. The residue was dissolved in 250 mL of ethyl acetate. The solution was washed with water and brine, dried over MgSO₄, and filtered. After filtration, the solvents were removed from the filtrate by evaporation under reduced pressure to obtain the title compound as pale yellow oil (16.8 g, yield 97%). Purity of the compound so obtained was determined by HPLC to be greater than 95%. TLC ($R_f$=0.32, SiO₂, ethyl acetate/hexanes, 1:1). MS (electro spray, positive mode), M⁺ 174. ¹H NMR (400 MHz, CDCl₃)δ: 2.72 (t, 2H, J=6.3), 3.84 (t, 2H, J=6.2), 7.47 (t, 1H, J=7.7), 7.66 (dt, 1H, J=7.7, 1.4), 7.81 (dt, 1H, J=7.7, 1.4), 7.91 (t, 1H, J=1.4), 9.98 (s, 1H). It was found in the context of this invention, as illustrated by the embodiment given in this example, that the amount of palladium catalyst can be reduced down to catalyst amounts in the order of 0.1% (mol/mol). In contrast, conventional methodologies rely on Pd catalyst amounts in the range 1%-5%, with the percentages referred to the same units. This reduction in the amount of palladium catalyst leads to a significant cost reduction. Furthermore, this reduction in the amount of palladium catalyst leads to a reduction in the palladium contamination of the final product.

Example 6

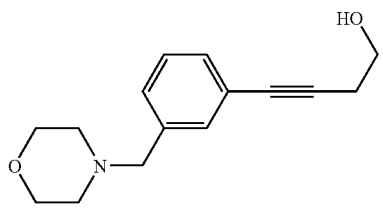

4-(3-Morpholin-4-ylmethyl-phenyl)-but-3-yn-1-ol

This is an example of a reductive amination to form compounds such as the title compound by reacting compounds such as an aldehyde and morpholine. A 1-L, 3-necked round-bottom flask was equipped with a mechanical stirrer, a rubber septum with a nitrogen inlet and a stopper. The flask was charged with the product of Example 5 (14.6 g, 0.0838 mol) and dichloromethane (250 mL). Morpholine (8.85 mL, 0.1 mol) was added, and then to this well-stirred reaction mixture was added sodium triacetoxyborohydride (32 g, 0.15 mol) in 4 equal portions. After the addition, the reaction mixture was stirred at room temperature overnight. Aqueous NaOH (10% w/v, 75 mL) was added, and the reaction mixture was transferred to a 1-L separatory funnel, to which water (100 mL) was then added. After separation of the layers, the aqueous phase was extracted once with dichloromethane (100 mL). The combined organic extracts were washed with brine (30 mL), dried over MgSO₄, and filtered. After filtration, the solvents were removed from the filtrate by evaporation under reduced pressure to yield the product as yellow oil (19 g with a 90% yield). Purity at this stage did not exceed 90% as determined by HPLC. The crude product was purified by filtration through a pad of silica gel (ethyl acetate/hexanes; 7:3) to obtain the title compound as a pale yellow oil (13.7 g). Purity of the product so obtained was greater than 98% as determined by HPLC (a degree of purity that is often referred to as "pure"). TLC ($R_f$=0.22, SiO₂, ethyl acetate/hexanes, 3:1). MS (electro spray, positive mode), (M⁺+H) 246. ¹H NMR (400 MHz, CDCl₃)δ: 2.43 (bt, 2H, J=4.4), 2.70 (t, 2H, J=6.2), 3.46 (s, 2H), 3.71 (t, 4H, J=4.6), 3.82 (t, 2H, J=6.2), 7.24-7.39 (m, 4H).

Example 7

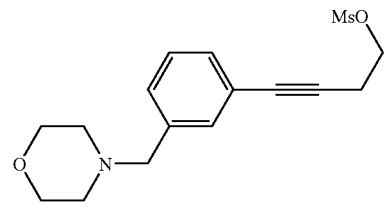

Methanesulfonic acid 4-(3-morpholin-4-ylmethyl-phenyl)-but-3-ynyl ester

This is an example of the conversion of compounds such as that illustrated in Example 6 to their methanesulfonate esters, as illustrated by the title compound. A 500-mL 1-necked round-bottom flask was equipped with a magnetic stirring bar and rubber septum with a nitrogen inlet. The vessel was charged with the product of Example 6 (13.6 g, 0.055 mol), dichloromethane (100 mL) and triethylamine (8.43 mL, 0.060 mol). The reaction mixture was cooled to 0° C. in an ice bath, and a solution of methanesulfonyl chloride (6.93 g) in dichloromethane (10 mL) was added in drops over 30 min. The cooling was removed and the reaction mixture was allowed to warm up to room temperature. After 1 h when TLC indicated complete conversion, 50 mL ice water was added, and the reaction mixture was transferred to a 500-mL separatory funnel. The organic extract was separated and washed with aqueous NaHCO₃, brine, and dried over MgSO₄. After filtration, the solvents were evaporated under reduced pressure (rotary evaporator, 30° C.) to obtain the title compound as pale yellow gum (17.5 g; yield 98%). Purity of the product so obtained was greater than 95% as determined by HPLC. TLC ($R_f$=0.27, SiO₂, ethyl acetate/hexanes, 3:1), MS (electro spray, positive mode), M⁺ 323. ¹H NMR (400 MHz, CDCl₃)δ: 2.3 (bt, 2H, J=4.4), 2.62 (t, 2H, J=6.2), 3.38 (s, 2H), 3.63 (t, 4H, J=4.6), 3.75 (t, 2H, J=6.2), 7.12-7.32 (m, 4H).

Example 8

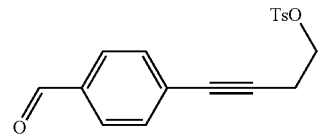

Toluene-4-sulfonic acid 4-(4-formyl-phenyl)-but-3-ynyl ester

A mixture of 4-bromobenzaldehyde (25.0 g), potassium carbonate (46.6 g), copper(1) iodide (1.0 g), triphenylphosphine (2.8 g), 10% palladium on carbon (288 mg) in water (250 mL) and DME (250 mL) was stirred at room temperature for 30 min, and 3-butyn-1-ol (25 mL) was added. The resulting mixture was heated at 90° C. for 16 h, cooled to room temperature, and filtered through a pad of Celite. The pad was washed with DCM (3×50 mL), and the filtrate was diluted with water (100 mL). The aqueous phase was extracted with ethyl acetate (2×400 mL), and the combined organic phases were washed with water (100 mL) and brine (100 mL), dried (magnesium sulfate), and concentrated under reduced pressure. The residue was azeotroped with toluene (2×100 mL) to give a brown solid (2.1 g). To a solution of this solid and triethylamine (7.1 mL) in DCM (100 mL) was added p-toluene sulfonyl chloride at 0° C. The resulting mixture was warmed to room temperature over a period of 2.5 h, diluted with water (10 mL), and extracted with DCM (2×300 mL). The combined organic phases were washed with water (2×40 mL) and brine (40 mL), and then dried (magnesium sulfate) and concentrated under reduced pressure. Chromatography of the residue (10-20% ethylacetate/hexane) gave the title compound as a yellow oil (6.7 g).

Example 9

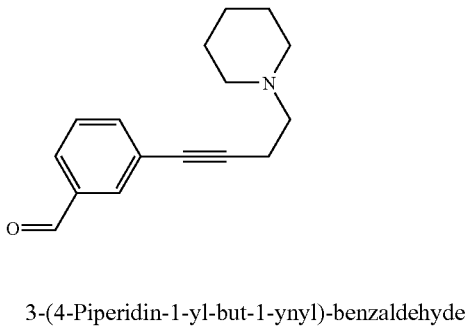

3-(4-Piperidin-1-yl-but-1-ynyl)-benzaldehyde

A mixture of 3-bromobenzaldehyde (0.58 mL), potassium carbonate (1.73 g), copper(1) iodide (38 mg), triphenylphosphine (105 mg), 10% palladium on carbon (220 mg) in water (10 mL) and DME (5 mL) was stirred at room temperature for 20 min, and treated with a solution of the product of Example 2 (1.7 g) in DME (5 mL). The resulting mixture was heated at 80° C. for 16 h, cooled to room temperature, and filtered through a pad of Celite. The pad was washed with DCM (5×20 mL), and the filtrate was diluted with water (30 mL). The aqueous phase was extracted with DCM (2×30 mL), and the combined organic phases were dried (magnesium sulfate) and concentrated under reduced pressure. Chromatography of the residue (0-3% 2 M methanolic ammonia/DCM) gave the title compound as a pale yellow oil (734 mg).

Example 10

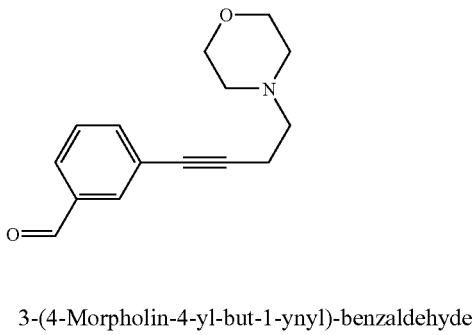

3-(4-Morpholin-4-yl-but-1-ynyl)-benzaldehyde

May be prepared analogously to Example 9 using the product of Example 3.

Example 11

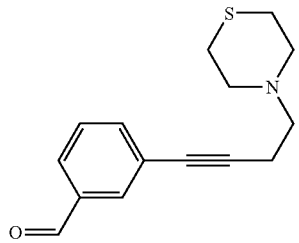

3-(4-Thiomorpholin-4-yl-but-1-ynyl)-benzaldehyde

May be prepared analogously to Example 9 using the product of Example 4.

Example 12

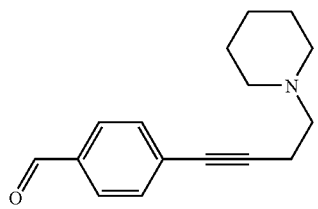

4-(4-Piperidin-1-yl-but-1-ynyl)-benzaldehyde

Method A: To a solution of the product of Example 8 (8.0 g) in 1-butanol (20 mL) was added piperidine (2.4 mL) followed by sodium carbonate (1.3 g) and potassium iodide (81 mg). The resulting mixture was heated at 80° C. for 16 h, cooled to room temperature, diluted with water (200 mL) and extracted with DCM (2×400 mL). The combined organic phases were washed with water (100 mL) and brine (100 mL), dried (magnesium sulfate), and concentrated under reduced pressure. Chromatography of the residue (6-8% 2 M methanolic ammonia/DCM) gave the title compound as a brown oil (4.6 g of a 1:1 mixture of the title compound and 1-[4-(4-Dibutoxymethyl-phenyl)-but-3-ynyl]-piperidine).

Method B: To a mixture of Pd(PPh$_3$)$_2$Cl$_2$ (0.57 g, 0.81 mmol, 0.01 equiv) and CuI (0.31 g, 1.6 mmol, 0.02 equiv), THF (180 mL) and Et$_3$N (90 mL, 0.64 mol, 8.0 equiv) were added under N$_2$. A stream of N$_2$ was bubbled through the solution for 15 min, and then 1-but-3-ynyl-piperidine (11.7 g, 85 mmol, 1.05 equiv) was added. The reaction mixture was stirred at room temperature for 16 h. A white precipitate (Et$_3$N.HBr) was collected by filtration and washed with EtOAc. The filtrate was concentrated under reduced pressure, and the resulting residue was re-dissolved in EtOAc. The EtOAc solution was washed with 1 M NaOH (aq) twice, dried over MgSO$_4$, and then poured directly onto a short pad of silica gel (neutralized with 5% Et$_3$N in hexanes), which was then washed with EtOAc. The filtrate was concentrated under reduced pressure to afford the product as a dark brown oil (18.1 g, 75 mmol, 92%), which was used without further purification (purity >95% by HPLC). MS (electrospray): mass calculated for C$_{16}$H$_{19}$ON, 241.1; m/z found, 242.2 [M+H]$^+$.

Example 12a

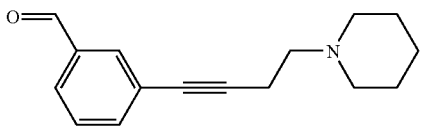

3-(4-Piperidin-1-yl-but-1-ynyl)-benzaldehyde

To the mixture of Pd(PPh$_3$)Cl$_2$ (24 mg, 0.034 mmol, 0.02 equiv.), CuI (13 mg, 0.068 mmol, 0.04 equiv.) and 3-bromobenzaldehyde (0.316 g, 1.7 mmol, 1 equiv.), pyrrolidine (10 mL) were added under N$_2$. The use of pyrrolidine is preferred in the context of this synthesis. A stream of N$_2$ was bubbled into to the solution for 5 min, and then 1-but-3-ynyl-piperidine (0.46 g, 3.3 mmol, 2 equiv.) was added. The reaction mixture was stirred at 50° C. for 40 h. This temperature is preferred in the context of this synthesis. On TLC and HPLC, the reaction was complete. The white precipitate (Et$_3$N.HBr) was filtered and washed with EtOAc. The solvent was evaporated and the residue was re-dissolved in EtOAc. The organic layer was washed with aqueous NaOH (1N) twice, and dried over MgSO$_4$. After filtration, the EtOAc solution was poured directly onto a short pad of silica gel (neutralized with 5% Et$_3$N in hexanes) and washed with EtOAc. The solvent was evaporated to afford the product as a brown oil (0.35 g, 1.45 mmol, 86%); purity >95% on HPLC; MS M+H$^+$ 242. This product does not need further purification in its use for subsequent steps in the context of this invention. A yield of 86% is in marked contrast with conventional methodologies, which produce the title compound with typical yields that do not exceed 30%.

Example 13

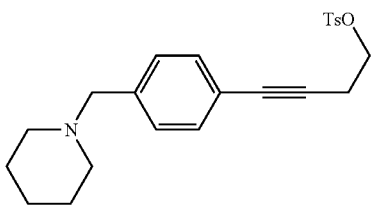

Toluene-4-sulfonic acid 4-(4-piperidin-1-ylmethyl-phenyl)-but-3-ynyl ester

A solution of the product of Example 8 (2.0 g), piperidine (0.91 mL), and acetic acid (0.42 mL) in DCM (100 mL) was treated with sodium triacetoxyborohydride (1.95 g) at room temperature. After 16 h, the resulting mixture was treated with 10% aqueous sodium hydroxide (30 mL). The aqueous phase was extracted with DCM (2×300 mL). The combined organic phases were dried (magnesium sulfate) and concentrated under reduced pressure. The residue was diluted in DCM (100 mL) and passed through a pad of silica gel. The pad was washed with DCM (3×200 mL). The combined filtrate was concentrated under reduced pressure, giving the title compound as a brown oil (2.3 g).

Example 14

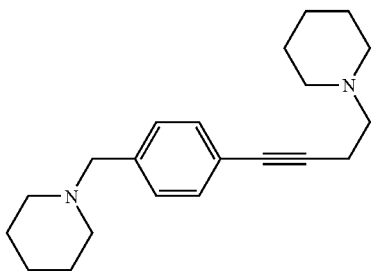

1-[4-(4-Piperidin-1-ylmethyl-phenyl)-but-3-ynyl]-piperidine $K_i$=1.6 nM

A mixture of the product of Example 1 (254 mg), potassium carbonate (346 mg), copper(1) iodide (7.6 mg), triphenylphosphine (21 mg), 10% palladium on carbon (43 mg) in water (2 mL) and DME (1 mL) was stirred at room temperature for 30 min, and treated with a solution of the product of Example 2 (343 mg) in DME (1 mL). The resulting mixture was heated at 80° C. for 16 h, cooled to room temperature, and filtered through a pad of Celite. The pad was washed with DCM (3×3 mL), and the filtrate was diluted with water (3 mL). The aqueous phase was extracted with DCM (2×3 mL), and the combined organic phases were dried (magnesium sulfate) and concentrated under reduced pressure. Chromatography of the residue (2.5%-5% 2 M methanolic ammonia/DCM) gave the title compound as a colorless oil (88 mg). $^1$H NMR (400 MHz, CDCl$_3$): 7.33 (d, J=7.4 Hz, 2H), 7.22 (d, J=7.8 Hz, 2H), 3.44 (s, 2H), 2.68-2.56 (m, 4H), 2.50-2.43 (m, 4H), 2.39-2.30 (m, 4H); 1.64-1.52 (m, 8H), 1.48-1.38 (m, 4H).

Example 15

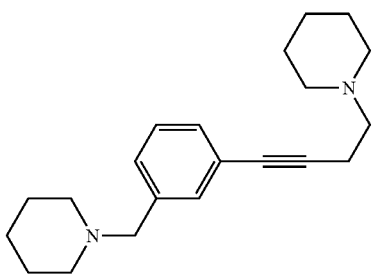

1-[3-(4-Piperidin-1-yl-but-1-ynyl)-benzyl]-piperidine $K_i$=0.8 nM

A solution of the product of Example 9 (193 mg) and piperidine (0.09 mL) in DCE (2 mL) was treated with sodium triacetoxyborohydride (254 mg). After 16 h, the resulting mixture was treated with 10% aqueous potassium hydroxide (2 mL), and extracted with DCM (2×3 mL). The combined organic phases were dried (magnesium sulfate) and concentrated under reduced pressure. Chromatography of the residue (0-8% 2 M methanolic ammonia/DCM) gave the title compound as a pale yellow oil (65 mg). ¹H NMR (400 MHz, CDCl₃): 7.35 (br s, 1H), 7.28-7.21 (m, 3H), 3.42 (s, 2H), 2.67-2.57 (m, 4H), 2.50-2.43 (m, 4H), 2.39-2.31 (m, 4H), 1.63-1.53 (m, 8H), 1.48-1.38 (m, 4H).

Example 16

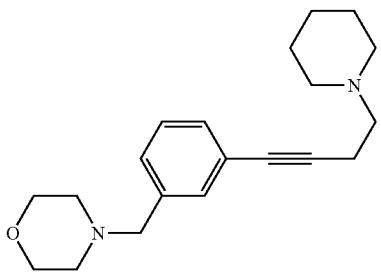

4-[3-(4-Piperidin-1-yl-but-1-ynyl)-benzyl]-morpholine $K_i$=0.8 nM

Method A: A solution of the product of Example 9 (193 mg) and morpholine (0.08 mL) in DCE (2 mL) was treated with sodium triacetoxyborohydride (254 mg). After 16 h, the resulting mixture was treated with 10% aqueous potassium hydroxide (2 mL), and extracted with DCM (2×3 mL). The combined organic phases were dried (magnesium sulfate) and concentrated under reduced pressure. Chromatography of the residue (0-8% 2 M methanolic ammonia/DCM) gave the title compound as a pale yellow oil (188 mg). ¹H NMR (400 MHz, CDCl₃): 7.36 (br s, 1H), 7.30-7.22 (m, 3H), 3.70 (t, J=4.6 Hz, 4H), 3.45 (s, 2H), 2.68-2.57 (m, 4H), 2.51-2.40 (m, 8H), 1.64-1.57 (m, 4H), 1.48-1.41 (m, 2H).

Method B: A 500-mL, 3-necked round-bottom flask was equipped with a magnetic stirring bar, an addition funnel, a thermometer, and a rubber septum with a nitrogen inlet. The vessel was charged with piperidine (54 mL, 46 g, 0.54 mol) and anhydrous ethanol (25 mL). The solution was cooled to 0° C. in an ice bath, and a solution of the product of Example 7 (17.5 g, 0.054 mol) in anhydrous ethanol (30 mL) was added. The ice bath was removed, and the reaction mixture was allowed to warm to room temperature. Room temperature is a preferred temperature condition. The amount of 10 mol equivalent piperidine in ethanol given here is a preferred amount. After 14 h when the reaction was judged complete by HPLC, the reaction mixture was transferred to a 500 mL round-bottom flask and concentrated under reduced pressure to dryness under reduced pressure. The residue was dissolved in CH₂Cl₂ (300 mL), washed with 5% aq. NaOH (75 mL), dried over MgSO₄, and filtered. After filtration, the filtrate was concentrated by solvent evaporation under reduced pressure to give an oil (20 g), which was determined by HPLC and ¹H NMR to contain an 85:15 mixture of the title compound and 4-(3-pent-4-en-1-ynyl-benzyl)-morpholine (this latter compound being the elimination compound in this reaction). This mixture does not need further purification in its use for subsequent steps in the context of this invention. TLC: title compound, ($R_f$=0.58, SiO₂, dichloromethane/0.02M NH₃ in MeOH, 9:1); 4-(3-pent-4-en-1-ynyl-benzyl)-morpholine, ($R_f$=0.38, SiO₂, ethyl acetate/hexanes, 3/1). MS (electro spray, positive mode), (M⁺+H) 313. ¹H NMR (400 MHz, CDCl₃) δ: 1.45 (bm, 2H), 1.62 (m, 4H), 2.41-2.48 (m, 8H), 2.62 (m, 4H), 3.44 (s, 2H), 3.71 (t, 4H, J=4.6), 7.22-7.36 (m, 4H).

Method C. 4-[3-(4-Piperidin-1-yl-but-1-ynyl)-benzyl]-morpholine: To the solution of 3-(4-Piperidin-1-yl-but-1-ynyl)-benzaldehyde (0.3 g, 1.24 mmol, 1 equiv.) in 20 mL dichloroethane, morpholine (0.13 g, 1.5 mmol, 1.2 equiv.) was added. To the well-stirred reaction mixture, NaHB (OAc)₃ (0.4 g, 1.8 mmol, 1.5 equiv.) was added at 0° C. under N₂. After addition, the cold bath was removed and the reaction mixture was stirred at room temperature for 1.5 h., when the reaction was judged complete by HPLC. Aqueous NaOH (1 N, 10 mL) was added slowly to quench the unreacted reagents. The organic layer was washed with NaOH aqueous solution (1 mol/L), dried over MgSO₄. After filtration, the solvent was evaporated under reduced pressure. The oily residue thus obtained was re-dissolved in EtOAc, and passed through a pad of silica gel (neutralized with 5% Et₃N in hexanes) and washed with EtOAc. Evaporation of the solvent afforded the product as a light yellow oil (0.36 g, 1.16 mmol, 93%). Purity >95% on HPLC. MS M+H⁺ 313.

Example 17

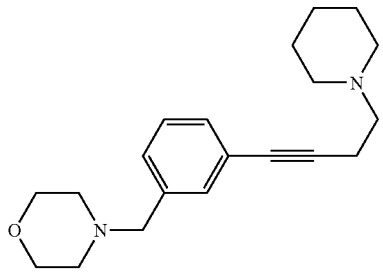

*2HCl

4-[3-(4-Piperidin-1-yl-but-1-ynyl)-benzyl]-morpholine dihydrochloride

Example of selective precipitation of compounds such as the title compound. A 3-L, 3-necked round-bottom flask was charged with the product of Example 16, Method B (77.0 g, 0.25 mol). To this was added absolute EtOH (385 mL). The reaction mixture was stirred and cooled to ~0° C. in an ice bath. HCl in dioxane (4 N, 126.5 mL) was added drop-wise over 0.5 h. The ice bath was removed, and the reaction mixture was stirred at room temperature for 2 h. The viscous reaction mixture was transferred to a 500 mL addition funnel and then added in a slow, steady stream to a 3-L, 3-necked round-bottom flask containing ether (500 mL), as the flask contents were stirred. The addition funnel was rinsed with absolute EtOH (115 mL), which was subsequently added to the ether solution. Ether (500 mL) was added via an addition funnel in a slow, steady stream. This resulted in the formation of a pale tan precipitate. The suspension was stirred at room temperature for 12 h. More ether (500 mL) was added, and the suspension was cooled to 0° C. and held at that temperature while stirred for 3 h. The product was collected by suction filtration using a medium porosity glass frit (filtration was slow). The filter cake was broken and washed with absolute EtOH/Et₂O (1:3, 2×75 mL). The product was dried under house vacuum and, subsequently, in a vacuum oven at 35° C. for 24 h. The dihydrochloride salt was obtained as an off-white powder (80.7 g). HPLC and $^1$H-NMR indicated the product to be >95% pure. At most, only trace amounts of the elimination product were present. A 2-L, 3-necked round-bottom flask equipped with an addition funnel, a reflux condenser and a mechanical stirrer was charged with the crude dihydrochloride salt (80.0 g). Absolute EtOH (160 mL) was added, and the resulting suspension was warmed to ~50° C. Ether (320 mL) was added in a slow stream via the addition funnel. Heating was discontinued, and the suspension slowly cooled to room temperature with stirring over ~4 h. The flask was cooled in an ice bath, stirred, and maintained at 0-5° C. for ~3 h. The precipitate was collected by suction filtration using a medium porosity glass frit (filtration was slow). The filter cake was broken and washed with cold EtOH/Et$_2$O (1:2, 2x75 mL). The product was dried in vacuo at 35° C. The title compound was obtained as an off white powder in an amount of 76.2 g, with a yield of 95%. MP 239° C. (decomp.). MS (electro spray, positive mode), (M$^+$+H) 313. $^1$H NMR (400 MHz, MeOH): 1.56 (bm, 1H), 1.82-1.85 (m, 3H), 1.96-1.99 (m, 2H), 2.99-3.07 (m, 4H), 3.17-3.24 (m, 2H), 3.30-3.41 (m, 6H), 3.62 (bd, J=12.7 Hz, 2H), 3.79 (bt, J=12.6 Hz, 2H), 4.01 (bd, J=12.5 Hz, 2H), 4.37 (s, 2H), 7.46-7.69 (m, 1H), 7.53-7.56 (m, 2H), 7.25 (m, 1H). Anal. Calcd. for C$_{20}$H$_{30}$N$_2$OCl$_2$: C, 62.33%; H, 7.85%; N, 7.27%; found: C, 62.13%; H, 7.52%; N, 7.23%. In contrast with conventional methodologies, the title compound was obtained with a high yield. Furthermore, and also in contrast with conventional methodologies, the title compound was obtained without the need of chromatographic purification.

Example 18

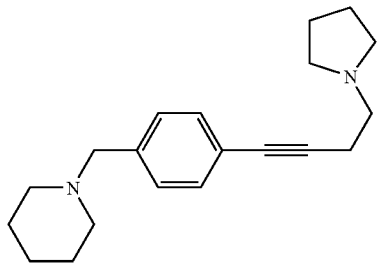

1-[4-(4-Pyrrolidin-1-yl-but-1-ynyl)-benzyl]-piperidine $K_i$=2.0 nM

A mixture of the product of Example 13 (199 mg), pyrrolidine (0.084 mL), and potassium carbonate (69 mg) in 1:1 ethanol/water (6 mL) was heated at 80° C. for 16 h. The resulting mixture was cooled to room temperature, diluted with water (10 mL), and extracted with DCM (2×100 mL). The combined organic phases were washed with water (20 mL) and brine (20 mL), dried (magnesium sulfate), and concentrated under reduced pressure. Chromatography of the residue (0-5% 2 M methanolic ammonia/DCM) gave the title compound as a pale yellow oil (60 mg). $^1$H NMR (400 MHz, CDCl$_3$): 7.33 (d, J=8.1 Hz, 2H), 7.23 (d, J=8.1 Hz, 2H), 3.44 (s, 2H), 2.78-2.73 (m, 2H), 2.64-2.57 (m, 6H), 2.35 (br s, 4H), 1.82-1.78 (m, 4H), 1.59-1.53 (m, 4H), 1.45-1.40 (m, 2H).

Example 19

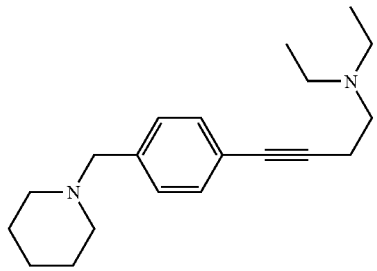

Diethyl-[4-(4-piperidin-1-ylmethyl-phenyl)-but-3-ynyl]-amine $K_i$=2.4 nM

A mixture of the product of Example 13 (199 mg), diethylamine (0.104 mL) and potassium carbonate (69 mg) in 1:1 ethanol/water (6 mL) was heated at 80° C. for 16 h. The resulting mixture was cooled to room temperature, diluted with water (10 mL), and extracted with DCM (2×100 mL). The combined organic phases were washed with water (20 mL) and brine (20 mL), dried (magnesium sulfate), and concentrated under reduced pressure. Chromatography of the residue (0-5% 2 M methanolic ammonia/DCM) gave the title compound as a pale yellow oil (21 mg). $^1$H NMR (400 MHz, CDCl$_3$): 7.33 (d, J=8.0 Hz, 2H), 7.23 (d, J=8.0 Hz, 2H), 3.44 (s, 2H), 2.81-2.73 (m, 2H), 2.64-2.51 (m, 6H), 2.35 (bs, 4H), 1.82-1.78 (m, 3H), 1.59-1.53 (m, 4H), 1.44-1.39 (m, 2H), 1.07 (t, J=7.2 Hz, 3H).

Example 20

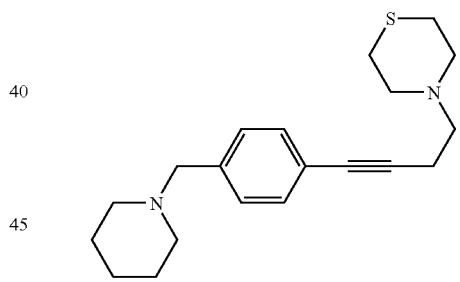

4-[4-(4-Piperidin-1-ylmethyl-phenyl)-but-3-ynyl]-thiomorpholine $K_i$=6.0 nM

A mixture of the product of Example 13 (199 mg), thiomorpholine (0.062 mL) and potassium carbonate (69 mg) in 1:1 ethanol/water (6 mL) was heated at 80° C. for 16 h. The resulting mixture was cooled to room temperature, diluted with water (10 mL) and extracted with DCM (2×100 mL). The combined organic phases were washed with water (20 mL) and brine (20 mL), dried (magnesium sulfate), and concentrated under reduced pressure. Chromatography of the residue (0-5% 2 M methanolic ammonia/DCM) gave the title compound as a pale yellow oil (27 mg). $^1$H NMR (400 MHz, CDCl$_3$): 7.32 (d, J=8.0 Hz, 2H), 7.23 (d, J=8.1 Hz, 2H), 3.44 (s, 2H), 2.83-2.80 (m, 4H), 2.74-2.68 (m, 6H), 2.59-2.55 (m, 2H), 2.35 (br s, 4H), 1.59-1.53 (m, 4H), 1.44-1.39 (m, 2H).

Example 21

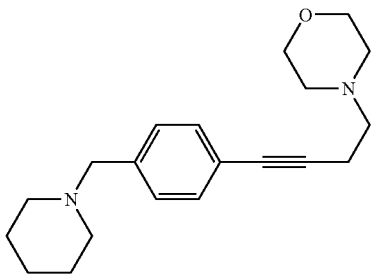

4-[4-(4-Piperidin-1-ylmethyl-phenyl)-but-3-ynyl]-morpholine $K_i$=15 nM

A mixture of the product of Example 13 (199 mg), morpholine (0.052 mL) and potassium carbonate (69 mg) in 1:1 ethanol/water (6 mL) was heated at 80° C. for 16 h. The resulting mixture was cooled to room temperature, diluted with water (10 mL) and extracted with DCM (2×100 mL). The combined organic phases were washed with water (20 mL) and brine (20 mL), dried (magnesium sulfate), and concentrated under reduced pressure. Chromatography of the residue (0-5% 2 M methanolic ammonia/DCM) gave the title compound as a pale yellow oil (40 mg). $^1$H NMR (400 MHz, CDCl$_3$): 7.32 (d, J=8.1 Hz, 2H), 7.23 (d, J=8.0 Hz, 2H), 3.73 (t, J=4.6 Hz, 4H), 3.44 (s, 2H), 2.72-2.58 (m, 4H), 2.54 (t, J=4.5 Hz, 4H), 2.35 (br s, 4H), 1.59-1.53 (m, 4H), 1.44-1.40 (m, 2H).

Example 22

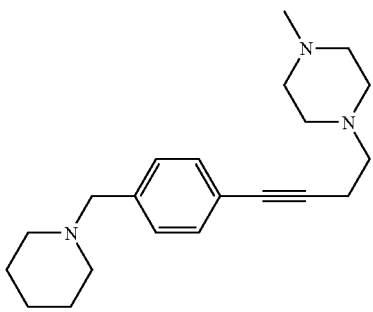

1-Methyl-4-[4-(4-piperidin-1-ylmethyl-phenyl)-but-3-ynyl]-piperazine $K_i$=21 nM A mixture of the product of Example 13 (199 mg), 1-methylpiperazine (0.067 mL) and potassium carbonate (69 mg) in 1:1 ethanol/water (6 mL) was heated at 80° C. for 16 h. The reaction mixture was cooled to room temperature. Water (10 mL) was added, and the mixture was extracted with DCM (2×100 mL). The combined organic phases were washed with water (20 mL) and brine (20 mL), dried (magnesium sulfate), and concentrated under reduced pressure. Chromatography of the residue (0-5% 2 M methanolic ammonia/DCM) gave the title compound as a white solid (13 mg). $^1$H NMR (400 MHz, CDCl$_3$): 7.32 (d, J=8.1 Hz, 2H), 7.23 (d, J=8.1 Hz, 2H), 3.44 (s, 2H), 2.71-2.46 (m, 12H), 2.35 (br s, 4H), 2.30 (s, 3H), 1.59-1.53 (m, 4H), 1.45-1.38 (m, 2H).

Example 23

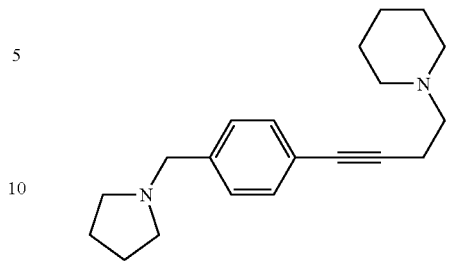

1-[4-(4-Pyrrolidin-1-ylmethyl-phenyl)-but-3-ynyl]-piperidine $K_i$=1.4 nM

A solution of the product of Example 12 (241 mg), pyrrolidine (0.125 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a colorless oil (73 mg). $^1$H NMR (400 MHz, CDCl$_3$): 7.34 (d, J=8.0 Hz, 2H), 7.24 (d, J=8.0 Hz, 2H), 3.58 (s, 2H), 2.68-2.57 (m, 4H), 2.50-2.45 (m, 8H), 1.79-1.76 (m, 4H), 1.63-1.57 (m, 4H), 1.47-1.41 (m, 2H).

Example 24

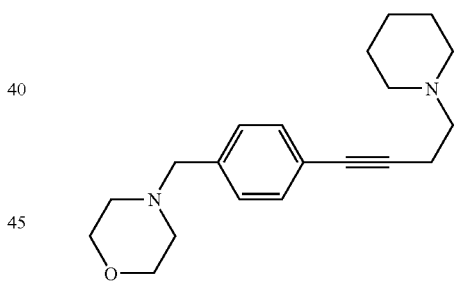

4-[4-(4-Piperidin-1-yl-but-1-ynyl)-benzyl]-morpholine $K_i$=5.5 nM

A solution of the product of Example 12 (241 mg), morpholine (0.131 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a yellow oil (53 mg). $^1$H NMR (400 MHz, CDCl$_3$): 7.34 (d, J=8.2 Hz, 2H), 7.24 (d, J=8.2 Hz, 2H), 3.70 (t, J=4.6 Hz, 4H), 3.47 (s, 2H), 2.68-2.57 (m, 4H), 2.50-2.41 (m, 8H), 1.63-1.57 (m, 4H), 1.48-1.42 (m, 2H).

Example 25

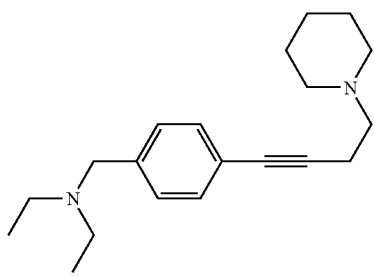

Diethyl-[4-(4-piperidin-1-yl-but-1-ynyl)-benzyl]-amine $K_i$=1.1 nM

A solution of the product of Example 12 (241 mg), diethylamine (0.155 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a colorless oil (61 mg). $^1$H NMR (400 MHz, CDCl$_3$): 7.33 (d, J=8.1 Hz, 2H), 7.24 (d, J=8.0 Hz, 2H), 3.53 (s, 2H), 2.68-2.57 (m, 4H), 2.52-2.45 (m, 8H), 1.63-1.57 (m, 4H), 1.47-1.41 (m, 2H), 1.02 (t, J=7.1 Hz, 6H).

Example 26

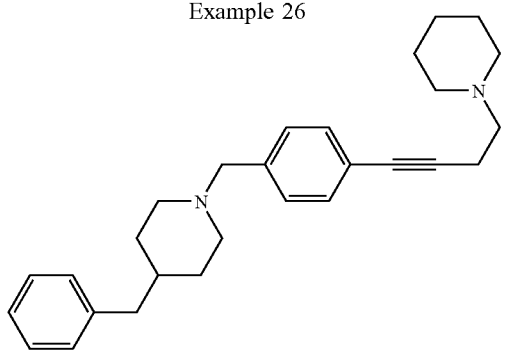

1-{4-[4-(4-Benzyl-piperidin-1-ylmethyl)-phenyl]-but-3-ynyl}-piperidine $K_i$=2.9 nM A solution of the product of Example 12 (241 mg), 4-benzylpiperidine (0.264 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a white solid (80 mg). $^1$H NMR (400 MHz, CDCl$_3$): 7.32 (d, J=8.0 Hz, 2H), 7.28-7.15 (m, 5H), 7.12 (d, J=7.1 Hz, 2H), 3.43 (s, 2H), 2.83-2.80 (d, J=11.5 Hz, 2H), 2.68-2.56 (m, 4H), 2.52 (d, 7.0 Hz, 2H), 2.46 (br s, 4H), 1.87 (t, J=9.9 Hz, 2H), 1.62-1.57 (m, 6H), 1.53-1.41 (m, 3H), 1.34-1.24 (m, 2H)

Example 27

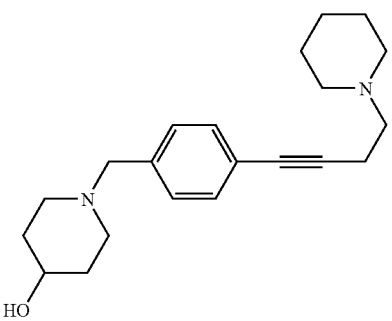

1-[4-(4-Piperidin-1-yl-but-1-ynyl)-benzyl]-piperidin-4-ol $K_i$=1.7 nM

A solution of the product of Example 12 (241 mg), 4-hydroxypiperidine (152 mg) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a colorless oil (60 mg). $^1$H NMR (400 MHz, CDCl$_3$): 7.34 (d, J=8.0 Hz, 2H), 7.22 (d, J=8.0 Hz, 2H), 3.72-3.65 (m, 1H), 3.47 (s, 2H), 2.75-2.57 (m, 6H), 2.47 (br s, 4H), 2.13 (t, J=9.6 Hz, 2H), 1.90-1.84 (m, 2H), 1.63-1.53 (m, 5H), 1.47-1.41 (m, 3H).

Example 28

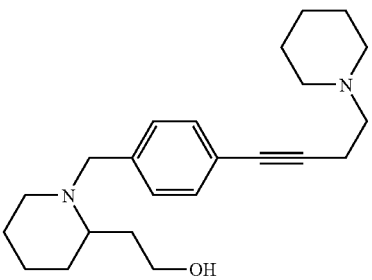

2-{1-[4-(4-Piperidin-1-yl-but-1-ynyl)-benzyl]-piperidin-2-yl}-ethanol $K_i$=0.4 nM A solution of the product of Example 12 (241 mg), 2-piperidineethanol (194 mg) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a colorless oil (9 mg). $^1$H NMR (400 MHz, CDCl$_3$): 7.34 (d, J=8.1 Hz, 2H), 7.22 (d, J=8.0 Hz, 2H), 4.15 (d, J=13.1 Hz, 1H), 3.95-3.90 (m, 1H), 3.77-3.71 (m, 1H), 3.43 (d, J=13.0 Hz, 1H), 2.96-2.90 (m, 1H), 2.74-2.57 (m, 7H), 2.47 (br s, 5H), 2.20-2.12 (m, 1H), 1.97-1.25 (m, 11H)

Example 29

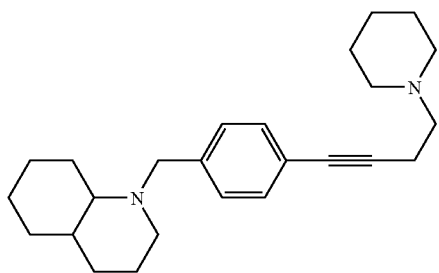

1-[4-(4-Piperidin-1-yl-but-1-ynyl)-benzyl]-decahydro-quinoline $K_i$=0.8 nM

A solution of the product of Example 12 (241 mg), decahydroquinoline (0.224 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a colorless oil (29 mg). $^1$H NMR (400 MHz, CDCl$_3$): 7.32 (d, J=8.0 Hz, 2H), 7.21 (d, J=8.0 Hz, 2H), 4.03 (d, J=13.7 Hz, 1H), 3.19 (d, J=13.7 Hz, 1H), 2.77 (d, J=11.1 Hz, 1H), 2.68-2.57 (m, 5H), 2.47 (br s, 5H), 2.23-2.18 (m, 1H), 1.95-0.83 (m, 18H).

Example 30

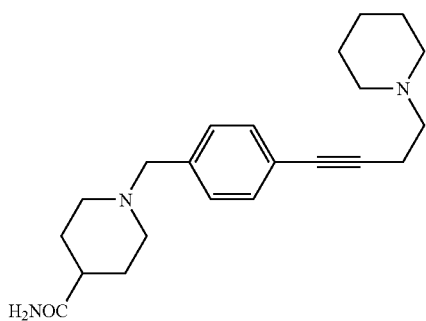

1-[4-(4-Piperidin-1-yl-but-1-ynyl)-benzyl]-piperidine-4-carboxylic acid amide $K_i$=1.6 nM A solution of the product of Example 12 (241 mg), isonipecotamide (192 mg) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a white solid (87 mg). $^1$H NMR (400 MHz, CDCl$_3$): 7.33 (d, J=8.0 Hz, 2H), 7.23 (d, J=8.0 Hz, 2H), 3.94 (s, 2H), 3.49 (s, 2H), 2.67-2.57 (m, 4H), 2.51-2.45 (m, 8H), 1.77-1.71 (m, 5H), 1.63-1.57 (m, 4H), 1.47-1.42 (m, 2H).

Example 31

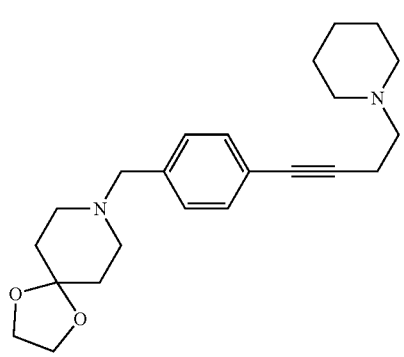

8-[4-(4-Piperidin-1-yl-but-1-ynyl)-benzyl]-1,4-dioxa-8-aza-spiro[4.5]decane $K_i$=1.8 nM A solution of the product of Example 12 (241 mg), 1,4-dioxa-8-azaspiro[4.5]decane (0.192 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a colorless oil (108 mg). $^1$H NMR (400 MHz, CDCl$_3$): 7.33 (d, J=8.1 Hz, 2H), 7.22 (d, J=8.1 Hz, 2H), 5.45 (br s, 1H), 5.31 (br s, 1H), 3.46 (s, 2H), 2.92-2.87 (m, 2H), 2.68-2.57 (m, 4H), 2.47 (br s, 4H), 2.19-2.11 (m, 1H), 2.02-1.95 (m, 2H), 1.87-1.83 (m, 2H), 1.79-1.57 (m, 7H), 1.47-1.41 (m, 2H).

Example 32

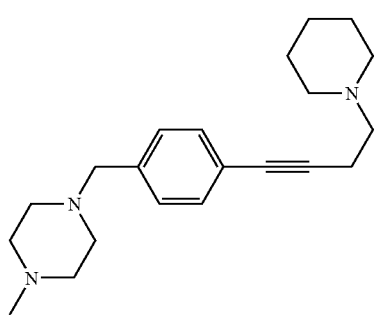

1-Methyl-4-[4-(4-piperidin-1-yl-but-1-ynyl)-benzyl]-piperazine $K_i$=0.7 nM

A solution of the product of Example 12 (241 mg), 1-methylpiperazine (0.166 mL) and acetic acid (0.067 mL)

in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a colorless oil (65 mg). $^1$H NMR (400 MHz, CDCl$_3$): 7.33 (d, J=8.2 Hz, 2H), 7.23 (d, J=8.2 Hz, 2H), 3.47 (s, 2H), 2.68-2.57 (m, 4H), 2.47 (br s, 12H), 2.28 (s, 3H), 1.62-1.57 (m, 4H), 1.47-1.41 (m, 2H).

Example 33

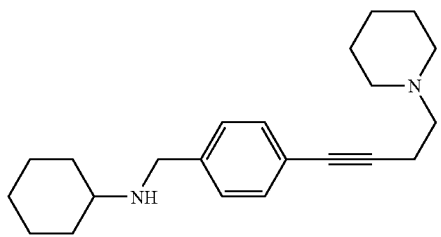

Cyclohexyl-[4-(4-piperidin-1-yl-but-1-ynyl)-benzyl]-amine

K$_i$=0.5 nM

A solution of the product of Example 12 (241 mg), cyclohexylamine (0.172 mL), and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a colorless oil (95 mg). $^1$H NMR (400 MHz, CDCl$_3$): 7.34 (d, J=8.0 Hz, 2H), 7.23 (d, J=8.0 Hz, 2H), 3.79 (s, 2H), 2.68-2.57 (m, 4H), 2.49-2.40 (m, 5H), 1.92-1.86 (m, 2H), 1.76-1.69 (m, 2H), 1.62-1.54 (m, 4H), 1.47-1.41 (m, 2H), 1.29-1.05 (m, 6H).

Example 34

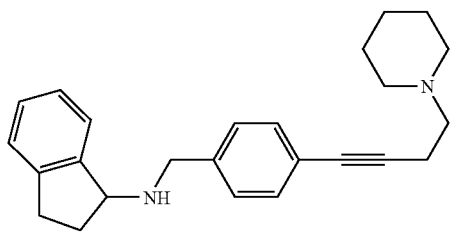

Indan-1-yl-[4-(4-piperidin-1-yl-but-1-ynyl)-benzyl]-amine

K$_i$=1.3 nM

A solution of the product of Example 12 (241 mg), 1-aminoindian (0.192 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a colorless oil (118 mg). $^1$H NMR (400 MHz, CDCl$_3$): 7.37-7.28 (m, 8H), 4.27 (t, 6.6 Hz, 1H), 3.88 (d, 5.6 Hz, 2H), 3.05-2.97 (m, 1H), 2.85-2.77 (m, 1H), 2.68-2.57 (m, 4H), 2.49-2.57 (m, 5H), 1.90-1.82 (m, 1H), 1.63-1.57 (m, 4H), 1.47-1.41 (m, 2H).

Example 35

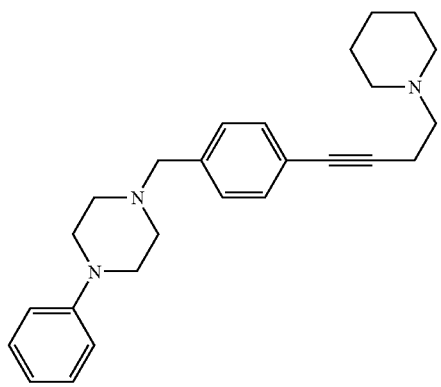

1-Phenyl-4-[4-(4-piperidin-1-yl-but-1-ynyl)-benzyl]-piperazine

K$_i$=7.0 nM

A solution of the product of Example 12 (241 mg), 1-phenylpiperazine (0.229 mL) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a colorless oil (38 mg). $^1$H NMR (400 MHz, CDCl$_3$): 7.17 (d, J=8.0 Hz, 2H), 7.09-7.05 (m, 4H), 6.74 (d, J=8.2 Hz, 2H), 6.67 (t, J=7.4 Hz, 1H), 3.36 (s, 2H), 3.01 (t, 4.9 Hz, 4H), 2.50-2.39 (m, 8H), 2.29 (br s, 4H), 1.45-1.37 (m, 4H), 1.30-1.23 (m, 2H).

Example 36

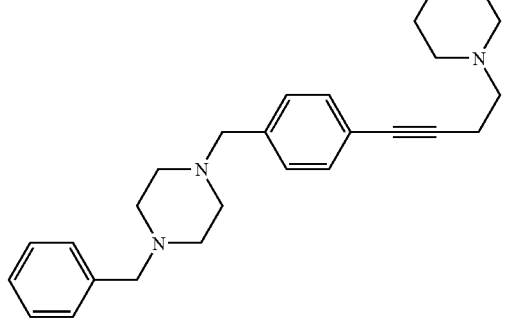

1-Benzyl-4-[4-(4-piperidin-1-yl-but-1-ynyl)-benzyl]-piperazine

K$_i$=9.0 nM

A solution of the product of Example 12 (241 mg), 1-benzylpiperazine (0.261 mL) and acetic acid (0.067 mL)

in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a colorless oil (136 mg). $^1$H NMR (400 MHz, CDCl$_3$): 7.38-7.21 (m, 9H), 3.51 (s, 2H), 3.48 (s, 2H), 2.68-2.56 (m, 4H), 2.46 (br s, 10H), 1.62-1.56 (m, 6H), 1.47-1.42 (m, 2H).

Example 37

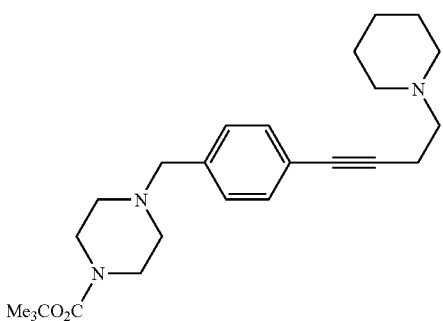

4-[4-(4-Piperidin-1-yl-but-1-ynyl)-benzyl]-piperazine-1-carboxylic acid tert-butyl ester $K_i$=15 nM A solution of the product of Example 12 (241 mg), tert-butyl 1-piperazinecarboxylate (559 mg) and acetic acid (0.067 mL) in DCM (2 mL) was treated with sodium triacetoxyborohydride (318 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a white solid (218 mg). $^1$H NMR (400 MHz, CDCl$_3$): 7.34 (d, J=8.1 Hz, 2H), 7.23 (d, J=8.0 Hz, 2H), 3.48 (s, 2H), 3.43-3.40 (m, 4H), 2.68-2.57 (m, 4H), 2.47 (br s, 4H), 2.36 (br s, 4H), 1.64-1.57 (m, 6H), 1.45 (s, 9H).

Example 38

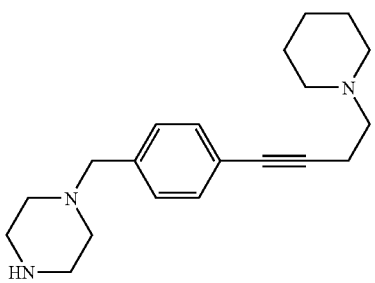

1-[4-(4-Piperidin-1-yl-but-1-ynyl)-benzyl]-piperazine $K_i$=1.3 nM

A solution of the product of Example 37 (184 mg) in 1,4-dioxane (7 mL) was treated with 4 N HCl in 1,4-dioxane at room temperature for 16 h. The solvent was evaporated, and the resulting mixture was treated with 10% aqueous sodium hydroxide (10 mL). The aqueous phase was extracted with 10% methanol in DCM (2×100 mL). The combined organic phases were washed with brine (50 mL), dried (magnesium sulfate), and concentrated under reduced pressure. Chromatography of the residue (1-6% 2 M methanolic ammonia/DCM) gave the title compound as a white solid (97 mg). $^1$H NMR (400 MHz, CDCl$_3$): 7.34 (d, J=8.0 Hz, 2H), 7.23 (d, J=8.0 Hz, 2H), 3.47 (s, 2H), 2.91 (t, J=4.8 Hz, 4H), 2.69-2.58 (m, 4H), 2.48-2.43 (m, 8H), 1.64-1.58 (m, 4H), 1.47-1.41 (m, 2H).

Example 39

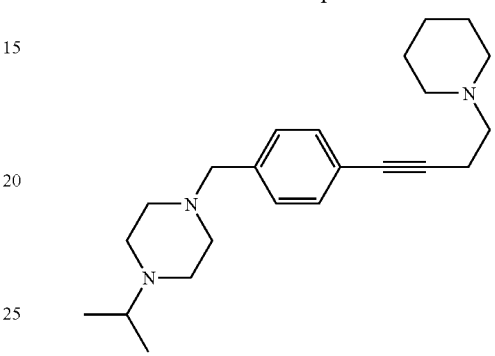

1-Isopropyl-4-[4-(4-piperidin-1-yl-but-1-ynyl)-benzyl]-piperazine $K_i$=1.3 nM

A solution of the product of Example 38 (74 mg), acetone (5 mL) and acetic acid (0.014 mL) in DCM (3 mL) was treated with sodium triacetoxyborohydride (67 mg) at room temperature. After 16 h, the resulting mixture was treated with 10% aqueous sodium hydroxide (10 mL). The aqueous phase was extracted with DCM (2×100 mL). The combined organic phases were washed with brine (50 mL), dried (magnesium sulfate), and concentrated under reduced pressure. Chromatography of the residue (0.5-5.5% 2 M methanolic ammonia/DCM) gave the title compound as a colorless oil (65 mg). $^1$H NMR (400 MHz, CDCl$_3$): 7.33 (d, J=8.0 Hz, 2H), 7.23 (d, J=8.1 Hz, 2H), 3.48 (s, 2H), 2.68-2.47 (m, 16H), 1.66 (br s, 1H), 1.63-1.57 (m, 4H), 1.48-1.41 (m, 2H), 1.04 (d, J=6.5 Hz, 2H).

Example 40

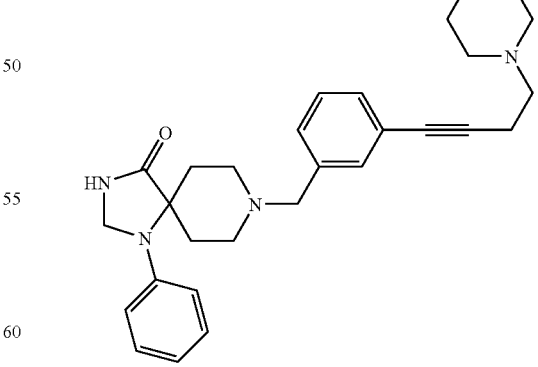

1-Phenyl-8-[3-(4-piperidin-1-yl-but-1-ynyl)-benzyl]-1,3,8-triaza-spiro[4.5]decan-4-one $K_i$=2.0 nM Prepared analogously to Example 15 using 1-phenyl-1,3,8-triaza-spiro[4.5]decan-4-one. $^1$H NMR(400 MHz, CDCl$_3$): 7.41(s, 1H), 7.32-7.21(m, 5H), 6.94-6.85(m, 2H), 4.73(s, 2H), 3.54(s, 2H), 2.84-2.58(m, 10H), 2.47(bs, 4H), 1.65(d, 23.2 Hz, 2H), 1.62-1.58(m, 4H), 1.47-1.43(m, 2H).

8.64 (d, J=2.6 Hz, 1H), 8.50-8.48 (m, 1H), 7.80 (d, J=7.9 Hz, 1H), 7.81-7.12(m, 5H), 3.64(d, J=13.5 Hz, 1H), 3.17-3.13 (m, 1H), 2.94(d, J=11.4 Hz, 1H), 2.79(d, J=13.6 Hz, 1H), 2.60-2.58(m, 4H), 2.47(bs, 4H), 1.96-1.90(m, 1H), 1.82-1.75(m, 2H), 1.66-1.39(m, 10H).

Example 41

Example 43

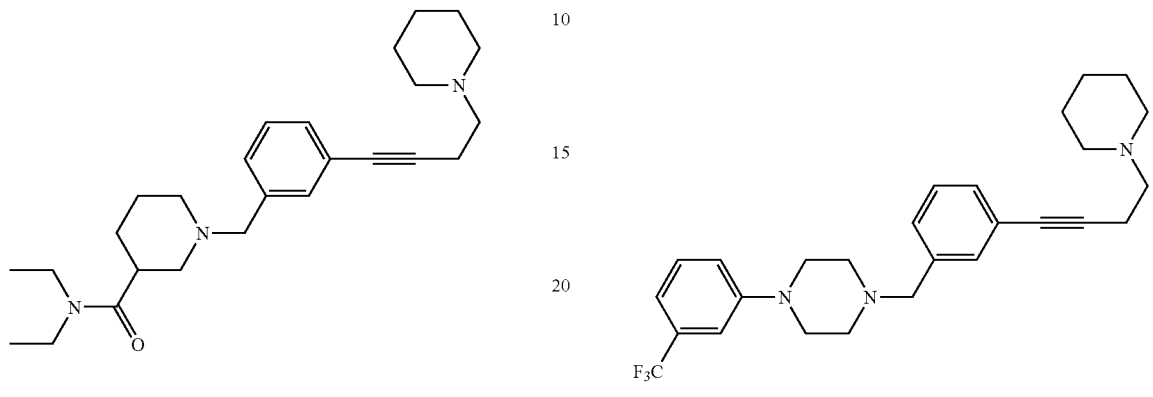

1-[3-(4-Piperidin-1-yl-but-1-ynyl)-benzyl]-piperidine-3-carboxylic acid diethylamide K$_i$=3.0 nM Prepared analogously to Example 15 using piperidine-3-carboxylic acid diethylamide. $^1$H NMR (400 MHz, CDCl$_3$): 7.36(s, 1H), 7.28-7.21(m, 3H), 3.46(s, 2H), 3.38-3.25(m, 4H), 2.87-2.81(m, 2H), 2.75-2.57(m, 5H), 2.46-2.42(m, 4H), 2.19(t, J=11.1 Hz, 1H), 1.99-1.94(m, 1H), 1.77-1.42(m, 10H), 3.94(t, J=7.1 Hz, 3H), 1.07(t, J=7.1 Hz, 3H).

1-[3-(4-Piperidin-1-yl-but-1-ynyl)-benzyl]-4-(3-trifluoromethyl-phenyl)-piperazine K$_i$=91 nM Prepared analogously to Example 15 using 1-(3-trifluoromethyl-phenyl)-piperazine. $^1$H NMR(400 MHz, CDCl$_3$): 7.39(s, 1H), 7.35-7.22(m, 4H), 7.10-7.03(m, 3H), 3.52(s, 2H), 3.24(t, J=5.0 Hz, 4H), 2.69-2.58(m, 8H), 2.47(bs, 4H), 1.63-1.58(m, 4H), 1.47-1.42(m, 2H).

Example 42

Example 44

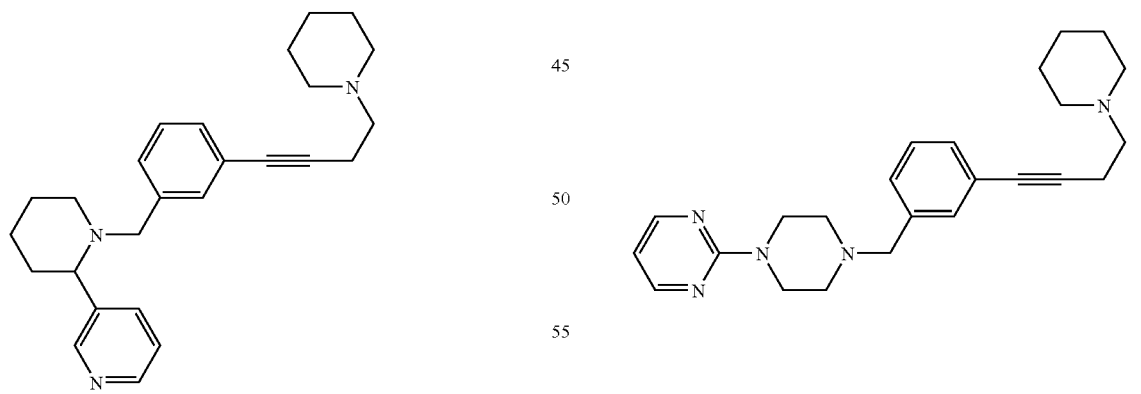

1-[3-(4-Piperidin-1-yl-but-1-ynyl)-benzyl]-1,2,3,4,5,6-hexahydro-[2,3']bipyridinyl K$_i$=11 nM Prepared analogously to Example 15 using 1,2,3,4,5,6-hexahydro-[2,3']bipyridinyl. $^1$H NMR (400 MHz, CDCl$_3$):

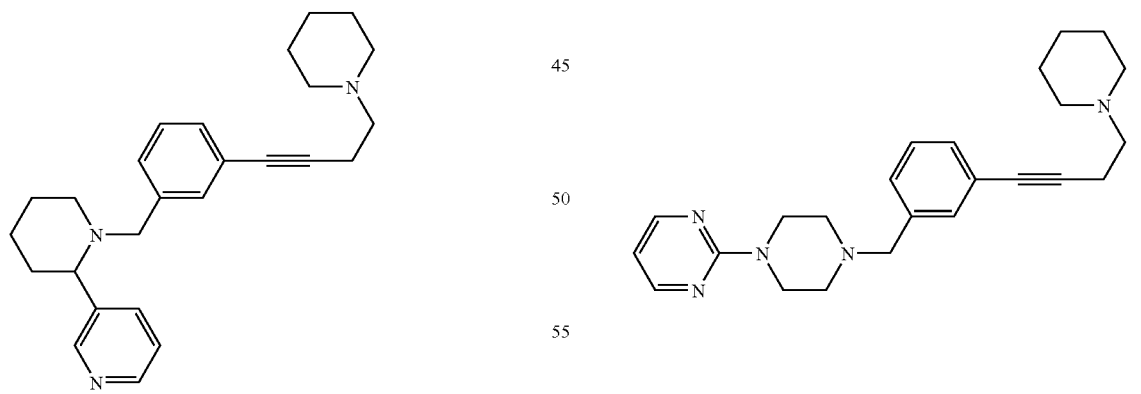

2-{4-[3-(4-Piperidin-1-yl-but-1-ynyl)-benzyl]-piperazin-1-yl}-pyrimidine

K$_i$=9.0 nM

Prepared analogously to Example 15 using 2-piperazin-1-yl-pyrimidine. $^1$H NMR (400 MHz, CDCl$_3$): 8.29(d, J=4.7 Hz, 2H), 7.39(s, 1H), 7.31-7.22(m, 3H), 6.46(t, J=4.8 Hz, 1H), 3.82(t, J=5.1 Hz, 4H), 3.50(s, 2H), 2.68-2.58(m, 4H), 2.50-2.47(m, 8H), 1.72-1.57(m, 4H), 1.47-1.41(m, 2H).

Example 45

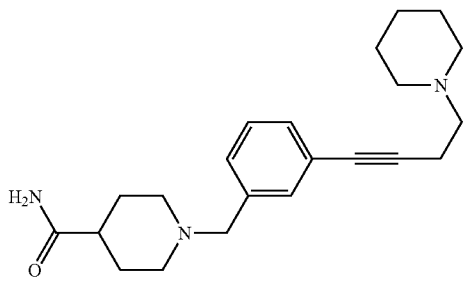

1-[3-(4-Piperidin-1-yl-but-1-ynyl)-benzyl]-piperidine-4-carboxylic acid amide $K_i$=2.0 nM Prepared analogously to Example 15 using piperidine-4-carboxylic acid amide. $^1$H NMR (400 MHz, CDCl$_3$): 8.29(s, 1H), 7.40(s, 1H), 7.31-7.23(m, 3H), 4.38-4.31(m, 1H), 3.52 (S, 2H), 3.02(d, 2H), 2.70-2.55(m, 4H), 2.48-2.42(m, 8H), 2.19-2.13(m, 2H), 1.81-1.78(m, 2H) 1.63-1.60(m, 2H), 1.46-1.45(m, 2H).

Example 46

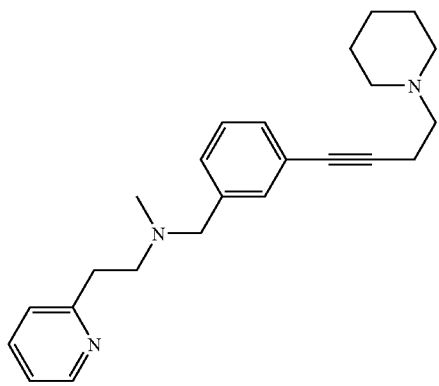

Methyl-[3-(4-piperidin-1-yl-but-1-ynyl)-benzyl]-(2-pyridin-2-yl-ethyl)-amine $K_i$=4.0 nM Prepared analogously to Example 15 using methyl-(2-pyridin-2-yl-ethyl)-amine. $^1$H NMR (400 MHz, CDCl$_3$): 8.53-8.51(m, 1H), 7.61-7.56(m, 1H), 7.30-7.09(m, 6H), 3.51 (s, 2H), 3.02-2.98(m, 2H), 2.82-2.78(m, 2H), 2.68-2.57(m, 4H), 2.47(bs, 4H), 2.26(s, 3H), 1.63-1.57(m, 4H), 1.47-1.42 (m, 2H).

Example 47

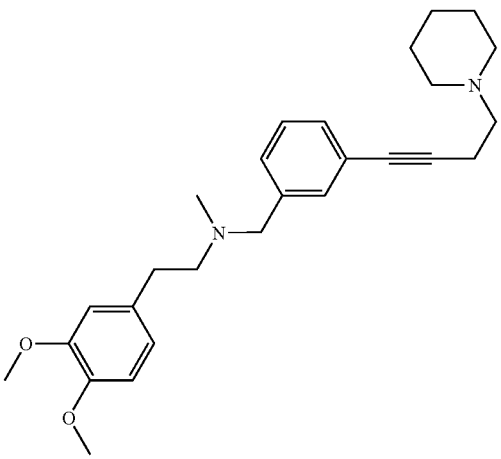

[2-(3,4-Dimethoxy-phenyl)-ethyl]-methyl-[3-(4-piperidin-1-yl-but-1-ynyl)-benzyl]-amine $K_i$=3.0 nM Prepared analogously to Example 15 using [2-(3,4-dimethoxy-phenyl)-ethyl]-methyl-amine. $^1$H NMR (400 MHz, CDCl$_3$): 7.36(s, 1H), 7.29-7.20(m, 3H), 6.80-6.71(m, 3H), 3.86(s, 6H), 3.51(s, 2H), 2.78-2.75(m, 2H), 2.68-2.57 (m, 6H), 2.46(bs, 4H), 2.26(s, 3H), 1.63-1.59(m, 4H), 1.47-1.44(m, 2H).

Example 48

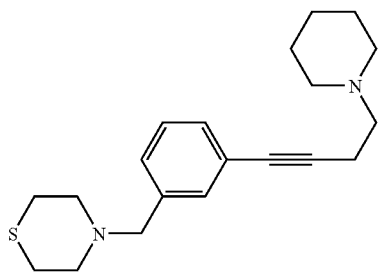

4-[3-(4-Piperidin-1-yl-but-1-ynyl)-benzyl]-thiomorpholine $K_i$=1.0 nM

Prepared analogously to Example 15 using thiomorpholine. $^1$H NMR (400 MHz, CDCl$_3$): 7.34(s, 1H), 7.29-7.20(m, 3H), 3.46(s, 2H), 2.69-2.57(m, 12H), 2.47(s, 4H), 1.63-1.57 (m, 4H), 1.47-1.42(m, 2H).

Example 49

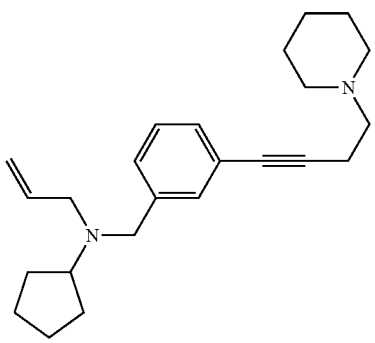

Allyl-cyclopentyl-[3-(4-piperidin-1-yl-but-1-ynyl)-benzyl]-amine $K_i$=2.0 nM

Prepared analogously to Example 15 using allyl-cyclopentyl-amine. $^1$H NMR (400 MHz, CDCl$_3$): 7.37(s, 1H), 7.26-7.18(m, 3H), 5.94-5.84(m, 1H), 5.16-5.09(m, 2H), 3.57 (s, 2H), 3.13-3.07(m, 3H), 2.69-2.57(m, 4H), 2.47(bs, 4H), 1.81-1.75(m, 2H), 1.67-1.43(m, 12H).

Example 50

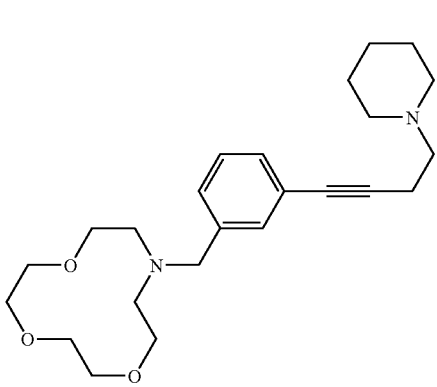

10-[3-(4-Piperidin-1-yl-but-1-ynyl)-benzyl]-1,4,7-trioxa-10-aza-cyclododecane $K_i$=2.0 nM Prepared analogously to Example 15 using 1,4,7-trioxa-10-aza-cyclododecane. $^1$H NMR (400 MHz, CDCl$_3$): 7.38(s, 1H), 7.30-7.19(m, 3H), 3.72-2.69(m, 8H), 3.64-3.62(m, 6H), 2.74(t, J=4.9 Hz, 4H), 2.68-2.58(m, 4H), 2.47(bs, 4H), 1.63-1.57(m, 4H), 1.47-1.43(m, 2H).

Example 51

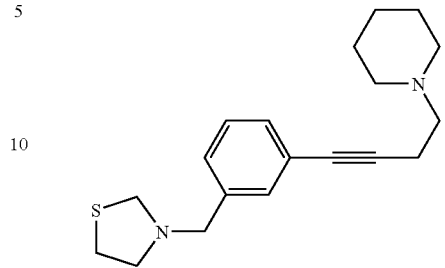

1-[4-(3-Thiazolidin-3-ylmethyl-phenyl)-but-3-ynyl]-piperidine $K_i$=1.0 nM

Prepared analogously to Example 15 using thiazolidine. $^1$H NMR (400 MHz, CDCl$_3$): 7.41(s, 1H), 7.32-7.23(m, 3H), 4.05(s, 2H), 3.51(s, 2H), 3.09(t, J=6.3 Hz, 2H), 2.95(t, J=6.4 Hz, 2H), 2.68-2.58(m, 4H), 2.47(bs, 4H), 1.63-1.58(m, 4H), 1.47-1.43(m, 2H).

Example 52

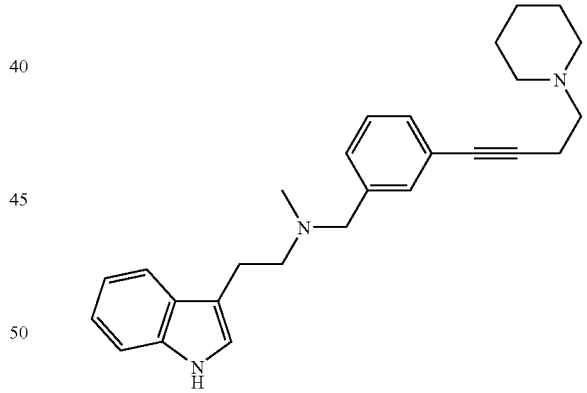

[2-(1H-Indol-3-yl)-ethyl]-methyl-[3-(4-piperidin-1-yl-but-1-ynyl)-benzyl]-amine $K_1$=2.0 nM Prepared analogously to Example 15 using [2-(1H-indol-3-yl)-ethyl]-methyl-amine. $^1$H NMR (400 MHz, CDCl$_3$): 8.11(s, 1H), 7.55(d, 1H), 7.36-7.01(m, 8H), 3.54(s, 2H), 3.00-2.96(m, 2H), 2.75-2.58(m, 6H), 2.48(bs, 4H), 2.32(s, 3H), 1.63-1.59(m, 4H), 1.47-1.43(m, 2H).

Example 53

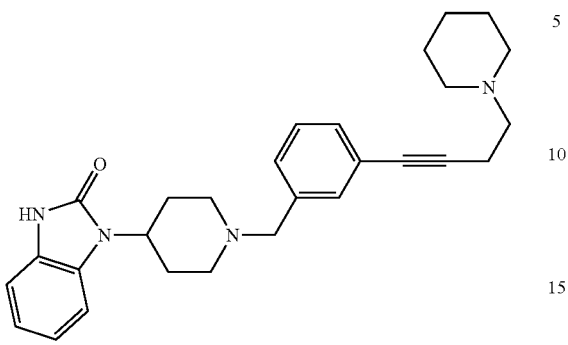

1-{1-[3-(4-Piperidin-1-yl-but-1-ynyl)-benzyl]-piperidin-4-yl}-1,3-dihydro-benzoim-2-one $K_i$=1.0 nM Prepared analogously to Example 15 using 1-piperidin-4-yl-1,3-dihydro-benzoimidazol-2-one. $^1$H NMR (400 MHz, CDCl$_3$): 7.35(s, 1H), 7.29-7.21(m, 3H), 5.41(d, 30.1 Hz, 2H), 3.45(s, 2H), 2.90(d, J=11.7 Hz, 2H), 2.68-2.57(m, 4H), 2.68-2.57(m, 4H), 2.47(bs, 4H), 2.19-2.11(m, 1H), 2.02-1.96(m, 2H), 1.88-1.63(m, 4H), 1.62-1.57(m, 4H), 1.47-1.42(m, 2H).

Example 54

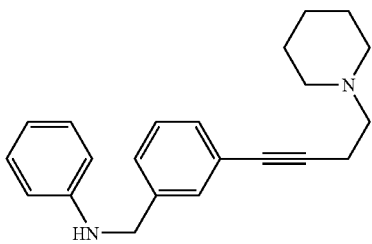

Phenyl-[3-(4-piperidin-1-yl-but-1-ynyl)-benzyl]-amine $K_i$=110 nM

Prepared analogously to Example 15 using aniline. $^1$H NMR (400 MHz, CDCl$_3$): 7.41(s, 1H), 7.40-7.24(m, 3H), 7.19-7.15(m, 2H), 6.72(t, J=7.3 Hz, 1H), 6.63-6.61(m, 2H), 4.29(d, J=5.2 Hz, 2H), 4.03(bs, 1H), 2.68-2.57(m, 4H), 2.46(bs, 4H), 2.18(s, 1H), 1.62-1.57(m, 4H), 1.47-1.44(m, 2H).

Example 55

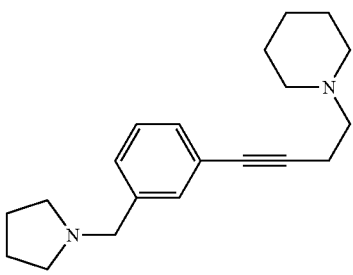

1-[4-(3-Pyrrolidin-1-ylmethyl-phenyl)-but-3-ynyl]-piperidine $K_i$=1.0 nM

Prepared analogously to Example 15 using pyrrolidine. $^1$H NMR (400 MHz, CDCl$_3$): 7.37(s, 1H), 7.28-7.22(m, 3H), 3.56(s, 2H), 2.68-2.57(m, 4H), 2.51-2.46(m, 8H), 1.79-1.76 (m, 4H), 1.70-1.57(m, 4H), 1.47-1.43(m, 2H).

Example 56

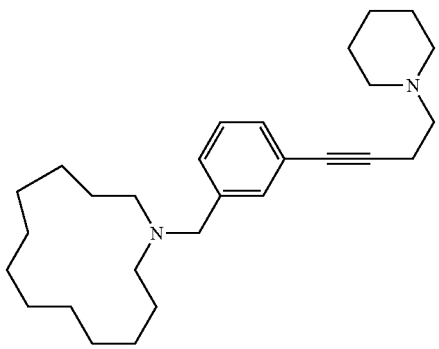

1-[3-(4-Piperidin-1-yl-but-1-ynyl)-benzyl]-azacyclotridecane $K_i$=13 nM

Prepared analogously to Example 15 using azacyclotridecane. $^1$H NMR (400 MHz, CDCl$_3$): 7.37(s, 1H), 7.28-7.19 (m, 3H), 3.43(s, 2H), 2.50(bs, 4H), 2.36-2.33(m, 8H), 1.65-1.38(m, 26H).

Example 57

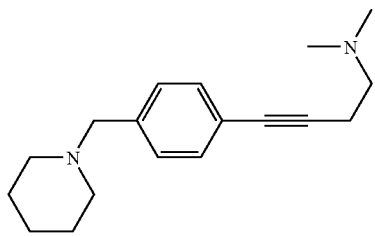

Dimethyl-[4-(4-piperidin-1-ylmethyl-phenyl)-but-3-ynyl]-amine

May be prepared analogously to Example 19 using dimethylamine hydrochloride.

Example 58

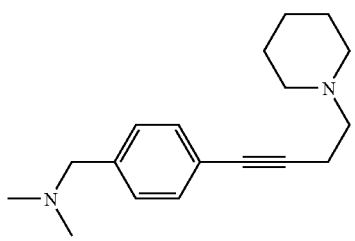

Dimethyl-[4-(4-piperidin-1-yl-but-1-ynyl)-benzyl]-amine

May be prepared analogously to Example 23 using dimethylamine hydrochloride.

Example 59

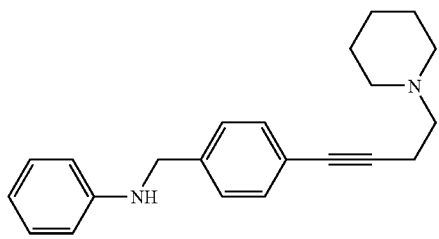

Phenyl-[4-(4-piperidin-1-yl-but-1-ynyl)-benzyl]-amine

May be prepared analogously to Example 23 using aniline.

Example 60

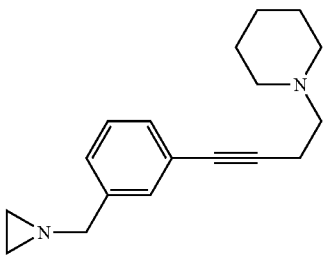

1-[4-(3-Aziridin-1-ylmethyl-phenyl)-but-3-ynyl]-piperidine

May be prepared analogously to Example 15 using aziridine hydrochloride.

Example 61

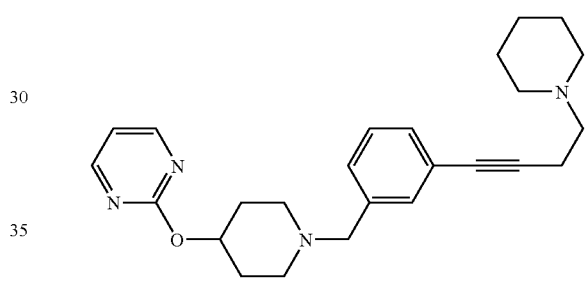

2-{1-[3-(4-Piperidin-1-yl-but-1-ynyl)-benzyl]-piperidin-4-yloxy}-pyrimidine

May be prepared analogously to Example 15 using 2-(piperidin-4-yloxy)-pyrimidine.

Example 62

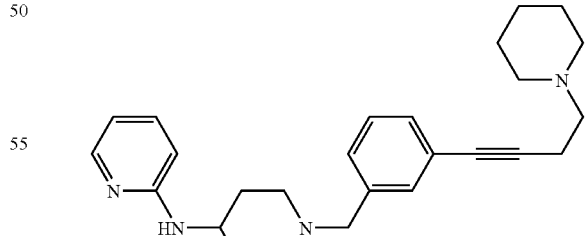

{1-[3-(4-Piperidin-1-yl-but-1-ynyl)-benzyl]-piperidin-4-yl}-pyridin-2-yl-amine

May be prepared analogously to Example 15 using piperidin-4-yl-pyridin-2-yl-amine.

Example 63

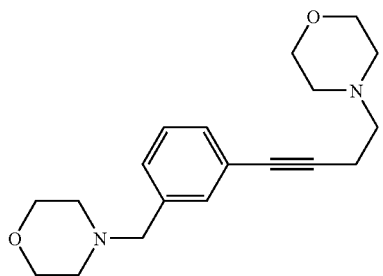

4-[4-(3-Morpholin-4-ylmethyl-phenyl)-but-3-ynyl]-morpholine

May be prepared analogously to Example 15 using the product of Example 10 and morpholine.

Example 64

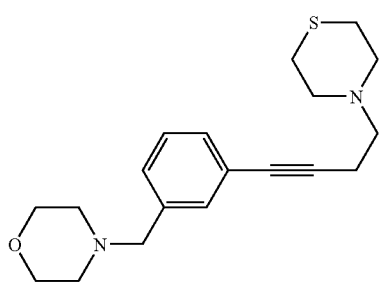

4-[3-(4-Thiomorpholin-4-yl-but-1-ynyl)-benzyl]-morpholine

May be prepared analogously to Example 15 using the product of Example 11 and morpholine.

Example 65

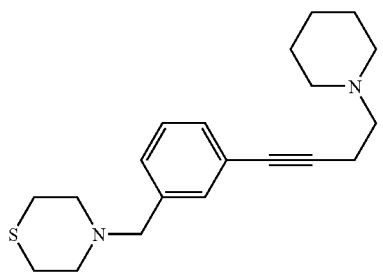

4-[3-(4-Piperidin-1-yl-but-1-ynyl)-benzyl]-thiomorpholine

May be prepared analogously to Example 15 using thiomorpholine.

Example 66

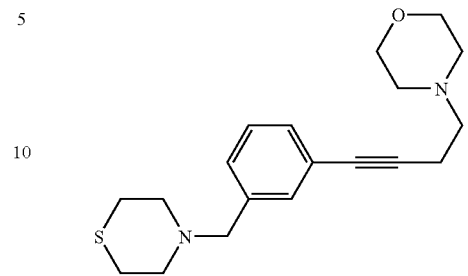

4-[4-(3-Thiomorpholin-4-ylmethyl-phenyl)-but-3-ynyl]-morpholine

May be prepared analogously to Example 15 using the product of Example 10 and thiomorpholine.

Example 67

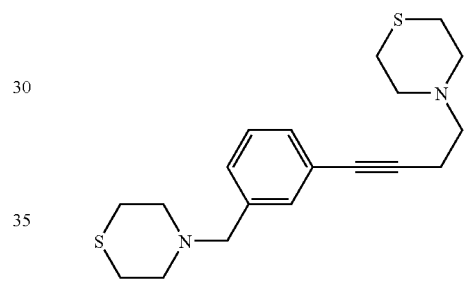

4-[3-(4-Thiomorpholin-4-yl-but-1-ynyl)-benzyl]-thiomorpholine

May be prepared analogously to Example 15 using the product of Example 11 and thiomorpholine.

Example 68

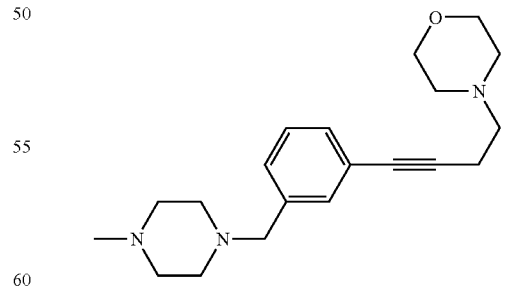

4-{4-[3-(4-Methyl-piperazin-1-ylmethyl)-phenyl]-but-3-ynyl}-morpholine

May be prepared analogously to Example 15 using the product of Example 10 and 1-methylpiperazine.

Example 69

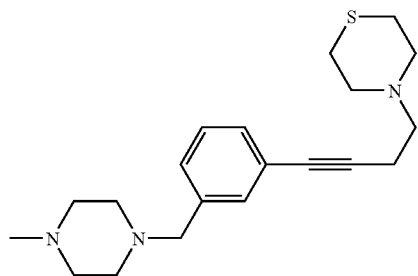

4-{4-[3-(4-Methyl-piperazin-1-ylmethyl)-phenyl]-but-3-ynyl}-thiomorpholine

May be prepared analogously to Example 15 using the product of Example 11 and 1-methylpiperazine.

Example 70

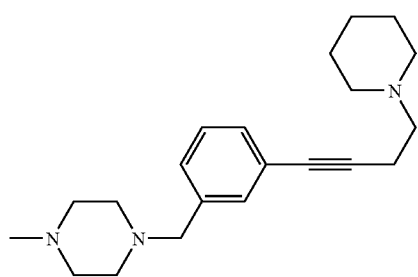

1-Methyl-4-[3-(4-piperidin-1-yl-but-1-ynyl)-benzyl]-piperazine

May be prepared analogously to Example 15 using 1-methylpiperazine.

Example 71

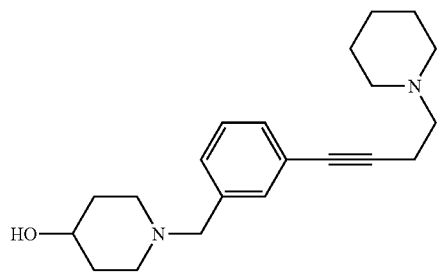

1-[3-(4-Piperidin-1-yl-but-1-ynyl)-benzyl]-piperidin-4-ol

May be prepared analogously to Example 15 using piperidin-4-ol.

Example 72

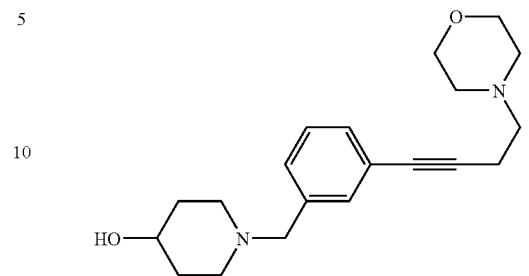

1-[3-(4-Morpholin-4-yl-but-1-ynyl)-benzyl]-piperidin-4-ol

May be prepared analogously to Example 15 using the product of Example 10 and piperidin-4-ol.

Example 73

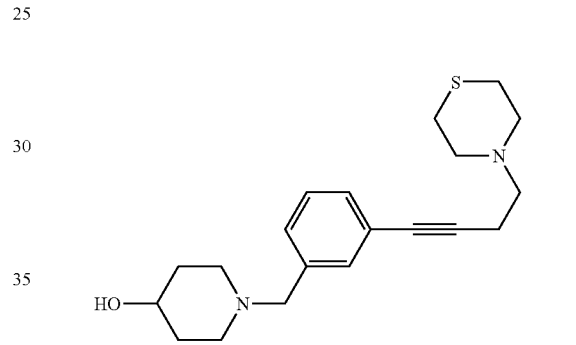

1-[3-(4-Thiomorpholin-4-yl-but-1-ynyl)-benzyl]-piperidin-4-ol

May be prepared analogously to Example 15 using the product of Example 11 and piperidin-4-ol.

Example 74

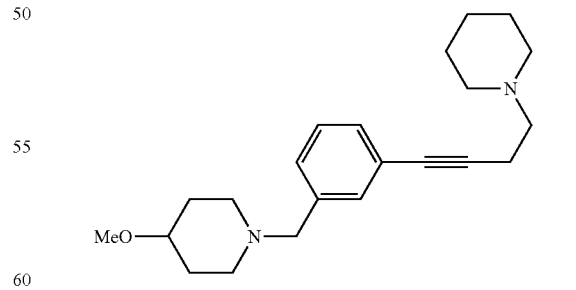

1-{4-[3-(4-Methoxy-piperidin-1-ylmethyl)-phenyl]-but-3-ynyl}-piperidine

May be prepared analogously to Example 15 using 4-methoxypiperidine.

Example 75

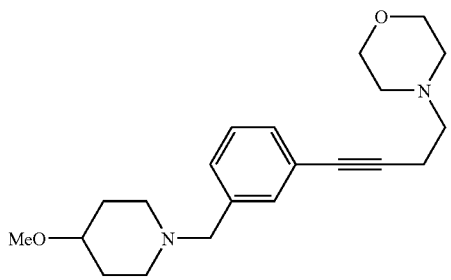

4-{4-[3-(4-Methoxy-piperidin-1-ylmethyl)-phenyl]-but-3-ynyl}-morpholine

May be prepared analogously to Example 15 using the product of Example 10 and 4-methoxypiperidine.

Example 76

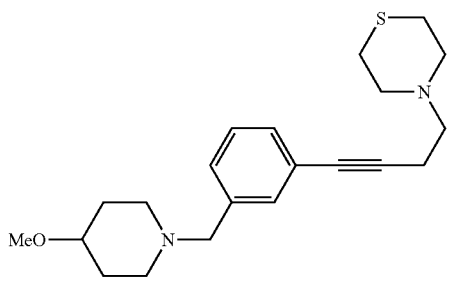

4-{4-[3-(4-Methoxy-piperidin-1-ylmethyl)-phenyl]-but-3-ynyl}-thiomorpholine

May be prepared analogously to Example 15 using the product of Example 11 and 4-methoxypiperidine.

Example 77

Biological Methods

In Vitro

Transfection of Cells with Human Histamine Receptor

A 10 cm tissue culture dish with a confluent monolayer of SK-N-MC cells was split two days prior to transfection. Using sterile technique the media were removed and the cells were detached from the dish by the addition of trypsin. One fifth of the cells were then placed onto a new 10 cm dish. Cells were grown in a 37° C. incubator with 5% $CO_2$ in Minimal Essential Media Eagle with 10% Fetal Bovine Serum. After two days cells were approximately 80% confluent. These were removed from the dish with trypsin and pelleted in a clinical centrifuge. The pellet was then resuspended in 400 µL complete media and transferred to an electroporation cuvette with a 0.4 cm gap between the electrodes. One microgram of supercoiled $H_3$ receptor cDNA was added to the cells and mixed. The voltage for the electroporation was set at 0.25 kV, the capacitance was set at 960 µF. After electroporation the cells were diluted into 10 mL complete media and plated onto four 10 cm dishes. Because of the variability in the efficiency of electroporation, four different concentrations of cells were plated. The ratios used were; 1:20, 1:10, 1:5, with the remainder of the cells being added to the fourth dish. The cells were allowed to recover for 24 hours before adding the selection media (complete media with 600 µg/mL G418). After 10 days dishes were analyzed for surviving colonies of cells. Dishes with well isolated colonies were used. Cells from individual colonies were isolated and tested. SK-N-MC cells were used because they give efficient coupling for inhibition of adenylate cyclase. The clones that gave the most robust inhibition of adenylate cyclase in response to histamine were used for further study.

[$^3$H]-N-methylhistamine Binding

Cell pellets from histamine $H_3$ receptor-expressing SK-N-MC cells were homogenized in 20 mM Tris HCl/0.5 mM EDTA. Supernatants from a 800 g spin were collected, recentrifuged at 30,000 g for 30 min. Pellets were rehomogenized in 50 mM Tris/5 mM EDTA (pH 7.4). Membranes were incubated with 0.8 nM [$^3$H]-N-methylhistamine plus/minus test compounds for 45 min at 25° C. and harvested by rapid filtration over GF/C glass fiber filters (pretreated with 0.3% polyethylenimine) followed by four washes with ice cold buffer. Filters were dried, added to 4 mL scintillation cocktail and then counted on a liquid scintillation counter. Non-specific binding was defined with 10 µM histamine. The $pK_i$ values were calculated based on a $K_d$ of 800 pM and a ligand concentration ([L]) of 800 pM according to the formula:

$$K_i = (IC_{50})/(1+([L]/(K_d)))$$

In Vivo

Elucidation of Oral Absorption and Blood-brain Barrier Penetration Profiles of $H_3$ Receptor Antagonists in the Rat A rat in vivo system was used to determine the blood-brain barrier penetration profiles and kinetics of various $H_3$ receptor antagonists after single bolus oral administration.

Female Sprague Dawley Rats (~300 gram body weight) were housed in accordance with institutional standards and allowed to acclimate for at least 7 days prior to the study. Each $H_3$ antagonist was formulated in 0.5% hydroxypropylmethyl cellulose at a concentration of 1 mg/mL for oral dosing. The test compound was administered to each of eight animals as a single oral dose of 10 mL/kg (10 mg/kg). Remaining dosing solution was retained for analysis. Two animals from each original group of eight were euthanized via $CO_2$ asphyxiation at t=1, 6, 24, and 48 h. After each animal was euthanized, 0.1 mL of its blood was sampled via cardiac puncture, and its brain was removed via dissection of the cranial bones and placed in a pre-weighed 50 mL conical tube on dry ice.

The blood was added to 0.3 mL of 6% trichloroacetic acid, and the acidified sample was vortexed and then centrifuged (5 min at 14,000 rpm in a microcentrifuge). The clear supernatant was retained for analysis. The frozen brain was weighed, homogenized in 6% trichloroacetic acid (3 mL/g wet weight of tissue), and then centrifuged. The clear supernatant was retained for analysis. The supernatants from the blood and brain samples were analyzed by liquid chromatography with mass spectral detection utilizing selective reaction monitoring (LC-MS/MS). The LC method used a Phenomonex Polar RP column (2×50 mm) and a linear solvent gradient of water and acetonitrile (both 1% in acetic acid).

Graphs of $H_3$ receptor antagonist concentration versus time for blood and brain were generated from the LC-MS/MS results. The mean residency time (MRT) of the $H_3$ receptor antagonist, in blood or in the brain, was calculated from the ratio of the area under the first moment curve (AUMC) to the area under the concentration time curve (AUC): AUMC/AUC. The Blood Brain Barrier index was calculated from the log of $AUC_{brain}/AUC_{blood}$.

F. Other Embodiments

The features and advantages of the invention will be apparent to one of ordinary skill in view of the discussion, examples, embodiments, and claims relating to the invention. The invention also contemplates variations and adaptations, based on the disclosure herein concerning the key features and advantages of the invention, and within the abilities of one of ordinary skill.

What is claimed is:
1. A compound of formula (I)

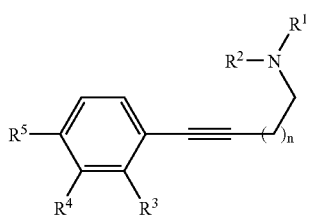

wherein n is an integer from 0 to 1;

$R^1$ and $R^2$ are independently selected from $C_{1-3}$ alkyl, allyl, and $C_{3-8}$ cycloalkyl, or taken together with the nitrogen to which they are attached, they form a non-aromatic 4-7 membered heterocyclyl optionally including up to two additional heteroatoms independently selected from O, S, and N;

one of $R^3$, $R^4$, and $R^5$ is G, one of the remaining two is hydrogen, and the other is selected from hydrogen, fluoro, and chloro;

G is $L^2Q$;

$L^2$ is methylene;

Q is a substituted or unsubstituted N-morpholinyl;

wherein each of the above alkyl, alkylene, alkenyl, heterocyclyl, cycloalkyl, carbocyclyl, and aryl groups of Formula (I) may each be independently and optionally substituted with between 1 and 3 substituents independently selected from methoxy, halo, amino, nitro, hydroxyl, and $C_{1-3}$ alkyl;

and wherein 1-3 substituents of Q can be further independently selected (in addition to the preceding paragraph) from tert-butyloxycarbonyl, carboxamide, $C_{1-6}$ alkyl, 5-9-membered heterocyclyl, N($C_{1-6}$ alkyl)(5-9 membered heterocyclyl), NH(5-9 membered heterocyclyl), O(5-9 membered heterocyclyl), (5-9 membered heterocyclyl)$C_{1-3}$ alkylene, phenyl, $C_{1-2}$-hydroxyalkylene, $C_{2-6}$ alkoxy, ($C_{3-6}$ cycloalkyl)-O—, phenyl, (phenyl)$C_{1-3}$ alkylene, and (phenyl)$C_{1-3}$ alkylene-O— and where said substituent groups of Q may optionally have between 1 and 3 substituents independently selected from trifluoromethyl, halo, nitro, cyano, and hydroxy; or a pharmaceutically acceptable salt, ester, or amide thereof.

2. A compound of claim 1, wherein $NR^1R^2$ taken together form piperidinyl, methylpiperidinyl, dimethylamino, pyrrolidinyl, diethylamino, methylethylamino, ethylpropylamino, or dipropylamino.

3. A compound of claim 2, wherein $NR^1R^2$ taken together form piperidinyl, pyrrolidinyl, or diethylamino.

4. A compound of claim 3, wherein $NR^1R^2$ taken together form piperidinyl or pyrrolidinyl.

5. A compound of claim 1, wherein one of $R^4$ and $R^5$ is G.

6. A compound of claim 5, wherein $R^4$ is G.

7. A compound of claim 5, wherein $R^5$ is G.

8. A compound of claim 1, wherein claim 1, wherein n is 1.

9. A compound of claim 1, wherein Q is optionally substituted with between 1 and 3 substituents selected from hydroxyl, carboxamide, $C_{1-6}$ alkyl, 5-9 membered heterocyclyl, N($C_{1-6}$ alkyl)(5-9 membered heterocyclyl), NH(5-9 membered heterocyclyl), (5-9 membered heterocyclyl)$C_{1-3}$ alkylene, $C_{1-2}$-hydroxyalkylene, O(5-9 membered heterocyclyl), $C_{1-6}$ alkoxy, ($C_{3-6}$ cycloalkyl)-O—, phenyl, (,phenyl)$C_{1-3}$ alkylene, and (phenyl)$C_{1-3}$ alkylene-O— where each of above heterocyclyl, phenyl, and alkyl groups may be optionally substituted with from 1 to 3 substituents independently selected from halo, nitro, cyano, and $C_{1-3}$ alkyl.

10. A compound of claim 1, wherein Q is substituted with a substituent comprising a $C_{1-6}$ heterocyclyl group selected from: pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, thiazolyl, (pyrrolyl)$C_{1-6}$ alkylene, and pyrrolyl.

11. A compound of claim 1, wherein n is 1;

$R^1$ and $R^2$ are independently selected from $C_2$ alkyl, or taken together with the nitrogen to which they are attached, they form a non-aromatic 5-6 membered heterocyclyl optionally including an additional heteroatom independently selected from O, S, and N;

one of $R^3$, $R^4$, and $R^5$ is G and the two remaining are H;

G is $L^2Q$;

$L^2$ is methylene;

Q is a substituted or unsubstituted N-morpholinyl;

wherein each of the above alkyl, alkylene, alkenyl, alkenylene, heterocyclyl, and carbocyclyl groups may each be independently and optionally substituted with between 1 and 3 substituents selected from methoxy, halo, amino, nitro, hydroxyl, and $C_{1-3}$ alkyl;

and wherein substituents of Q can be further selected from tert-butyloxycarbonyl, carboxamide, 5-9-membered heterocyclyl, NH(6-membered heterocyclyl), O(6-membered heterocyclyl), phenyl, $C_2$-hydroxyalkylene, hydroxy, benzyl and, where each of above heterocyclyl, phenyl, and alkyl substituent groups of Q may be optionally substituted with trifluoromethyl;

or a pharmaceutically acceptable salt, ester, or amide thereof.

12. A compound of claim 1, wherein $NR^1R^2$ taken together form piperidinyl, pyrrolidinyl, or diethylamino.

13. A compound of claim 1, wherein $NR^1R^2$ taken together form piperidinyl or pyrrolidinyl and n is 1.

14. A compound of claim 1, selected from: 4-[3-(4-piperidin-1-yl-but-1-ynyl)-benzyl]-morpholine; 4-[3-(4-piperidin-1-yl-but-1-ynyl)-benzyl]-morpholine dihydrochloride; 4-[4-(4-piperidin-1-yl-but-1-ynyl)-benzyl]- morpholine; 4-[4-(3-morpholin-4-ylmethyl-phenyl)-but-3-ynyl]-morpholine; 4-[3-(4-thiomorpholin-4-yl-but-1-ynyl)-benzyl]-morpholine; and 1-[3-(4-morpholin-4-yl-but-1-ynyl)-benzyl]-piperidin-4-ol.

15. A compound of claim 1, selected from: 4-[3-(4-piperidin-1-yl-but-1-ynyl)-benzyl]-morpholine; and 4-[3-(4-piperidin-1-yl-but-1-ynyl)-benzyl]-morpholine dihydrochloride.

16. A compound of claim 1, selected from 4-[3-(4-piperidin-1-yl-but-1-ynyl)-benzyl]-morpholine and 4-[4-(4-piperidin-1-yl-but-1-ynyl)-benzyl]-morpholine.

17. A compound of claim 1, having the structure 4-[3-(4-piperidin-1-yl-but-1-ynyl)-benzyl]-morpholine.

18. A compound of claim 1, selected from: 4-[4-(3-morpholin-4-ylmethyl-phenyl)-but-3-ynyl]-morpholine; and 4-[3(4-thiomorpholin-4-yl-but-1-ynyl)-benzyl]-morpholine.

19. A pharmaceutical composition, comprising a compound of claim 1 and a pharmaceutically-acceptable excipient.

20. A method of treating a subject having a disease or condition selected from the group consisting of, arousal/vigilance disorders, migraine, asthma, epilepsy, narcolepsy, eating disorders, motion sickness, vertigo, schizophrenia, nasal congestion, allergic rhinitis, and upper airway allergic response, comprising administering to a subject a therapeutically effective amount of a compound of claim 1.

21. A method for treating one or more disorders or conditions selected from the group consisting of, narcolepsy, and arousal/vigilance disorders, comprising administering to a subject a therapeutically effective amount of a compound of claim 1.

* * * * *